United States Patent
Stevenson et al.

(10) Patent No.: US 11,666,683 B2
(45) Date of Patent: *Jun. 6, 2023

(54) TEXTILE PRODUCTS HAVING A SEALANT OR COATING AND METHOD OF MANUFACTURE

(71) Applicant: Hothouse Medical Limited, Strathclyde (GB)

(72) Inventors: David Granville Stevenson, Strathclyde (GB); Timothy Rawden Ashton, Strathclyde (GB)

(73) Assignee: Hothouse Medical Limited, Glasgow (GB)

( * ) Notice: Subject to any disclaimer, the term of this patent is extended or adjusted under 35 U.S.C. 154(b) by 212 days.

This patent is subject to a terminal disclaimer.

(21) Appl. No.: 17/308,508

(22) Filed: May 5, 2021

(65) Prior Publication Data

US 2021/0260251 A1     Aug. 26, 2021

Related U.S. Application Data

(63) Continuation of application No. 17/126,314, filed on Dec. 18, 2020, which is a continuation of application
(Continued)

(30) Foreign Application Priority Data

Oct. 31, 2017 (GB) ...................... 1717885

(51) Int. Cl.
*A61L 27/50* (2006.01)
*A61L 27/34* (2006.01)
(Continued)

(52) U.S. Cl.
CPC .............. *A61L 27/507* (2013.01); *A61F 2/06* (2013.01); *A61F 2/07* (2013.01); *A61L 27/34* (2013.01);
(Continued)

(58) Field of Classification Search
CPC ........... A61L 2420/00–08; A61L 27/28; A61L 27/507; A61L 31/08; A61F 2002/077;
(Continued)

(56) References Cited

U.S. PATENT DOCUMENTS 4,459,252 A    7/1984   MacGregor
4,657,544 A    4/1987   Pinchuk
(Continued)

FOREIGN PATENT DOCUMENTS

CN     101573149 A    11/2009
DE      2913510 A1    10/1979
(Continued)

OTHER PUBLICATIONS

King et al., Can. Textile J. 108(4):24-30 (1991) (Year: 1991).*
(Continued)

*Primary Examiner* — Keri J Nelson
*Assistant Examiner* — Rebecca Lynee Zimmerman
(74) *Attorney, Agent, or Firm* — Hoffmann & Baron, LLP

(57) ABSTRACT

A medical textile product includes a textile substrate having opposed first and second surfaces with the textile substrate including a textile construction of one or more yarns. The second surface includes a coating of a substantially water-insoluble, non-porous elastomeric sealant. The one or more yarns at the first surface are pre-treated with a removable composition, such that the water-insoluble elastomeric sealant encapsulates a portion of fibers of the one or more yarns at the second surface of the textile substrate. The textile substrate is substantially impermeable to fluid. The first surface is substantially free of the substantially water-insoluble elastomeric sealant. The textile substrate may be a non-tubular substrate, such as a planar sheet, a shaped sheet, and a tape, or a tubular substrate, such as a cylindrical
(Continued)

conduit, a tubular conduit, a Y-shaped, a T-shaped conduit, a multi-channel conduit, and a bulbous shaped conduit.

30 Claims, 18 Drawing Sheets

Related U.S. Application Data

No. 16/273,320, filed on Feb. 12, 2019, now Pat. No. 10,926,003, which is a continuation of application No. PCT/GB2018/053161, filed on Oct. 31, 2018.

(51) Int. Cl.

| | | |
|---|---|---|
| *A61F 2/06* | (2013.01) | |
| *A61L 31/08* | (2006.01) | |
| *A61F 2/07* | (2013.01) | |
| *A61L 27/48* | (2006.01) | |
| *A61L 27/52* | (2006.01) | |
| *A61L 27/56* | (2006.01) | |
| *A61L 31/10* | (2006.01) | |
| *A61L 31/12* | (2006.01) | |
| *A61L 31/14* | (2006.01) | |

(52) U.S. Cl.
CPC .............. *A61L 27/48* (2013.01); *A61L 27/502* (2013.01); *A61L 27/52* (2013.01); *A61L 27/56* (2013.01); *A61L 31/08* (2013.01); *A61F 2002/077* (2013.01); *A61L 31/10* (2013.01); *A61L 31/129* (2013.01); *A61L 31/146* (2013.01); *A61L 2420/02* (2013.01); *A61L 2420/08* (2013.01)

(58) Field of Classification Search
CPC ........ A61F 2/07; A61F 2/0063; A61F 2/0077; A61F 2250/0069; B05B 12/20–29; B05B 12/26; B05D 1/32–327; B32B 5/28; B81C 2201/0198
See application file for complete search history.

(56) References Cited

U.S. PATENT DOCUMENTS

| | | | |
|---|---|---|---|
| 4,718,907 A | 1/1988 | Karwoski et al. | |
| 4,743,252 A | 5/1988 | Martin, Jr. et al. | |
| 4,743,258 A | 5/1988 | Ikada et al. | |
| 5,163,951 A | 11/1992 | Pinchuk et al. | |
| 5,246,452 A | 9/1993 | Sinnott | |
| 5,298,276 A | 3/1994 | Jayaraman | |
| 5,383,927 A | 1/1995 | De Goicoechea et al. | |
| 5,840,240 A | 11/1998 | Stenoien et al. | |
| 5,851,229 A | 12/1998 | Lentz et al. | |
| 5,851,230 A | 12/1998 | Weadock et al. | |
| 5,866,217 A | 2/1999 | Stenoien et al. | |
| 6,939,377 B2 | 9/2005 | Jayaraman et al. | |
| 7,022,135 B2 | 4/2006 | Zilla et al. | |
| 7,211,108 B2 | 5/2007 | Furst et al. | |
| 7,297,159 B2 | 11/2007 | Hossainy et al. | |
| 7,329,531 B2 | 2/2008 | Keenan | |
| 8,414,910 B2 | 4/2013 | Wang | |
| 2002/0187288 A1 | 12/2002 | Lim et al. | |
| 2003/0055494 A1 | 3/2003 | Bezuidenhout et al. | |
| 2003/0149471 A1 | 8/2003 | Briana et al. | |
| 2003/0149474 A1 | 8/2003 | Becker | |
| 2004/0024448 A1 | 2/2004 | Chang et al. | |
| 2004/0182511 A1 | 9/2004 | Rakos et al. | |
| 2004/0215337 A1 | 10/2004 | Hasin et al. | |
| 2007/0043428 A1* | 2/2007 | Jennings | D01D 5/0015 623/1.42 |
| 2009/0012607 A1 | 1/2009 | Kim et al. | |
| 2009/0041823 A1 | 2/2009 | Larena-Avellanenda et al. | |
| 2015/0044408 A1 | 2/2015 | Caballero et al. | |
| 2016/0302911 A1 | 10/2016 | Soletti | |

FOREIGN PATENT DOCUMENTS

| | | |
|---|---|---|
| DE | 102013201065 | 7/2014 |
| EP | 2 086 603 B1 | 1/2013 |
| FR | 2908047 A1 | 5/2008 |
| JP | 2009-11804 A | 1/2009 |
| WO | WO 82/01647 A1 | 5/1982 |
| WO | WO 97/25938 A1 | 7/1997 |
| WO | WO 01/17571 A1 | 3/2001 |
| WO | WO 03/015837 A1 | 2/2003 |
| WO | WO 03/066118 A1 | 8/2003 |
| WO | WO 2005/025840 A2 | 3/2005 |
| WO | WO 2005/058382 A1 | 6/2005 |
| WO | WO 2006/026725 A2 | 3/2006 |
| WO | WO 2006/038031 A2 | 4/2006 |
| WO | WO 2008/030939 A2 | 3/2008 |
| WO | WO 2010/086863 A2 | 8/2010 |
| WO | WO 2013/110720 A1 | 8/2013 |
| WO | WO 2014/025506 A1 | 2/2014 |

OTHER PUBLICATIONS

King, Martin w., "Designing Fabrics for Blood Vessel Replacement", Canadian Textile Journal, May 1991, pp. 24-30.
Morota, T. et al., "Development and Physical Characteristics of Novel Zero-Porosity Vascular Graft "Triplex®"", 2013, pp. 67-73, Annals of Vascular Diseases, vol. 6, No. 1.
Ravi, S. et al., "Biomaterials for vascular tissue engineering", Regen. Med., Jan. 2010, pp. 1-21, National Institute of Health.
Teodorescu,Mirela et al., "Poly(vinylpyrrolidone)—A Versatile Polymer for Biomedical and Beyond Medical Applications", Polymer Plastics Technology and Engineering54: pp. 923-943, 2015.
Zhu, R., et al., "Synthesis of polycarbonate urethane elastomers and effects of chemical structures on their thermal, mechanical and biocompatibility properties", Heliyon, 2016, pp. 1-17.
Phaneuf, Matthew D. et al., "Coating of Dacron vascular grafts with an ionic polyurethane: a novel sealant with protein binding properties", Biomaterials 22 (2001), pp. 463-469.
Maju, Sarawathy, et al., "Evaluation of alginate diadehyde cross-linked gelatin hydrogen as a biodegradable sealant for polyester vascular graft", Journal of Biomedical Materials Research B: Applied Biomaterials, Jul. 2011, vol. 98B, Issue 1,pp. 139-149.
Office Action dated Aug. 26, 2021 for Chinese Application No. 201880082755.7 with English translation.

\* cited by examiner

TEXTILE PRODUCTS HAVING A SEALANT OR COATING AND METHOD OF MANUFACTURE

CROSS-REFERENCE TO RELATED APPLICATIONS

This application is a Continuation of U.S. application Ser. No. 17/126,314, filed Dec. 18, 2020, which is a Continuation of U.S. patent application Ser. No. 16/273,320, filed Feb. 12, 2019, now U.S. Pat. No. 10,926,003 B2, issued Feb. 23, 2021, which is a Continuation of International Application No. PCT/GB2018/053161, filed Oct. 31, 2018, which designated the United States of America, and which embodiments the benefit of Great Britain Application No. GB 1717885.6, filed Oct. 31, 2017, the contents of all of which are incorporated by reference herein.

FIELD OF THE INVENTION

This invention relates to textile products, such as a vascular or endovascular prostheses having a selectively applied sealing layer or coating and particularly but not exclusively, a method of manufacturing the textile products, such as prostheses, a kit of parts for manufacturing the textile products, such as prostheses, a vascular system including the prosthesis, a method of implanting the prosthesis and a method of implanting the vascular system.

BACKGROUND TO THE INVENTION

Vascular prostheses, or grafts, are used extensively in surgical procedures, such as in treating abdominal and thoracic vascular disease. Vascular grafts are typically required to be sealed prior to implantation, in order to prevent blood from leaking from the vascular graft after implant. Known techniques for sealing vascular grafts include the use of biodegradable (or bioresorbable or bioabsorbable) animal-derived materials such as bovine gelatine, bovine albumin or bovine collagen to seal the graft. Other techniques for sealing vascular grafts use synthetic materials, some of which are not able to biodegrade when implanted in a human or animal body.

It is desirable for the sealed graft, once implanted in a human or an animal body, to allow the ingrowth of tissue on the inner surface of the vascular graft and to ensure that the ingrowing tissue adheres to the inner surface of the vascular graft. However, conventional techniques for sealing vascular grafts often suffer from the ingress of the sealant into the inner surface of the vascular graft. The presence of sealing material has an adverse effect on the growth of tissue on the inner surface of the graft. Furthermore, the presence of sealing material on the inner surface of the graft also contributes to poor adhesion between the ingrowing tissue and the vascular graft, which can lead to reduced vascular performance of the vascular graft. It is therefore desirable to provide a vascular graft which does not hinder the ingrowth of tissue and which allows the ingrowing tissue layer to adhere to the inner surface.

In an attempt to better enable growth and adhesion of tissue on the inner surface of the graft, biodegradable animal-derived materials such as those noted above can be used to seal the graft. When such a graft is implanted, it is desirable for the sealant material to degrade once the ingrowing tissue layer is sufficiently mature. However, conventional methods of sealing vascular grafts do not exhibit consistent and predictable degradation times. This has considerable implications on the performance of some vascular grafts. For example, if the sealant material degrades before the ingrowing tissue layer has developed into a pseudointima (an example of a tissue layer on the inner surface of a vascular graft), blood will leak from the vascular graft. If the sealant material degrades too slowly, the ingrowing tissue will suffer from poor adhesion to the inner surface of the graft (because the inner surface of the graft is still coated in sealing material), and is likely to delaminate from the vascular graft. Haemorrhagic dissection could then occur in the pseudointima. There is therefore a need to provide a method of sealing vascular grafts that enables predictable growth and adhesion of tissue to the inner surface of the vascular graft.

A further issue with existing vascular grafts is that some animal-derived sealants of the type typically used are thought to increase the risk of bovine spongiform encephalopathy (BSE) transmission. This risk is usually mitigated by extensive supply chain regulation requirements, which are onerous and burdensome. It is desirable to provide a vascular graft which has less burdensome regulatory requirements, such that new materials and designs can be brought to use in a shorter time and in a more cost-effective way.

Furthermore, animal-derived sealants are incompatible with an array of processing techniques, which limits the options available to vascular graft designers. Vascular grafts sealed using animal-derived sealants are also typically required to be transported, or packaged, with control over the temperature and humidity to obviate deterioration of the sealant material. Therefore, it would also be desirable to provide a vascular graft which has less stringent transport and packaging requirements.

Furthermore, elastomeric coatings may change the flexibility of the fabric and, when fashioned into medical products such as vascular grafts and the like, may have a deleterious effect on the handling characteristic which are very important to surgeons. Thus, it would be desirable to provide a vascular graft which has sufficient sealing due to an elastomeric coating on the external surface and which is substantially free of the same coating material on the opposing side, e.g., luminal side, and also has flexibility and handling characteristics acceptable to surgeons.

SUMMARY OF THE INVENTION

The masking agent may be a water-soluble polymer layer, a water-soluble polymer, a water-soluble material, a water-soluble coating and/or a water-soluble layer.

The sealant may be a water-insoluble material, a water-insoluble sealant, a water-insoluble coating, and/or a water-insoluble layer.

For purposes of this invention, the water-soluble layer and the water-insoluble layer are applied to textile fabrics, medical device fabrics, implantable medical device textiles and various configurations of medical and non-medical textiles.

It is an object of the present invention to provide a vascular prosthesis and/or a method of manufacturing a vascular prosthesis, the inner surface of which better allows the ingrowth of biological tissue. One aspect of the present invention is to provide an implantable textile, such as a vascular prosthesis, and/or a method of manufacturing an implantable textile, such as a vascular prosthesis, the inner surface of which better allows the ingrowth of biological tissue. It is a further aspect of the present invention to provide an implantable textile, such as a vascular prosthesis, and/or a method of manufacturing an implantable textile, such as a vascular prosthesis, the inner surface of which is substantially devoid of sealing material. Another aspect of the present invention is to provide a vascular prosthesis and/or a method of manufacturing a vascular prosthesis, which better facilitates ingrowing tissue to adhere to the inner surface of the vascular prosthesis. It is a further aspect of the present invention to provide a vascular prosthesis and/or a method of manufacturing a vascular prosthesis, which better allows for predictable growth and adhesion of tissue to the inner surface of the vascular prosthesis. It is still a further aspect of the invention to provide a vascular prosthesis which strikes a balance between too much and too little masking agent. Too little masking agent will allow the sealant to migrate through the graft wall. Too much masking agent on the outside interferes with sealant adhesion and thus affects the ability to reach the permeability that is require in a vascular prosthesis. There must be sufficient masking agent to prevent sealant penetration balanced with the amount of masking agent that ends up on the outer graft surface. It is also an aspect of the invention to achieve a balance between the amount of sealant coverage and sealant adhesion required to attain adequate sealing and too much sealant such that it destroys the flexibility and handling characteristics of the prosthesis.

It is also a further aspect of the present invention to provide a kit of parts for manufacturing a vascular prosthesis. It is a further aspect of the present invention to provide a vascular system which allows, for example, synthetic assistive heart components to be connected to blood vessels and the heart.

It is a further aspect of the present invention to mitigate or at least obviate at least some of the issues in the prior art. Further aspects and embodiments of the present invention will be apparent from a reading of the present document.

According to a first aspect of the invention there is provided a method of manufacturing a vascular prosthesis, the method comprising the steps of:
(i) providing a conduit comprising a wall, the wall of the conduit comprising an inner surface and an outer surface, at least a section of the conduit being porous;
(ii) adding a masking agent to at least a part of the porous section of the conduit; and
(iii) adding a sealant to at least a part of the porous section of the conduit, the sealant being configured to mitigate movement of fluid through the wall of the conduit;
wherein the masking agent is configured to mitigate presence of the sealant on the inner surface of the conduit.

The vascular or endovascular prosthesis of the present invention is not limited to a prosthesis comprising a conduit or tubular portion. The vascular or endovascular prosthesis of the present invention may be or may comprise a non-conduit or non-tubular shaped structure or portion. Thus, the wall of the vascular or endovascular prosthesis being subjected to the masking agent and the sealant is not limited to a conduit wall. Thus, a substrate may be a non-conduit shaped structure or portion. Further, medical textile products are within the scope of the present invention.

The sealant may form a sealing layer on at least a part of the outer surface of the wall of the conduit.

The sealant may form a sealing layer on substantially all of the outer surface of the wall of the conduit.

The masking agent may form a masking agent layer on at least a part of the inner surface of the wall of the conduit.

The masking agent may form a masking agent layer on substantially all of the inner surface of the wall of the conduit.

Substantially all of the conduit may be porous.

The method may comprise one or more masking agent removal steps, the, or each, masking agent removal step comprising the step of removing at least a part of the masking agent from the conduit.

The method may comprise the step of removing at least a part of the masking agent from at least a part of the outer surface of the wall of the conduit prior to the step of adding the sealant to the porous section of the conduit.

The method may comprise the step of removing at least a part of the masking agent from the inner surface of the wall of the conduit subsequent to the step of adding the sealant to at least a part of the porous section of the conduit.

The method may comprise the step of removing substantially all of the masking agent from the conduit subsequent to the step of adding the sealant to at least a part of the porous section of the conduit.

At least one of the masking agent removal steps may be carried out at a temperature of between approximately 15° C. and approximately 140° C.

At least one of the masking agent removal steps may comprise the step of removing at least a part of the masking agent by applying a solvent thereto.

The solvent may comprise water.

The conduit may be at least one of: agitated, rotated, spun, and shaken, or the like, during at least one of the masking agent removal steps.

At least one of the masking agent removal steps may be carried out by etching, plasma etching, ablating and/or abrading the masking agent.

The inner surface of the wall of the conduit may be configured to promote the growth of biological tissue thereon.

The masking agent may comprise a polymer.

The masking agent may comprise a water-soluble polymer.

The masking agent may comprise at least one of: polyvinylpyrrolidone, glycerol, methyl cellulose, poly(ethylene glycol) and poly(ethylene glycol) hydrogel. The masking agent may comprise at least one of: polyvinylpyrrolidone (PVP), glycerol, methyl cellulose, poly(ethylene glycol) (PEG), polyethylene oxide (PEO), and poly(ethylene glycol) hydrogel. The masking agent may also include other biological hydrophilic polymers as described herein.

The masking agent may be biocompatible.

The masking agent may form a biocompatible masking agent layer when added to the conduit.

The masking agent may be added to at least a part of the porous section of the conduit from a masking agent solution. As used herein porous refers to being permeable to the passage of liquids such as blood under normal physiological conditions in a human patient.

The masking agent solution may be a polymer solution.

The step of adding the masking agent to at least a part of the porous section of the conduit may be performed by spraying the masking agent solution onto at least a part of the porous section of the conduit.

The masking agent solution may be added to the conduit by spraying the masking agent onto at least a part of the inner surface of the wall of the conduit.

The step of adding the masking agent to at least a part of the porous section of the conduit may be performed by immersing at least a part of the porous section of the conduit in the masking agent solution.

Substantially all of the conduit may be immersed in the masking agent solution.

The masking agent solution may comprise between approximately 5% weight/volume (w/v) of polymer in solution and approximately 30% w/v of polymer in solution.

The method may be carried out such that the step of adding the sealant to at least a part of the porous section of the conduit does not result in the removal of the masking agent from the porous section of the conduit.

The masking agent may be configured to biodegrade when the vascular prosthesis is implanted inside the human or animal body.

The conduit may be a woven fibrous polymer conduit.

The sealant may comprise a polymer.

The sealant may be a water-insoluble polymer.

The sealant may form a sealing layer when added to the conduit, the sealing layer being a polymer layer.

The sealant may comprise at least one of: silicone, room temperature vulcanising silicone, thermoplastic polyurethane, aliphatic polycarbonate, one or more thermoplastic elastomers, and polycarbonate.

The sealant may be added to the conduit from a sealant solution.

The sealant solution may be a polymer solution.

The sealant solution may comprise an organic solvent.

The sealant solution may comprise at least one of heptane and xylene.

The sealant may be added to at least a part of the porous section of the conduit by brushing and/or spraying the sealant thereon.

The sealant may be configured to mitigate movement of blood through the wall of the conduit.

The weight ratio of the sealant to the masking agent may be from about 0.1:1 to about 100:1. The weight ratio of the sealant to the masking agent may be from about 0.1:1 to about 71:1. The weight ratio of the sealant to the masking agent may be from about 0.1:1 to about 31:1.

The method may comprise the further step of sterilising the vascular prosthesis. The method may comprise the further step of sterilising the vascular prosthesis and/or medical device containing the textile substrate of the present invention.

The vascular prosthesis may be sterilised by way of at least one of: a gamma sterilisation process, an electron beam sterilisation process, and an ethylene oxide sterilisation process.

The conduit may be moveable between a contracted state and an extended state. The conduit may comprise a plurality of crimps. The conduit may comprise a plurality of crimps to provide, for example, flexibility for extending and contracting the conduit or prosthesis.

The step of adding the masking agent to at least a part of the porous section of the conduit may be carried out, at least in part, while the conduit is in the contracted state, in the extended state, and/or when moved between the contracted state and the extended state.

The step of adding the sealant to at least a part of the porous section of the conduit may be carried out, at least in part, while the conduit is in the contracted state, in the extended state, and/or when moved between the contracted state and the extended state.

The method may comprise one or more steps of weighing the conduit and/or measuring the length of the conduit, to determine, at least in part, the amount of masking agent, and/or or the amount of sealant, to add to at least a part of the porous section of the conduit.

The step of adding the masking agent to at least a part of the porous section of the conduit may comprise the step of providing gas to the conduit.

The gas may be directed towards the outer surface of the wall of the conduit.

The gas may be air.

The method may comprise the step of adding a support member to the conduit.

The support member may be added to the outer surface of the wall of the conduit.

The support member may be wrapped around the outer surface of the wall of the conduit.

The conduit may comprise a plurality of crimps, and the support member may be arranged to nest between the plurality of crimps.

The step of adding the support member to the conduit may be carried out prior to the step of adding the sealant to the conduit.

The step of adding the sealant to the conduit may be used, at least in part, to attach the support member to the conduit.

The support member may be a flexible, polymer member.

The method may comprise one or more steps of selectively adding sealant to one or more sections of the conduit, such that the conduit comprises at least two sections comprising substantially different amounts of sealant thereon.

The vascular prosthesis may be reversibly sealable. The masking agent may be selectively removable from the conduit. The masking agent may be added to, and subsequently removed from, the conduit. The sealant may be selectively removable from the conduit. The sealant may be added to, and subsequently removed from, the conduit. The masking agent and the sealant may be selectively removable from the conduit. The masking agent and the sealant may be added to, and subsequently removed from, the conduit.

The method may comprise one or more steps of adding the sealant to the conduit. The conduit may be configured to have variable flexibility throughout its length. The method may comprise the step of decreasing the flexibility of one or more sections of the conduit by adding sealant thereto. The method may comprise the step of selectively adding sealant to one or more sections of the conduit, such that the conduit comprises at least two sections comprising substantially different amounts of sealant thereon. The method may comprise one or more steps of selectively adding sealant to one or more sections of the conduit. The one or more steps of selectively adding sealant to one or more sections of the conduit may include adding sealant onto sealant that is present on the conduit. In this arrangement, different sections of the conduit may be configured to have different degrees of flexibility.

The vascular prosthesis may be configurable to be implantable inside the human or animal body. The vascular prosthesis may be configurable to be implantable or deliverable inside the human or animal body. The vascular prosthesis may be configured to be implantable inside the human or animal body. The vascular prosthesis may be configured to be implantable or deliverable inside the human or animal body.

The vascular prosthesis may be biocompatible. The term biocompatible used herein is in reference to materials which are compatible with implantation in the human or animal body, that is materials which can be implanted in the human or animal body without being harmful or toxic to surrounding tissue. The vascular prosthesis may be made from biocompatible materials. The vascular prosthesis may be made from substantially entirely biocompatible materials.

The vascular prosthesis may be a vascular graft. The vascular prosthesis may be configured to be flexible. The vascular prosthesis may be flexible.

The vascular prosthesis may have an inlet and an outlet. The vascular prosthesis may be configurable to allow fluid to flow from the inlet of the vascular prosthesis to the outlet of the vascular prosthesis. The vascular prosthesis may be configured to obviate fluid leaking therefrom. The vascular prosthesis may be configured to allow fluid to flow from the inlet of the vascular prosthesis to the outlet of the vascular prosthesis, and to prevent fluid from leaking from the vascular prosthesis. The step of adding the sealing layer to the porous section may configure the vascular prosthesis to obviate fluid leaking therefrom. The fluid may be a liquid. The fluid may be blood. It will be understood that the vascular prosthesis may be configured to obviate and/or prevent fluid leaking therefrom insofar as it is configured to obviate and/or prevent fluid from passing through the wall of the conduit of the vascular prosthesis.

The step of adding the sealant to at least a part of the porous section of the conduit may convert the conduit to a vascular prosthesis.

The vascular prosthesis may be made substantially entirely from polymeric materials.

The vascular prosthesis may be configured to obviate the leaking of blood therefrom at a blood pressure of up to approximately 300 mmHg (40 kPa), optionally up to approximately 200 mmHg (26.7 kPa).

The conduit may be made from a polymer material. The conduit may be a polymer conduit. The conduit may be made from one or more polymers. The conduit may be a woven conduit. The conduit may be a knitted conduit. The conduit may be made from woven fibres. The conduit may be a woven, polymer, fibrous conduit. The conduit may comprise polyester. The conduit may comprise polytetrafluoroethylene (PTFE). The conduit may comprise polyethylene terephthalate (PET). The conduit may comprise polyurethane (PU).

The method may comprise the step of applying heat to the conduit. The method may comprise the step of altering the shape of the conduit by applying heat to the conduit.

The conduit may be substantially cylindrically shaped. The conduit may be substantially tube shaped. The conduit may have a diameter of up to approximately 44 mm, optionally between approximately 8 mm and approximately 32 mm. The conduit may have a substantially uniform cross section throughout.

The conduit may comprise one or more crimps. The method may comprise the step of adding one or more crimps to the conduit. The method may comprise the step of mounting the conduit on a frame member. The method may comprise the step of affixing the conduit to a frame member. The frame member may be configurable to allow the conduit to move from the contracted state to the extended state. The frame member may be configurable to allow the conduit to move from the extended state to the contracted state. In the contracted state, the conduit may comprise between approximately 7 crimps per cm of length of the conduit and approximately 10 crimps per cm of length of the conduit. In the extended state, the conduit may comprise between approximately 4 crimps per cm of length of the conduit and approximately 6 crimps per cm of length of the conduit.

The conduit may comprise a twill-weave section. The conduit may be a twill-weave conduit. The conduit may be a 1/1 twill-weave. The conduit may comprise a plain-weave section. The conduit may be a plain-weave conduit. The weft yarn pick-rate of the conduit may be between approximately 25 ppcm and approximately 50 ppcm, optionally between approximately 36 ppcm and approximately 45 ppcm. Useful yarns may include multifilament yarns.

The conduit or medical textile is not limited to a woven textile. Other textile constructions, such as knitted textiles, braided textiles, fabric webs, fabric felts, filament spun textiles, and the like, can be used. Such textile or fabric constructions may be used with the methods, coatings, and/or masking agents of the present invention in both medical applications (including vascular and non-vascular applications) and non-medical applications.

In general, useful yarn materials include, but are not limited to, polyesters, polypropylenes, polyethylenes, polyurethanes, polytetrafluoroethylenes, and combinations thereof. The yarns may be of the monofilament, multifilament, or spun type. Multifilament yarns may contain from about 8 filaments to about 96 fiber filaments, desirably from about 20 filaments to about 40 filaments, more desirably from about 25 filaments to about 30 filaments. The yarns may have a linear density from about 18 denier (about 20 decitex) to about 140 denier (about 154 decitex), more desirably from about 30 denier (about 33 decitex) to about 60 denier (about 67 decitex), more desirably from about 40 denier (about 44 decitex) to about 45 denier (50 decitex). The yarns may be flat, twisted, and/or textured, and may have high, low or moderate shrinkage and/or bulk and crimp properties. Twisted yarns include S-twisted yarns and Z-twisted yarns. The number of twists per inch may vary from about 2 twists per inch (about 0.8 twists per cm) to about 15 twists per inch (about 6 twists per cm), more desirably from about 5 twists per inch (about 2 twists per cm) to about 12 twists per inch (about 5 twists per cm). Desirably, the yarns are single ply yarns or multi-ply yarns. Multi-ply yarns may contain from about 2 yarns per ply or bundle to about 4 yarns per ply or bundle.

The textile graft of the present invention may be woven from yarns using any known weave pattern, including simple plain weaves, basket weaves, twill weaves, velour weaves and the like. Weave patterns include warp yarns running along the longitudinal length of the woven product and weft also known as fill yarns running around the width or circumference of the woven product. The warp and the fill yarns are at approximately 90 degrees to one another with fabric flowing from the machine in the warp direction. The weave pattern may have from about 80 to about 325 warp yarns per inch (about 30 to about 128 warp yarns per cm) and about 80 to about 200 fill or weft yarns per inch (about 30 to about 80 fill yarns per cm). The wall thickness may be any conventional useful thickness, for example about 0.04 mm to about 1 mm.

Knitting involves the interlooping or stitching of yarn into vertical columns (wales) and horizontal rows (courses) of loops to form the knitted fabric structure. In warp knitting, the loops are formed along the textile length, i.e., in the wale or warp direction of the textile. Non-limiting stitch counts may include about 20 to about 60 wales per inch per layer (about 8 to about 25 wales per cm per layer) and 30 to 80 courses per inch per layer (about 12 to about 32 courses per cm per layer). Non-limiting overall number of stitches may vary from about 600 to about 5,000 stitches per square inch (about 100 to about 900 stitches per square centimeter). Useful knitting patterns include, but are not limited to, locknit knits (also referred to as tricot or jersey knits), reverse locknit knits, sharkskin knits, queenscord knits, atlas knits, velour knits, and the like. The wall thickness may be any conventional useful thickness, for example about 0.1 mm to about 1.5 mm.

The conduit may comprise one or more inlets. The conduit may comprise one or more outlets. The conduit may be a Y-shaped conduit. The conduit may be a T-shaped conduit. The conduit may be one or more of a cylindrical, tubular, Y-shaped, T-shaped, and multi-channel conduit. The conduit may have a bulbous shape or a portion having a bulbous shape. Such a bulbous shape may have, but is not limited to, a Valsalva aortic root profile. The present invention, however, is not limited to the conduit-shaped textiles. Other shaped textiles, such as planar or shaped sheets or tapes, may be used with the present invention.

The conduit may be a porous conduit. The conduit may be a porous conduit, for example having a water permeability of greater than 0.16 ml/min/cm$^2$ at 120 mm Hg pressure.

The inner surface of the wall of the conduit may be configured to promote biological tissue growth thereon. The inner surface of the wall of the conduit may be configured to allow biological tissue to grow thereon. The inner surface of the wall of the conduit may be configured to promote the growth of biological tissue thereon, at least in part by being substantially devoid of the sealant. The inner surface of the wall of the conduit may be configured to promote the growth of pseudointima. The inner surface of the wall of the conduit may be configured to allow the growth of pseudointima to occur thereon. The inner surface of the wall of the conduit may be configured to promote the adhesion of biological tissue thereto. The inner surface of the wall of the conduit may be configured to allow biological tissue to adhere thereto. The inner surface of the wall of the conduit may be configured to promote the adhesion of platelets thereto.

The inner surface of the wall of the conduit may be fibrous. The inner surface of the wall of the conduit may comprise woven fibres. The inner surface of the wall of the conduit may comprise a braided section. The inner surface of the wall of the conduit may be a substantially braided surface.

The masking agent may form a sacrificial layer. The masking agent may form a masking layer. The masking agent may form a sacrificial masking layer on at least a part of the conduit. The masking agent may be reversibly applicable to the conduit.

The masking layer may be an oleophobic layer.

The masking agent may be added to at least a part of the conduit. The masking agent may be added to substantially all of the conduit. The masking agent may be added to substantially all of the porous section of the conduit. The masking agent may be added to the inner surface of the wall of the conduit.

The method may comprise the further step of removing at least part of the masking agent from the conduit. The method may comprise one or more masking agent removal steps. The masking agent may be removed from the conduit by applying a masking agent remover to the masking agent.

The method may comprise a first masking agent removal step carried out prior to the step of adding the sealant to at least a part of the porous section. The method may comprise a second masking agent removal step carried out subsequent to the step of adding the sealant to at least a part of the porous section of the conduit. The method may comprise a first masking agent removal step carried out prior to the step of adding the sealant to at least a part of the porous section, and a second masking agent removal step carried out subsequent to the step of adding the sealant to at least a part of the porous section of the conduit.

The method may comprise the step of removing at least a part of the masking agent from the outer surface of the wall of the conduit. The method may comprise the step of removing at least part of the masking agent from the outer surface of the wall of the conduit, prior to the addition of the sealant. The method may comprise the step of removing at least a part of the masking agent from the outer surface of the wall of the conduit, such that at least a part of the outer surface of the wall of the conduit is devoid of the masking agent. In this arrangement, the sealant may be added to at least a part of the outer surface of the wall of the conduit.

The step of removing at least part of the masking agent from the outer surface of the wall of the conduit may be carried out by etching, plasma etching, abrading, and/or ablating.

The step of removing at least a part of the masking agent may comprise the step of applying a solvent to the masking agent. The solvent may be water.

The method may comprise the step of removing substantially all of the masking agent from the conduit. The step of removing substantially all of the masking agent from the conduit may be carried out after the step of adding the sealant to at least a part of the porous section of the conduit. The step of removing substantially all of the masking agent, when performed after the addition of the sealant to at least a part of the porous section of the conduit, may be carried out such that it does not result in the removal of the sealant from the conduit.

The step of removing substantially all of the masking agent may comprise the step of applying a solvent to the masking agent. The solvent may be water.

The step of removing at least a part of the masking agent may be carried out at a temperature of between approximately 15° C. and approximately 140° C., optionally between approximately 15° C. and approximately 95° C., optionally between approximately 35° C. and approximately 45° C., optionally approximately 40° C. The step of removing at least a part of the masking agent may be carried out for between approximately 40 minutes and approximately 300 minutes, optionally between approximately 40 minutes and approximately 60 minutes, optionally between approximately 45 minutes and approximately 55 minutes, optionally for approximately 51 minutes.

The step of removing at least a part of the masking agent may be carried out by applying gas to the conduit. The step of removing at least a part of the masking agent may be carried out by applying steam to the conduit. The step of removing at least a part of the masking agent may be carried out in an autoclave.

The method may comprise the step of agitating the conduit. The step of agitating the conduit may be carried out during any of the other steps of the method. The step of removing at least part of the masking agent may be carried out while agitating the conduit in a solution comprising a solvent. The solvent may be water.

When applied to the conduit, the masking agent may form a masking agent layer. The masking agent layer may be a polymer layer. The masking agent may be applied to the conduit using a masking agent solution. The method may comprise the step of applying the masking agent solution to the conduit. The method may comprise the further step of removing solvent from the masking agent solution.

The masking agent solution may comprise a solvent. The masking agent solution may comprise a polar solvent. The masking agent solution may comprise water.

The step of removing solvent from the masking agent solution may be carried out by evaporating solvent therefrom. The method may comprise the further step of evaporating solvent from the masking agent solution at a temperature of between approximately 15° C. and approximately 80° C., optionally between approximately 50° C. and approximately 80° C.

The masking agent may be added to the conduit by immersing the conduit in the masking agent. The masking agent may be added to the conduit by immersing the conduit in the masking agent solution. The masking agent may be added to the conduit by immersing the conduit in the masking agent solution while agitating the conduit. The masking agent may be added to the conduit by immersing the conduit in the masking agent, or in the masking agent solution, for up to approximately 1 minute. The masking agent may be added to the conduit by immersing the conduit in the masking agent, or in the masking agent solution, for up to approximately 1 minute while agitating the conduit.

The masking agent may be added to the conduit by applying a masking agent solution to the inner surface of the wall of the conduit. The masking agent may be added to the conduit by applying a masking agent solution to the outer surface of the wall of the conduit.

The masking agent may be added to the conduit by immersing the conduit in the masking agent, by dipping the conduit in the masking agent, by spray coating the masking agent onto the conduit, and/or by brushing the masking agent onto the conduit.

The masking agent solution may be added to the conduit by spraying the masking agent onto at least a part of the porous section of the conduit.

The masking agent may comprise polyvinylpyrrolidone (PVP). The masking agent may comprise PVP having a molecular weight of between approximately 6,000 g/mol and approximately 15,000 g/mol, optionally between approximately 8,000 g/mol and approximately 12,000 g/mol, optionally approximately 10,000 g/mol. The masking agent may comprise glycerol. The masking agent may comprise PVP and glycerol.

The masking agent may be water-soluble.

The masking agent solution may comprise PVP and water. The masking agent solution may comprise PVP, glycerol and water.

The masking agent may comprise between approximately 3% w/v and approximately 30% w/v of polymer in solution, optionally between approximately 5% w/v and approximately 30% w/v of polymer in solution, optionally between approximately 5% w/v and approximately 20% w/v of polymer in solution, optionally between approximately 5% w/v and approximately 10% w/v of polymer in solution, optionally between approximately 5% w/v and approximately 7% w/v of polymer in solution, optionally approximately 7% w/v of polymer in solution, optionally approximately 6% w/v of polymer in solution, optionally approximately 5% w/v of polymer in solution, optionally approximately 4% w/v of polymer in solution, optionally approximately 3% w/v of polymer in solution. The masking agent may comprise between approximately 3% w/v and approximately 80% w/v of polymer in solution.

The masking agent solution may comprise between approximately 3% w/v of PVP in solution and approximately 30% w/v of PVP in solution, optionally between approximately 5% w/v and approximately 30% w/v of PVP in solution, optionally between approximately 5% w/v and approximately 20% w/v of PVP in solution, optionally between approximately 5% w/v and approximately 10% w/v of PVP in solution, optionally approximately 7% w/v of PVP in solution, optionally approximately 6% w/v of PVP in solution, optionally approximately 5% w/v of PVP in solution, optionally approximately 4% w/v of PVP in solution, optionally approximately 3% w/v of PVP in solution.

The masking agent solution may comprise approximately 1% w/v of glycerol in solution. The masking agent solution may comprise approximately 6% w/v of PVP in solution, and approximately 1% w/v of glycerol in solution. The ratio of glycerol to masking agent in the masking agent solution may be between approximately 1% and approximately 100%. The ratio of glycerol to masking agent in the masking agent solution may be between approximately 1% and approximately 30%, optionally between approximately 1.5% and approximately 30%, optionally between approximately 5% and approximately 30%, optionally between approximately 1% and approximately 20%, optionally between approximately 1% and approximately 15%, and optionally between approximately 1% and approximately 10%.

The masking agent may comprise methyl cellulose. The masking agent may comprise poly(ethylene glycol) (PEG). The masking agent may comprise PEG hydrogel.

The masking agent may be made from a biocompatible material, or from biocompatible materials. Applying the masking agent to the conduit may form a biocompatible layer.

The terms biodegrade, biodegradable, bioabsorbable and bioresorbable are used herein to refer to materials which degrade over time when implanted in the human or animal body.

The masking agent may comprise a bioresorbable, or a biodegradable material. The masking agent may be biodegradable. The masking agent may be configured to biodegrade when implanted inside a human or animal body. The masking agent may be configured to bioresorb when implanted inside a human or animal body. The masking agent may be a biodegradable polymer. The masking agent may comprise a biodegradable polymer. The masking agent may be configurable to be biodegradable.

During the step of adding the masking agent to at least a part of the porous section of the conduit, the conduit may be moved from the contracted state to the extended state. During the step of adding the masking agent to at least a part of the porous section of the conduit, the conduit may be moved from the extended state to the contracted state. The step of adding the masking agent to at least a part of the porous section of the conduit may be carried out while the conduit is moved between the contracted state and the extended state. The step of adding the masking agent to at least a part of the porous section of the conduit may be carried out while the conduit is in the contracted state. The step of adding the masking agent to at least a part of the porous section of the conduit may be carried out while the conduit is in the extended state. One or more of the steps of the method may be carried out while the conduit is moved between the contracted state and the extended state.

The step of moving the conduit between the contracted state and the extended state may elongate the conduit by a factor of up to approximately 100%. The step of moving the conduit between the contracted state and the extended state may elongate the conduit by a factor of between approximately 45% and approximately 55%. The step of moving the conduit between the contracted state and the extended state may elongate the conduit by a factor of approximately 50%. In the contracted state, the length of the conduit may be reduced from its fully extended length by a factor of between approximately 20% and approximately 80%, optionally between approximately 20% and approximately 40%, optionally between approximately 40% and approximately 60%. In the extended state, the length of the conduit may be reduced from its fully extended length by a factor of between approximately 20% and approximately 80%, optionally between approximately 20% and approximately 40%, optionally between approximately 40% and approximately 60%.

The step of adding the masking agent to at least a part of the porous section of the conduit may include providing gas to the conduit. The gas may be configured to flow towards the outer surface of the wall of the conduit. In this arrangement, the step of adding the masking agent to the conduit results in the masking agent being formed preferentially on the inner surface of the wall of the conduit. In this arrangement, the outer surface of the wall of the conduit may remain substantially devoid of the masking agent. The gas may be air.

The sealant may be configured to substantially block the porous section of the conduit, such that the flow of fluid through the porous section of the conduit is mitigated. The sealant may be configured to prevent, or obviate, movement of fluid through the wall of the conduit. The fluid may be blood.

The sealant may be added to at least a part of the outer surface of the wall of the conduit. The sealant may be added to substantially all of the outer surface of the wall of the conduit.

The method may be carried out such that the step of adding the sealant to at least a part of the porous section of the conduit does not result in the removal of the masking agent. In this arrangement, the sealant and the masking agent are compatible with each other. That is, the sealant and the masking agent can be in contact with each other without either the sealant or the masking agent being damaged or, when applied to the conduit, from being removed therefrom.

The sealant may be biocompatible. The sealant may be made from a biocompatible material, or from biocompatible materials. The sealant may form a sealing layer. The sealing layer may be a biocompatible layer. The sealant may form a biocompatible layer.

The sealant may be a polymer. The sealing layer may be a polymer layer. The sealant may comprise polyurethane. The sealant may comprise thermoplastic polyurethane (TPU). The sealant may comprise silicone. The sealant may comprise polyurethane and silicone. The sealant may comprise TPU and silicone. The sealant may comprise aliphatic polycarbonate. The sealant may comprise polyurethane and aliphatic polycarbonate. The sealant may comprise TPU and aliphatic polycarbonate. The sealant may comprise room temperature vulcanising (RTV) silicone. The sealant may comprise RTV silicone elastomer. The sealant may comprise polycarbonate. The sealant may comprise one or more thermoplastic elastomers.

The sealant solution may comprise polyurethane. The sealant solution may comprise TPU. The sealant solution may comprise silicone. The sealant solution may comprise polyurethane and silicone. The sealant solution may comprise TPU and silicone. The sealant solution may comprise aliphatic polycarbonate. The sealant solution may comprise polyurethane and aliphatic polycarbonate. The sealant solution may comprise TPU and aliphatic polycarbonate. The sealant solution may comprise RTV silicone. The sealant solution may comprise RTV silicone elastomer. The sealant solution may comprise polycarbonate. The sealant solution may comprise one or more thermoplastic elastomers.

The organic solvent may be an aprotic solvent. The organic solvent may be a non-polar solvent. The sealant solution may comprise xylene. The sealant solution may comprise heptane. The sealant solution may comprise silicone and heptane. The sealant solution may comprise silicone and xylene. The sealant solution may comprise RTV silicone elastomer and heptane. The sealant solution may comprise RTV silicone elastomer and xylene. The sealant solution may comprise polyurethane and heptane. The sealant solution may comprise polyurethane and xylene. The sealant solution may comprise polycarbonate and heptane. The sealant solution may comprise polycarbonate and xylene.

The sealant solution may comprise a polar solvent. The sealant solution may comprise dimethylacetamide (DMAC). The sealant solution may comprise tetrahydrofuran (THF). The sealant solution may comprise TPU and DMAC. The sealant solution may comprise thermoplastic polyurethane and THF.

The sealant may be configurable to mitigate against environmental stress cracking. The sealant, when applied to the conduit may be configured to mitigate against environmental stress cracking.

The method may comprise the step of removing solvent from the sealant. The method may comprise the step of removing solvent from the sealant solution. The step of removing solvent may be carried out by evaporating solvent from the sealant. The step of removing solvent may be carried out by evaporating solvent from the sealant solution.

The sealant may be added to the conduit by brushing the sealant onto the conduit. The sealant may be added to the conduit by spray-coating the sealant onto the conduit. The sealant may be added to the conduit by dipping the conduit in the sealant. The sealant may be added to the conduit by casting the sealant onto the conduit. The sealant may be added to the conduit by immersing the conduit in the sealant. The sealant may be added by vapour deposition. The sealant may be added by chemical vapour deposition. The sealant may be added by electrostatic spinning and/or filament spinning. The sealant may be added to the conduit by wiping the sealant onto the conduit. The sealant may be added to the conduit while the conduit is rotated about its longitudinal axis. The sealant may be added to the conduit while the conduit is rotated about its longitudinal axis at up to approximately 2,000 rpm, optionally between 700 rpm and 2,000 rpm, optionally between approximately 40 rpm and approximately 80 rpm, optionally at approximately 60 rpm.

Prior to applying the masking agent and the sealant, the surface of the textile, medical textile or medical device (e.g. prosthesis) may be surface treated with an elastomer. The elastomer may be the same elastomer as the sealant or it may be a different elastomer. Such surface treatment is designed to be a very light application of the elastomer to ensure that no elastomer penetrates through the wall of the textile fabric. Such surface treatment may be applied by light surface spraying, selective area coating or application of thin elastomeric fibers prior to their cure. For example, spots of elastomer may be placed along the length and radius. The purpose of surface treating is to ensure that the sealant will have a place to adhere in the event that excess masking agent unintentionally interferes with the sealant. The surface treatment will repel the masking agent, thus providing an attachment/adhesion site for the sealant.

The surface treatment may also be used to alter the properties of the textile to, for example, promote adhesion of the sealing agent thereat. This may involve surface activation for altering chemical adhesion properties on the textile for enhanced securement of the sealant thereat. Further, the hydrophilicity and/or hydrophobicity of portions of the textile may also be modified for enhanced attraction and/or repulsion of the masking agent(s) and/or sealants. Non-limiting techniques may include, but are not limited to, the use of plasma generation, including low pressure or vacuum generation, atmospheric pressure generation, elevated pressure generation, including for example, glow discharge generation, corona discharge generation, dielectric-barrier discharge generation, and the like. Further, ultraviolet irradiation and laser treatments may be used. Such preconditioning before applying the masking agent and/or the sealant may promote sealant attachment via physical and/or chemical modification of the textile substrate. Further, the textile patterns themselves may be modified to include greater extents of floating yarns to provide a raised yarn or velour surface to the textile where such raised yarns will provide greater access points for sealant securement to the graft.

During the step of adding the sealant to the conduit, the conduit may be moved from the contracted state to the extended state. During the step of adding the sealant to the conduit, the conduit may be moved from the extended state to the contracted state. During the step of adding the sealant to the conduit, the conduit may be moved between the contracted state and the extended state.

The step of adding the sealant to the conduit may be carried out, at least in part, when the conduit is in the contracted state. The step of adding the sealant to the conduit may be carried out, at least in part, when the conduit is in the extended state. The step of adding the sealant to the conduit may be carried out, at least in part, when the conduit is moved between the contracted state and the extended state.

The step of moving the conduit between the contracted state and the extended state may elongate the conduit by up to approximately 100%. The step of moving the conduit between the contracted state and the extended state may elongate the conduit by between approximately 45% and approximately 55%. In the contracted state, the length of the conduit may be reduced from its fully extended length by a factor of between approximately 20% and approximately 80%, optionally between approximately 20% and approximately 40%, optionally between approximately 40% and approximately 60%. In the extended state, the length of the conduit may be reduced from its fully extended length by a factor of between approximately 20% and approximately 80%, optionally between approximately 20% and approximately 40%, optionally between approximately 40% and approximately 60%.

The sealant, once added to the conduit, may comprise between approximately 4 mg per cm$^2$ and 19 mg per cm$^2$ of silicone, optionally approximately 8 mg per cm$^2$.

The method may comprise the further step of drying the vascular prosthesis. The further step of drying the vascular prosthesis may be carried out at a temperature of between approximately 15° C. to approximately 45° C. The further step of drying the vascular prosthesis may be carried out after the step of removing at least part of the masking agent from the conduit. The further step of drying the vascular prosthesis may be carried out after the step of adding the sealant to the conduit. The drying step may be configured to, at least in part, remove residual solvent, water, or the like, from the vascular prosthesis.

The further step of drying the vascular prosthesis may comprise the step of providing gas to the vascular prosthesis. The gas may be air.

The method may comprise multiple drying steps.

The, or each, drying step may be carried out at a temperature of between approximately 15° C. to approximately 45° C.

The method may comprise the step of weighing the conduit. The step of weighing the conduit may be carried out prior to the step of adding the masking agent to the conduit. The step of weighing the conduit may be carried out prior to the step of adding the sealant to the conduit. The step of weighing the conduit may be used to determine, at least in part, the amount of masking agent to be applied to the conduit. The step of weighing the conduit may be used to determine, at least in part, the amount of sealant to be applied to the conduit.

The method may comprise the step of measuring the length of the conduit. The measurement of the length of the conduit may be used, at least in part, to determine the amount of masking agent to be added to the conduit. The measurement of the length of the conduit may be used, at least in part, to determine the amount of sealant to be added to the conduit.

The weight of the conduit, and the length of the conduit, may be used, at least in part, to determine the amount of masking agent to be added to the conduit. The weight of the conduit, and the length of the conduit, may be used, at least in part, to determine the amount of sealant to be added to the conduit.

The support member may be added to the wall of the conduit. The support member may be added to the inner surface of the wall of the conduit. The support member may be added to the inner surface and the outer surface of the wall of the conduit. The sealant may be configured to attach the support member to the conduit. In this arrangement, the support member is added to the conduit and the sealant is then added to the conduit in order to seal the conduit, and to attach the support member to the conduit.

The support member may be a cable, wire or the like. The support member may comprise at least one of a polymer material, a metal material, a shape memory alloy, and a superelastic alloy. The support member may comprise at least one of: polyethylene terephthalate, polytetrafluoroethylene, polyurethane, polycarbonate, silicone, stainless steel, titanium, nickel, and nickel titanium (Nitinol). The support member may be a flexible member. The support member may be capable of being wrapped around the conduit. The support member may be arranged to nest between the crimps of the conduit. The support member may be a flexible, polymer wire. The support member may be a metallic or polymeric member, such as a shape memory metallic or polymeric member. The support member may be disposed at an inner portion of the conduit, at an outer portion of the conduit, within the textile wall of the conduit, and combinations thereof. The support member may be secured to the conduit by the sealant, for example the sealant may encapsulate the support member or the support member may be embedded in the sealant. In some embodiments, the support member may be secured to the conduit by other means, such as suturing, adhesive bonding, etc. The support member may be arranged longitudinally, radially or a combination thereof, about the conduit.

The support member may be biocompatible.

The vascular prosthesis may be connectable to one or more further prosthesis, or prostheses. The inlet of the vascular prosthesis may be connectable to an outlet of a further prosthesis. The outlet of the vascular prosthesis may be connectable to an inlet of a further prosthesis. The vascular prosthesis may be connectable to one or more heart valves, or synthetic heart valves. The vascular prosthesis may be connectable to a cardiac assist device, a ventricular assist device, a left ventricular assist device, and/or a right ventricular assist device, a biological heart valve, or the like. The further prosthesis may be a biological heart valve.

The vascular prosthesis may be connectable to one or more blood vessels. The vascular prosthesis may be connectable to one or more blood vessels by way of suture(s).

The vascular prosthesis may be locatable between a first end and a second end of a severed, or diseased, blood vessel. The inlet of the vascular prosthesis may be connectable to the first end of the severed, or diseased, blood vessel. The outlet of the vascular prosthesis may be connectable to the second end of the severed, or diseased blood vessel.

The method may comprise the step of sterilising the vascular prosthesis. The step of sterilising the vascular prosthesis may be carried out by way of a gamma sterilisation process. The further step of sterilising the vascular prosthesis may be carried out by way of an electron beam sterilisation process. The further step of sterilising the vascular prosthesis may be carried out by way of ethylene oxide sterilisation. The method may comprise one or more sterilisation steps. The vascular prosthesis may be configured to be capable of being sterilised, such that the vascular prosthesis is not damaged or structurally altered by being sterilised. The step of sterilising the vascular prosthesis may configure the vascular prosthesis to be suitable for implantation in the human or animal body.

According to a second aspect of the invention there is provided a vascular prosthesis comprising:

a conduit comprising a wall, the wall of the conduit comprising an inner surface and an outer surface, at least a section of the conduit being porous;

wherein at least a part of the porous section comprises a sealant configured to mitigate movement of fluid through the wall of the conduit; and wherein the inner surface of the wall of the conduit is substantially devoid of the sealant.

The sealant may form a sealing layer on at least a part of the outer surface of the wall of the conduit.

The sealant may form a sealing layer on substantially all of the outer surface of the wall of the conduit.

Substantially all of the conduit may be porous.

The inner surface of the wall of the conduit may be configured to promote the ingrowth of biological tissue thereon.

The conduit may be a woven fibrous polymer conduit.

The sealant may form a sealing layer, the sealing layer being a polymer layer.

The sealant may comprise at least one of: silicone, room temperature vulcanising silicone, thermoplastic polyurethane, aliphatic polycarbonate, one or more thermoplastic elastomers, and polycarbonate.

The sealant may be configured to mitigate movement of blood through the wall of the conduit.

The vascular prosthesis may be sterilised.

The vascular prosthesis may be sterilised by way of at least one of the following: a gamma sterilisation process, an ethylene oxide sterilisation process, and an electron beam sterilisation process.

The conduit may be moveable between a contracted state and an extended state.

The conduit may comprise a support member.

The support member may be located substantially adjacent to the outer surface of the wall of the conduit.

The support member may be wrapped around the outer surface of the wall of the conduit.

The conduit may comprise a plurality of crimps, the support member being arranged to nest between the plurality of crimps.

The sealant may be arranged to, at least in part, attach the support member to the conduit.

The support member may be a flexible, polymer member.

The conduit may be configured to have at least two sections having substantially different amounts of sealant thereon.

Embodiments of the second aspect of the invention may include one or more features of the first aspect of the invention or its embodiments. Similarly, embodiments of the first aspect of the invention may include one or more features of the second aspect of the invention or its embodiments.

According to a third aspect of the present invention there is provided a kit of parts for manufacturing a vascular prosthesis, the kit of parts comprising:

(i) a conduit comprising a wall, the wall of the conduit comprising an inner surface and an outer surface, at least a section of the conduit being porous;

(ii) a masking agent; and (iii) a sealant;

when applied to at least a part of the porous section of the conduit, the masking agent being configured to mitigate presence of the sealant on the inner surface of the conduit; and when applied to at least a part of the porous section of the conduit, the sealant being configured to mitigate movement of fluid through the wall of the conduit.

Addition of the sealant to at least a part of the porous section of the conduit may form a sealing layer on at least a part of the outer surface of the wall of the conduit.

Addition of the masking agent to at least a part of the porous section of the conduit may form a masking agent layer on at least part of the inner surface of the wall of the conduit.

Substantially all of the conduit may be porous.

The kit of parts may comprise a masking agent remover, the masking agent remover being operable to remove applied masking agent from the conduit.

The masking agent remover may comprise a solvent.

The solvent may comprise water.

The masking agent remover may be operable to remove applied masking agent from the conduit at a temperature of between approximately 15° C. and approximately 140° C.

The kit of parts may comprise an abrading tool, the abrading tool being operable to remove applied masking agent from the conduit.

The inner surface of the wall of the conduit may be configured to promote the ingrowth of biological tissue thereon.

The masking agent may comprise a polymer.

The masking agent may comprise a water-soluble polymer.

The masking agent applied to the conduit may form a masking agent layer, the masking agent layer being a polymer layer.

The masking agent may comprise at least one of: polyvinylpyrrolidone, glycerol, methyl cellulose, and poly(ethylene glycol) hydrogel. The masking agent may comprise at least one of: polyvinylpyrrolidone, glycerol, methyl cellulose, polyethylene oxide, and poly(ethylene glycol) hydrogel, as well as biological products as further described herein such as collagen and gelatine.

The masking agent may be biocompatible.

Masking agent applied to the conduit may form a biocompatible masking agent layer.

The kit of parts may comprise a masking agent solution, the masking agent solution being operable to apply masking agent to the conduit.

The masking agent solution may be a polymer solution.

The conduit may be immersible in the masking agent solution.

The masking agent solution may comprise between approximately 5% w/v of polymer in solution and approximately 30% w/v of polymer in solution.

When the masking agent and the sealant are applied to the conduit, the sealant may be configured such that addition of the sealant to the conduit does not result in the removal of the applied masking agent from the conduit.

The masking agent may be configured to biodegrade when implanted inside the human or animal body.

The conduit may be a woven fibrous polymer conduit.

The sealant may comprise a polymer, optionally a water-insoluble polymer.

The sealant, when applied to the conduit, may form a sealing layer, the sealing layer being a polymer layer.

The sealant may comprise at least one of: silicone, room temperature vulcanising silicone, thermoplastic polyurethane, aliphatic polycarbonate, one or more thermoplastic elastomers, and polycarbonate.

The kit of parts may comprise a sealant solution operable to apply sealant to the conduit.

The sealant solution may be a polymer solution.

The sealant solution may comprise an organic solvent.

The sealant solution may comprise at least one of heptane and xylene.

The kit of parts may comprise a sealant applicator operable to apply sealant to the conduit, and/or a masking agent applicator operable to apply masking agent to the conduit.

The sealant applicator may be an apparatus for spray coating the sealant, and/or a brush, or the like.

The masking agent applicator may be a brush, an apparatus for spray-coating the masking agent, an apparatus for dipping or immersing the conduit in the masking agent, and/or an apparatus for wiping the masking agent onto the conduit.

The sealant, when applied to at least a part of the porous section of the conduit, may be configured to mitigate movement of blood through the wall of the conduit.

The conduit may be moveable between a contracted state and an extended state.

The kit of parts may comprise a further prosthesis.

The further prosthesis may be at least one of: a biological heart valve, a synthetic heart valve, a cardiac assist device, and a ventricular assist device, or the like.

The kit of parts may comprise a weighing device and/or a device for measuring the length of the conduit.

The kit of parts may comprise a gas flow apparatus operable to provide gas flow to the conduit.

The gas may be air.

Embodiments of the third aspect of the invention may include one or more features of the first and/or second aspects of the invention and/or their embodiments. Similarly, embodiments of the first and/or second aspects of the invention may include one or more features of the third aspect of the invention and/or its embodiments.

According to a fourth aspect of the present invention, there is provided a method of manufacturing a vascular prosthesis according to the second aspect of the present invention.

Embodiments of the fourth aspect of the invention may include one or more features of the first, second and/or third aspects of the invention and/or their embodiments. Similarly, embodiments of the first, second and/or third aspects of the invention may include one or more features of the fourth aspect of the invention and/or its embodiments.

According to a fifth aspect of the present invention, there is provided a vascular prosthesis manufactured using the method of the first aspect of the present invention.

Embodiments of the fifth aspect of the invention may include one or more features of the first, second, third and/or fourth aspects of the invention and/or their embodiments. Similarly, embodiments of the first, second, third and/or fourth aspects of the invention may include one or more features of the fifth aspect of the invention and/or its embodiments.

According to a sixth aspect of the present invention, there is provided a vascular system, the vascular system comprising:

a vascular prosthesis manufactured according to the first aspect of the invention; and a further prosthesis;

wherein the vascular prosthesis is connected to the further prosthesis, such that fluid can flow between the vascular prosthesis and the further prosthesis.

The further prosthesis may be at least one of: a biological heart valve, a synthetic heart valve, a cardiac assist device, and a ventricular assist device, or the like.

The further prosthesis may be a left ventricular assist device, a right ventricular assist device, and/or a synthetic heart valve, or the like.

Embodiments of the sixth aspect of the invention may include one or more features of the first, second, third, fourth and/or fifth aspects of the invention and/or their embodiments. Similarly, embodiments of the first, second, third, fourth, and/or fifth aspects of the invention may include one or more features of the sixth aspect of the invention and/or its embodiments.

According to a seventh aspect of the present invention, there is provided a vascular system, the vascular system comprising:

a vascular prosthesis according to the second aspect of the invention; and a further prosthesis;

wherein the vascular prosthesis is connected to the further prosthesis, such that fluid can flow between the vascular prosthesis and the further prosthesis.

The further prosthesis may be at least one of: a biological heart valve, a synthetic heart valve, a cardiac assist device, and a ventricular assist device, or the like.

The further prosthesis may be a left ventricular assist device, a right ventricular assist device, and/or a synthetic heart valve, or the like.

Embodiments of the seventh aspect of the invention may include one or more features of the first, second, third, fourth, fifth and/or sixth aspects of the invention and/or their embodiments. Similarly, embodiments of the first, second, third, fourth, fifth and/or sixth aspects of the invention may include one or more features of the seventh aspect of the invention and/or its embodiments.

According to an eighth aspect of the invention there is provided a method of implanting a vascular prosthesis, the method comprising the steps of:

providing a vascular prosthesis manufactured according to the first aspect of the invention;

connecting an inlet of the vascular prosthesis to a first blood vessel; and connecting an outlet of the vascular prosthesis to a second blood vessel;

such that blood can flow between the first and second blood vessels through the vascular prosthesis.

The first and second blood vessels may be formed from a blood vessel which is diseased, or has been severed, bisected, or the like.

Embodiments of the eighth aspect of the invention may include one or more features of the first, second, third, fourth, fifth, sixth and/or seventh aspects of the invention and/or their embodiments. Similarly, embodiments of the first, second, third, fourth, fifth, sixth and/or seventh aspects of the invention may include one or more features of the eighth aspect of the invention and/or its embodiments.

According to a ninth aspect of the present invention, there is provided a method of implanting a vascular prosthesis, the method comprising the steps of:
providing a vascular prosthesis according to the second aspect of the invention;
connecting the vascular prosthesis to a first blood vessel; and
connecting the vascular prosthesis to a second blood vessel;
such that blood can flow between the first and second blood vessels through the vascular prosthesis.

The first and second blood vessels may be formed from a blood vessel which is diseased, or has been severed, bisected, or the like.

Embodiments of the ninth aspect of the invention may include one or more features of the first, second, third, fourth, fifth, sixth, seventh and/or eighth aspects of the invention and/or their embodiments. Similarly, embodiments of the first, second, third, fourth, fifth, sixth, seventh and/or eighth aspects of the invention may include one or more features of the ninth aspect of the invention and/or its embodiments.

According to a tenth aspect of the invention there is provided a method of implanting a vascular system, the method comprising the steps of:
providing a vascular system, the vascular system comprising:
a vascular prosthesis manufactured according to the first aspect of the invention; and
a further prosthesis;
wherein the vascular prosthesis is connectable to the further prosthesis;
connecting the vascular prosthesis to the further prosthesis, such that blood can flow therebetween;
connecting an end of a blood vessel to the vascular prosthesis; and
connecting the further prosthesis to the heart;
such that blood can flow between the blood vessel and the heart through the vascular system.

The further prosthesis may be a heart valve, a cardiac assist device, and/or a ventricular assist device, or the like. The further prosthesis may be a left ventricular assist device, a right ventricular assist device, and/or a synthetic heart valve, or the like.

Embodiments of the tenth aspect of the invention may include one or more features of the first, second, third, fourth, fifth, sixth, seventh, eighth and/or ninth aspects of the invention and/or their embodiments. Similarly, embodiments of the first, second, third, fourth, fifth, sixth, seventh, eighth and/or ninth aspects of the invention may include one or more features of the tenth aspect of the invention and/or its embodiments.

According to an eleventh aspect of the invention there is provided a method of implanting a vascular system, the method comprising the steps of:
providing a vascular system, the vascular system comprising:
a vascular prosthesis according to the second aspect of the invention; and
a further prosthesis;
wherein the vascular prosthesis is connectable to the further prosthesis;
connecting the vascular prosthesis to the further prosthesis, such that blood can flow therebetween;
connecting an end of a blood vessel to the vascular prosthesis; and
connecting the further prosthesis to the heart;
such that blood can flow between the blood vessel and the heart through the vascular system.

The further prosthesis may be at least one of: a biological heart valve, a synthetic heart valve, a cardiac assist device, and a ventricular assist device, or the like.

The further prosthesis may be a left ventricular assist device, a right ventricular assist device, and/or a synthetic heart valve, or the like.

Embodiments of the eleventh aspect of the invention may include one or more features of the first, second, third, fourth, fifth, sixth, seventh, eighth, ninth and/or tenth aspects of the invention and/or their embodiments. Similarly, embodiments of the first, second, third, fourth, fifth, sixth, seventh, eighth, ninth and/or tenth aspects of the invention may include one or more features of the eleventh aspect of the invention and/or its embodiments.

According to a twelfth aspect of the invention there is provided a method of manufacturing a vascular prosthesis, the method comprising the steps of:
(i) providing a conduit comprising a wall, the wall of the conduit comprising an inner surface and an outer surface, at least a section of the conduit being porous; and
(ii) adding a masking agent to at least a part of the porous section;
wherein the masking agent is configured to mitigate movement of fluid through the wall of the conduit.

Embodiments of the twelfth aspect of the invention may include one or more features of the first, second, third, fourth, fifth, sixth, seventh, eighth, ninth, tenth and/or eleventh aspects of the invention and/or their embodiments. Similarly, embodiments of the first, second, third, fourth, fifth, sixth, seventh, eighth, ninth, tenth and/or eleventh aspects of the invention may include one or more features of the twelfth aspect of the invention and/or its embodiments.

According to a thirteenth aspect of the invention there is provided a vascular prosthesis comprising:
a conduit comprising a wall, the wall of the conduit comprising an inner surface and an outer surface, at least a section of the conduit being porous;
wherein at least a part of the porous section comprises a masking agent configured to mitigate movement of fluid through the wall of the conduit.

Embodiments of the thirteenth aspect of the invention may include one or more features of the first, second, third, fourth, fifth, sixth, seventh, eighth, ninth, tenth, eleventh and/or twelfth aspects of the invention and/or their embodiments. Similarly, embodiments of the first, second, third, fourth, fifth, sixth, seventh, eighth, ninth, tenth, eleventh and/or twelfth aspects of the invention may include one or more features of the thirteenth aspect of the invention and/or its embodiments.

In another aspect or embodiment, a method of manufacturing a tubular graft may comprise the steps of: providing a textile comprising a tubular wall disposed between a first open end and an opposed second open end, an inner surface and an opposed outer surface defining an interior wall portion therein between, the tubular wall comprising a textile construction of one or more filaments or yarns, the textile construction by itself being permeable to liquid; applying a substantially water-soluble material to at least a portion of the tubular wall; and applying a substantially water-insoluble synthetic sealant to at least a part of the outer surface of the tubular wall, the substantially water-insoluble synthetic sealant being configured to mitigate movement of fluid through the wall of the conduit; wherein the water-soluble material is configured to mitigate penetration of the sealant to the inner surface of the conduit.

The step of applying the water-soluble material to at least a portion of the tubular wall may further comprise applying the water-soluble material to at least a portion of the inner surface and a portion of the interior portion of the tubular wall. The step of applying the water-soluble material to at least a portion of the tubular wall may further comprise applying the water-soluble material to at least a portion of the outer surface of the tubular wall.

The water-soluble material may be a solution of the water-soluble material and a solvent. The solvent may be selected form the group consisting of water, lower alcohols, and combinations thereof. The solvent may be at least partially removed prior to applying the substantially water-insoluble synthetic sealant.

The method may further comprise removal of at least a portion of the water-soluble material by dissolution, abrading, peeling, degrading, and combinations thereof.

The water-soluble material may be selected from the group consisting of polyvinylpyrrolidone, glycerol, methyl cellulose, poly(ethylene glycol), poly(ethylene glycol) hydrogel, polyethylene oxide, collagen, albumin, gelatin, and combinations thereof. The water-soluble material may have a molecular weight from about 400 to about 1,000,000. The water-soluble material may include plasticizers, such as but not limited to poly(ethylene glycol), polyethylene oxide, and the like.

The substantially water-insoluble synthetic sealant may be an elastomeric material selected from the group consisting of moisture curing, light curing, thermo-curing, platinum catalysed, anaerobic curing materials or a combination of these curing mechanisms. The elastomeric material may be selected from the group consisting of silicones, polyurethanes, polycarbonates, thermoplastic elastomers, and combinations thereof.

The one of more of the substantially water-soluble coating or the substantially water-insoluble coating may further comprise a component selected from the group consisting of a colorant, a therapeutic agent, a dye, and a fluorescent indicator.

The water-soluble material may comprise polyvinylpyrrolidone having a molecular weight of between approximately 6,000 g/mol and approximately 15,000 g/mol.

The applying the water-soluble material may form layer on substantially all of the inner surface of the tubular wall.

The method may further comprise curing the substantially water-insoluble synthetic sealant.

The method may further comprise curing the substantially water-insoluble synthetic sealant; and thereafter removing at least a portion of the water-soluble material. The method may further comprise removing substantially all of the water-soluble material from the inner surface of the tubular wall.

The method may further comprise: removing at least a part of the water-soluble material from at least a part of the outer surface of the tubular wall prior to the applying the substantially water-insoluble synthetic sealant.

The removing of at least the portion of the water-soluble material may be carried out at a temperature of between approximately 15° C. and approximately 140° C.

The removing at least the portion of the water-soluble material may further comprise the step of applying a solvent thereto. The solvent may comprise water, lower alcohols, and combinations thereof.

The tubular textile may be agitated, rotated, spun, and shaken, or the like, during the removal of the water-soluble material.

The removal of the water-soluble material may comprises dissolving, etching, plasma etching, ablating, abrading and combinations thereof of the water-soluble material.

The step of applying the water-soluble material may further comprise spraying the water-soluble material, brushing the water-soluble material, immersing at least a portion of the tubular wall into a solution of the water-soluble material, and combinations thereof.

The substantially water-insoluble synthetic sealant may be a polymer solution. The polymer solution may comprise an organic solvent. The organic solvent may comprise at least one of heptane and xylene.

The substantially water-insoluble synthetic sealant may be applied by brushing, spraying, roller coating the substantially water-insoluble synthetic sealant thereon.

The may further comprise one or more steps of selectively applying the substantially water-insoluble synthetic sealant to one or more portions of the tubular wall, such that the tubular wall comprises at least two sections having substantially different amounts of the substantially water-insoluble synthetic sealant thereon.

The tubular wall having the coating of the substantially water-insoluble synthetic sealant may be, after curing thereof, substantially impermeable to liquid. After curing of the substantially water-insoluble synthetic sealant, the tubular wall may have a water permeability of about 0.16 ml/min/cm$^2$ at 120 mm Hg pressure or less than 0.16 ml/min/cm$^2$ at 120 mm Hg pressure.

In another aspect or embodiment, a textile may comprise: a tubular wall disposed between a first open end and an opposed second open end and having an inner surface and an opposed outer surface, the tubular wall comprising a textile construction of one or more filaments or yarns, the textile construction by itself being permeable to liquid; wherein a portion of the inner surface comprises a coating of a substantially water-soluble material thereon; wherein the outer surface further comprises a coating of a substantially water-insoluble synthetic sealant disposed thereon; and wherein the tubular wall having the coating of the substantially water-insoluble synthetic sealant is, after curing thereof, substantially impermeable to liquid.

The water-soluble material may be selected from the group consisting of polyvinylpyrrolidone, glycerol, methyl cellulose, poly(ethylene glycol), poly(ethylene glycol) hydrogel, polyethylene oxide, and combinations thereof. The water-soluble material may have a molecular weight from about 400 to about 1,000,000.

The coating of the water-soluble material may comprise an oleophobic layer.

The water-soluble material may comprise polyvinylpyrrolidone having a molecular weight of between approximately 6,000 g/mol and approximately 15,000 g/mol.

The water-soluble material may comprise polyvinylpyrrolidone and glycerol.

The substantially water-insoluble synthetic sealant may be an elastomeric material selected from the group consisting of moisture curing, light curing, thermo-curing, platinum catalyzed, anaerobic curing materials or a combination of these curing mechanisms. The elastomeric material may be selected from the group consisting of silicones, polyurethanes, polycarbonates, thermoplastic elastomers, and combinations thereof.

One of more of the substantially water-soluble coating or the substantially water-insoluble coating may comprise a component selected from the group consisting of a colorant, a therapeutic agent, a dye, and a fluorescent indicator.

After curing of the substantially water-insoluble synthetic sealant, the tubular wall may have a water permeability of about 0.16 ml/min/cm$^2$ at 120 mm Hg pressure or less than 0.16 ml/min/cm$^2$ at 120 mm Hg pressure.

The textile construction may be selected from the group consisting of a weave of the one or more filaments or yarns, a knit of the one or more filaments or yarns, a braid of the one or more filaments or yarns, and a web of the one or more filaments or yarns.

The tubular wall may be a crimped wall having a series of peaks and valleys. The substantially water-insoluble synthetic sealant may be disposed at about 8 mg/cm$^2$ of area of the tubular wall or greater than 8 mg/cm$^2$ of area of the tubular wall.

The tubular wall may be a non-crimped wall being substantially free of peaks and valleys. The substantially water-insoluble synthetic sealant may be disposed at about 4 mg/cm$^2$ of area of the tubular wall or greater than 4 mg/cm$^2$ of area of the tubular wall.

The substantially water-insoluble synthetic sealant may be disposed at about 14 mg/cm$^2$ of area of the tubular wall or less than 14 mg/cm$^2$ of area of the tubular wall.

The textile may include one portion of the tubular wall has a first level of the substantially water-insoluble synthetic sealant to provide a first soft, flexible zone; and another portion of the tubular wall has a second level of the substantially water-insoluble synthetic sealant to provide a second zone stiffer than the first zone; where the second level the substantially water-insoluble synthetic sealant is greater than the first level of the substantially water-insoluble synthetic sealant.

Different zones may be created along the length of the device (e.g. prosthesis or graft) and engineered to accommodate a variety of applications and body architecture. For example, a particular need may exist for the device to be turned, curved or twisted in order to properly perform its function in the body, as well as to the physiology of the patient. Tortuous pathways are often present in the body and the medical devices of the present invention are able to accommodate for such areas. The present disclosure and all of its embodiments allow for the creation of such zones by the creation of one or more sealant layers on all of, or at portions of, the graft, and also by the incorporation of support members as described further herein, which as discussed may be adhered to or embedded in the sealant material. As discussed, the support members may be polymeric or metallic and may be in a variety of forms such as elongate members, coils, wraps, rings or a combination of such forms. An important feature of all embodiments of the invention is that the sealant material is capable of serving as a foundational layer for further coatings or for support members due to the excellent adherence of the base sealant layer to its graft substrate.

Additionally, the present invention and its various embodiments contemplates the tailoring of the sealant surface such that its coefficient of friction may be varied and desirably sufficiently low such that the sealant does not stick to itself and/or sufficiently low enough that when used in devices such as endovascular devices, has sufficient lubricity to facilitate delivery and deployment in the body, For example, the sealant surface desirably slides into delivery sheaths, slides across itself and does not stick to itself, to other portions of the device, other devices or the body. Such surface properties may be imparted by altering the sealant surface chemically or physically with lubricous groups or coatings to provide the desired coefficient of friction properties desired. Such surface properties may be in addition to the other properties the sealant possesses in the present invention.

At least a portion of the coating of the substantially water-insoluble synthetic sealant may engage at least a portion of the one or more filaments or yarns.

The textile structure may be an implantable medical device. The implantable medical device may be selected from the group consisting of surgical vascular grafts, and endovascular grafts, ventricular assist devices, artificial heart conduits, meshes, patches, hernia plugs, vascular wraps, heart valves, filters, and the like.

The textile structure may be a delivery medical device, such as a catheter.

In another embodiment, a textile structure may comprise: a fluid permeable polymeric textile layer having opposing first and second surfaces and a length; a cross-linkable water-insoluble synthetic elastomeric layer on the first textile surface configured to render the liquid permeable polymeric textile layer substantially impermeable to fluid when cured; a substantially dried water-soluble polymer layer on the second textile surface; wherein water-soluble polymer layer substantially inhibits migration of the water-insoluble synthetic elastomeric layer onto the second surface; and wherein the water-soluble polymer layer is substantially removable by exposure to water.

In another embodiment, a textile structure may comprise: a fluid permeable polymeric textile layer having opposing first and second surfaces and a length; a cross-linkable water-insoluble synthetic elastomeric layer on the first textile surface configured to render the liquid permeable polymeric textile layer substantially impermeable to fluid when cured; a substantially dried water-soluble polymer layer on the second textile surface; wherein water-soluble polymer layer substantially inhibits migration of the water-insoluble synthetic elastomeric layer onto the second surface; and wherein the water-soluble polymer layer is substantially removable by exposure to water. The weight ratio of the cross-linkable water-insoluble elastomeric polymer to the water-soluble polymer may be from about 0.1:1 to about 100:1, including from about 1:1 to about 20:1.

In another embodiment, a textile structure may comprise: a fluid permeable polymeric textile layer having opposing first and second surfaces and a length; a crosslinked water-insoluble elastomeric polymer layer on the first textile surface forming a substantially fluid impermeable barrier, wherein the crosslinked water-insoluble elastomeric layer is adhered to the first textile surface by elastomeric shrinkage; a water dissolvable polymer layer dried on the second textile surface; wherein the weight ratio of the crosslinked water-insoluble elastomeric polymer to the water dissolvable polymer may be from about 0.1:1 to about 100:1. The weight ratio of the crosslinked water-insoluble elastomeric polymer to the water dissolvable polymer may be from about 1:1 to about 20:1.

In another embodiment, a graft may comprise: a tubular wall disposed between a first open end and an opposed second open end and having an inner surface and an opposed outer surface, the tubular wall comprising a textile construction of one or more filaments or yarns; wherein the outer surface comprises a coating or layer of a substantially water-insoluble sealant disposed thereon; wherein the inner surface is substantially free of the substantially water-insoluble sealant; and wherein the tubular wall has a water permeability of about 0.16 ml/min/cm$^2$ at 120 mm Hg pressure or less than 0.16 ml/min/cm$^2$ at 120 mm Hg pressure. The textile construction may be selected from the group consisting of a weave of the one or more filaments or yarns, a knit of the one or more filaments or yarns, a braid of the one or more filaments or yarns, and a web of the one or more filaments or yarns.

The coating or layer may be disposed within an intermediate portion of the tubular wall between the inner surface and the opposed outer surface.

The tubular wall may be a crimped wall having a series of peaks and valleys. The substantially water-insoluble sealant may be disposed at about 8 mg/cm$^2$ of area of the tubular wall or greater than 8 mg/cm$^2$ of area of the tubular wall.

The tubular wall may be a non-crimped wall being substantially free of peaks and valleys. The substantially water-insoluble sealant may be disposed at about 4 mg/cm$^2$ of area of the tubular wall or greater than 4 mg/cm$^2$ of area of the tubular wall.

The substantially water-insoluble sealant may be disposed at about 14 mg/cm$^2$ of area of the tubular wall or less than 14 mg/cm$^2$ of area of the tubular wall.

The substantially water-insoluble sealant may be an elastomeric material selected from the group consisting of moisture curing, light curing, thermo-curing, platinum catalyzed, anaerobic curing materials or a combination of these curing mechanisms. The elastomeric material may be selected from the group consisting of silicones, polyurethanes, polycarbonates, thermoplastic elastomers, and combinations thereof.

One of more of the substantially water-soluble coating (masking agent coating or layer) or the substantially water-insoluble coating (sealant coating or layer) may comprise a component selected from the group consisting of a colorant, a therapeutic agent, a dye, and a fluorescent indicator.

The substantially water-insoluble sealant (sealant coating or layer) may be selected from the group consisting of silicone, room temperature vulcanizing silicone, thermoplastic polyurethane, aliphatic polycarbonate, one or more thermoplastic elastomers, polycarbonate, and combinations thereof.

The graft may include one portion of the tubular wall having a first amount of the substantially water-insoluble sealant (sealant coating or layer) to provide a first soft, flexible zone; and another portion of the tubular wall having a second amount of the substantially water-insoluble sealant (sealant coating or layer) to provide a second zone stiffer than the first zone; wherein the second amount of the substantially water-insoluble sealant (sealant coating or layer) is greater than the first amount of the substantially water-insoluble sealant (sealant coating or layer). The graft may include multiple regions having pluralities of soft, flexible zones and stiffer zones. The different zones may serve as foundations for building engineered structures onto a graft.

In another embodiment, an implantable or deliverable medical textile may comprise: a wall having a textile construction and having a first surface and an opposed second surface; wherein the second surface comprises a coating of a substantially water-insoluble sealant disposed thereon; wherein the first surface is substantially free of the substantially water-insoluble sealant; and wherein the wall has a water permeability of about 0.16 ml/min/cm$^2$ at 120 mm Hg pressure or less than 0.16 ml/min/cm$^2$ at 120 mm Hg pressure.

An assembly for producing an implantable or deliverable medical textile having a selectively applied water-insoluble sealant layer and/or a selectively applied water-soluble masking agent layer comprises a mandrel having a length, a hollow lumen disposed within a portion of the length, at least one open end, and a plurality of perforations through a wall of the mandrel; a reservoir in fluid communication with the open lumen of the mandrel; and a water-soluble polymer disposed within the reservoir. The assembly may further comprise a tubular graft securably disposed over a portion of the mandrel having the plurality of perforations. The assembly may further comprise a vacuum source in fluid communication with the hollow lumen of the mandrel, and a manifold configured to provide selective fluid communication between the hollow lumen of the mandrel and the reservoir and/or the vacuum source. The assembly may further comprise a source of pressurized and/or blown air which is in fluid communication with the hollow lumen of the mandrel.

Embodiments of the present invention, however, are not limited to vascular prostheses, and the methods, coatings and masking agents may suitably be used with other textile products, including medical and non-medical textile products, such as but not limited to clothing, geotextiles, transportation textiles, military and/or defense textiles, safety and/or protective textiles, sports and/or recreation textiles, and the like. Further, textile products are not limited to tubular conduits, but may be of any shape including, but not limited to for example, sheets, tapes, or even three dimensional shaped products.

Embodiments of the various aspects of the invention as recited herein may include one or more features of other aspects of the invention and/or their embodiments.

BRIEF DESCRIPTION OF THE DRAWINGS

Embodiments of the invention will now be described, by way of example, with reference to the drawings, in which:

FIGS. 2a and 2b show shows a detailed view of an inner surface of a wall of the conduit of FIG. 1a;

FIG. 7 depicts the addition of a support member to the conduit shown depicted in FIG. 1a;

DESCRIPTION OF EMBODIMENTS

As used herein the term "substantially" and its equivalents refer to being at least 70% of a stated value, desirably within at least 80% of a stated value, and more desirably within 90% or 95% of a stated value.

As used herein the terms "about" or "approximate" and their equivalents refer to being within (plus and/or minus) at least 20% of a stated value, desirably within at least 10% of a stated value, and more desirably within 5% of a stated value.

As used herein the terms "layer" and "coating" may be used interchangeably to refer to a deposition of material over, underneath, or within a substrate, such as a textile substrate.

As used herein masking agent shall refer to any suitable non-biological, e.g., synthetic, hydrophilic polymer and any suitable biological hydrophilic polymer. However, it should be understood that other masking agents may be used.

With reference to FIGS. 1a to 1d, four stages of manufacture of a vascular prosthesis 16 are illustrated. In each of the FIGS. 1a to 1d two perspective views of the conduit 10 and/or the vascular prosthesis 16 are provided. The left hand views show an inlet 10c being forwardly disposed in the views, and the right hand views show an outlet 10d being forwardly disposed in the views.

Figure 1A:
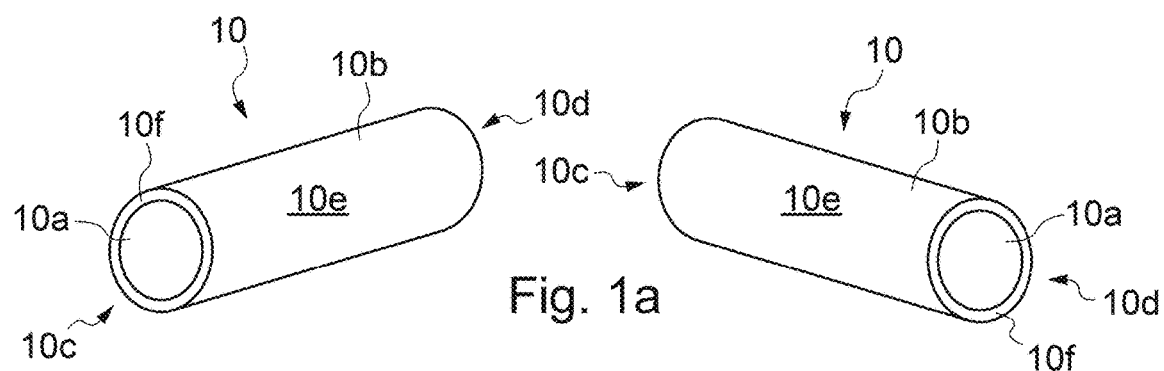
FIG. 1a depicts perspective views of a conduit from both inlet and outlet perspectives according to an embodiment of the invention.

FIG. 1a shows a conduit 10 which is suitable for implant in the human or animal body. The conduit 10 is a cylindrical conduit 10 and comprises a wall 10f. The wall 10f comprises an inner surface 10a and an outer surface 10b. The conduit 10 also comprises an inlet 10c and an outlet 10d. In the embodiment described here, substantially all of the conduit 10 is porous 10e. However, it should be understood that at least a section of the conduit 10 could be porous 10e. In this embodiment, the conduit 10 is a woven, fibrous polymer conduit 10. The woven nature of the conduit 10 leads to substantially all of the conduit 10 being porous 10e.

The conduit 10 comprises polyethylene terephthalate (PET). However, it should be understood that the conduit 10 could comprise other materials, such as polytetrafluoroethylene (PTFE). Other suitable polymers for medical textile applications may include, but are not limited to polyolefin, polyester, poly(ether amide), poly(ether ester), poly(ether urethane), poly(ester urethane), poly(ethylene-styrene/butylene-styrene), and other block copolymers.

In the embodiment illustrated and described here, the weft yarn pick-rate of the conduit 10 is approximately 45 ppcm. However, it should be understood that the weft yarn pick-rate of the conduit 10 could be between approximately 25 ppcm and approximately 50 ppcm.

The conduit 10 is moveable between a contracted state and an extended state.

FIG. 1a thus depicts an unprocessed conduit 10. In its unprocessed form, blood (an example of a fluid) can flow between the outer surface 10b of the wall 10f and the inner surface 10a of the wall 10f. That is, if fluid flows into the inlet 10c, the blood will leak through the porous section 10e of the conduit 10. The conduit 10 depicted in FIG. 1a must therefore be sealed prior to use as an implantable vascular prosthesis 16.

The conduit 10 depicted in FIG. 1a has been cut to a predetermined size. For example, the length of the conduit 10 may need to be altered depending on the size of vascular prosthesis 16 required. Furthermore, if the vascular prosthesis 16 is to be connected to at least one heart assist component (an example of a further prosthesis), this may also require a different size, or length of conduit 10 to be used. The conduit 10 is also weighed during this step of the manufacturing process.

In the embodiment illustrated here, the conduit 10 has a substantially uniform cross section throughout. However, it should be understood that the conduit 10 could have an irregular cross section throughout. For example, if the conduit 10 is to be connected between a further prosthesis, such as a heart valve, and an end of a severed blood vessel, the conduit 10 could have an irregular cross section throughout. As described in more detail below, in some embodiments the conduit 10 could be configured to have differing degrees of flexibility, either by selectively adding sealant 14 to different sections of the conduit 10, or in other ways.

As described above, it is desirable for the inner surface 10a of the wall 10f of the conduit 10 to remain free from, or substantially devoid of, the material used to seal the conduit 10. The reason for this is to ensure that the inner surface 10a of the wall 10f of the conduit 10, remains of a porous 10e, woven nature, to ensure that when the vascular prosthesis 16 is implanted in the human or animal body, biological tissue will grow into the inner surface 10a of the wall 10f of the conduit 10. This is important to ensure that ingrowing biological tissue forms a pseudointima (an example of an inner biological tissue layer within a vascular prosthesis). Furthermore, in addition to the promotion of biological tissue growth on the inner surface 10a of the wall 10f of the conduit 10, it is also advantageous if the biological tissue layer growing on the inner surface 10a of the wall 10f of the conduit 10 has good adhesion to the inner surface 10a. If the adhesion between the biological tissue layer and the inner surface 10a is insufficient, complications can arise such as haemorrhagic dissection.

Figure 1B:
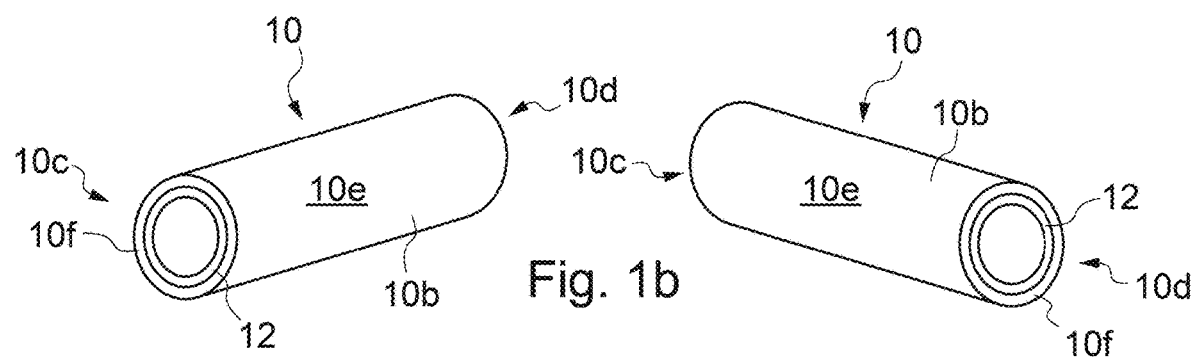
FIG. 1b depicts perspective views of the conduit of FIG. 1a after the addition of a masking agent.

FIG. 1b shows the conduit 10 after the addition of a masking agent 12. In this embodiment, the masking agent 12 forms a masking agent layer on the inner surface 10a of the wall 10f of the conduit 10. The masking agent layer is designed to protect the inner surface 10a of the conduit 10 during the manufacturing process illustrated and described herein. Specifically, the masking agent 12 is designed to mitigate presence of sealant 14 on the inner surface 10a of the wall 10f of the conduit 10.

Prior to the addition of the masking agent 12 to the conduit 10, the conduit 10 is weighed. The weight of the conduit 10 is then used, at least in part, to determine the amount of masking agent 12 to add to the conduit 10.

In this embodiment, the masking agent 12 is applied from a masking agent solution. The masking agent solution is a polymer solution. In the embodiment illustrated and described here, the polymer solution comprises approximately 7% w/v PVP (an example of a water-soluble polymer) in water (an example of a solvent). However, it should be understood that other polymers, such as glycerol, methyl cellulose and/or PEG could be used. Furthermore, it will be understood that the polymer solution could comprise between approximately 5% w/v PVP in solution and approximately 30% w/v PVP in solution. Moreover, the polymer solution could comprise between approximately 5% w/v polymer in solution and approximately 30% w/v polymer in solution. It should be understood that the masking agent 12 could comprise approximately 1% w/v of glycerol in solution. Without wishing to be bound by theory, it is thought that an advantage of adding glycerol to the masking agent 12 is that it mitigates cracking of the masking agent 12 when the masking agent 12 is added to the conduit 10.

In the embodiment described here, the masking agent 12 comprises PVP with a molecular weight of approximately 10,000 g/mol. However, it should be understood that the masking agent 12 could comprise PVP with a molecular weight of between approximately 6,000 g/mol and approximately 15,000 g/mol.

While in the embodiment described here the masking agent 12 comprises PVP, it should be understood that the masking agent 12 could comprise glycerol, methyl cellulose, PEG, PEO, and/or PEG hydrogel.

In the embodiment illustrated and described here, the masking agent 12 is biocompatible. However, it should be understood that, in some embodiments the masking agent 12 need not be biocompatible. For example, as described in more detail below, if substantially all of the masking agent 12 is to be removed from the conduit 10, then the masking agent 12 need not be biocompatible. In some embodiments, the masking agent 12 need not be removed, and in some embodiments only a part of the masking agent 12 is removed. In these arrangements, it is advantageous that the masking agent 12 is biocompatible, which allows the conduit 10 to be implanted in the human or animal body.

In this embodiment, the masking agent 12 is biodegradable. Therefore, any residual masking agent 12 present on the conduit 10 will biodegrade when the conduit 10 is implanted in the human or animal body. However, the masking agent 12 could be non-biodegradable. In this embodiment, substantially all of the masking agent 12 is removed from the conduit 10 prior to implantation, and therefore it is not necessary for the masking agent 12 to be biodegradable. In some embodiments, it may be advantageous for the masking agent 12 to be biodegradable.

With reference to FIG. 1b, the masking agent 12 is applied to the conduit 10 from a polymer solution. However, it will be appreciated that the masking agent 12 could be applied to the conduit 10 in other ways.

In this embodiment, the masking agent solution is applied to the conduit 10 by immersing the conduit 10 in the masking agent solution for approximately 1 minute, while agitating the conduit 10. However, it should be understood that the masking agent solution could be added to the conduit 10 in other ways, such as by dipping, spray coating, or by brushing. Furthermore, it should be understood that the masking agent 12 could be added to the conduit 10 without agitating the conduit 10. During the step of immersing the conduit 10 in the masking agent solution, the conduit 10 is moved between the contracted state and the extended state. However, it should be understood that the conduit 10 could be immersed in the masking agent solution while the conduit 10 is in the contracted state and/or the extended state.

In this embodiment, when the masking agent solution is added to the conduit 10, solvent is then evaporated from the masking agent solution. Solvent is therefore removed from the masking agent solution, and the masking agent 12 remains on the conduit 10.

In this embodiment, during the addition of the masking agent 12 to the conduit 10, a directed flow of air (an example of a gas) is provided to the conduit 10. The directed flow of air is directed towards the outer surface 10b of the wall 10f of the conduit 10, such that the masking agent 12 is preferentially formed on the inner surface 10a of the wall 10f of the conduit 10. It should be understood that while directed air flow is used here, other gases could be used.

In this embodiment, the masking agent 12 is formed, or added, substantially on the inner surface 10a of the wall 10f of the conduit 10. However, it should be understood that the masking agent 12 could be added to the outer surface 10b of the wall 10f of the conduit 10. The masking agent 12 is added to the porous section 10e of the conduit 10, although in other embodiments the masking agent 12 could be added to at least a part of the porous section 10e of the conduit 10. In this embodiment, the masking agent 12 forms a masking agent layer substantially on the inner surface 10a of the wall 10f of the conduit 10. However, it should be understood that the masking agent 12 could be added to other parts of the conduit 10, and that the masking agent 12 could form a masking agent layer on other parts of the conduit 10.

In the manufacturing process illustrated and described here, the residual masking agent 12 on the outer surface 10b of the wall 10f of the conduit 10 is removed prior to the addition of the sealant 14, in order to improve the adhesion between the sealant 14 (when applied to the conduit 10) and the outer surface 10b of the wall 10f of the conduit 10. In this embodiment, the residual masking agent 12 on the outer surface 10b is removed by ablating (an example of a first masking agent removal step). However, it should be understood that the masking agent 12 could be removed by applying a solvent, by heating, by etching, by plasma etching, by abrading, and/or by other techniques.

In the embodiment shown in FIG. 1b, the masking agent 12 is formed on substantially all of the inner surface 10a of the wall 10f of the conduit 10.

Figure 1C:
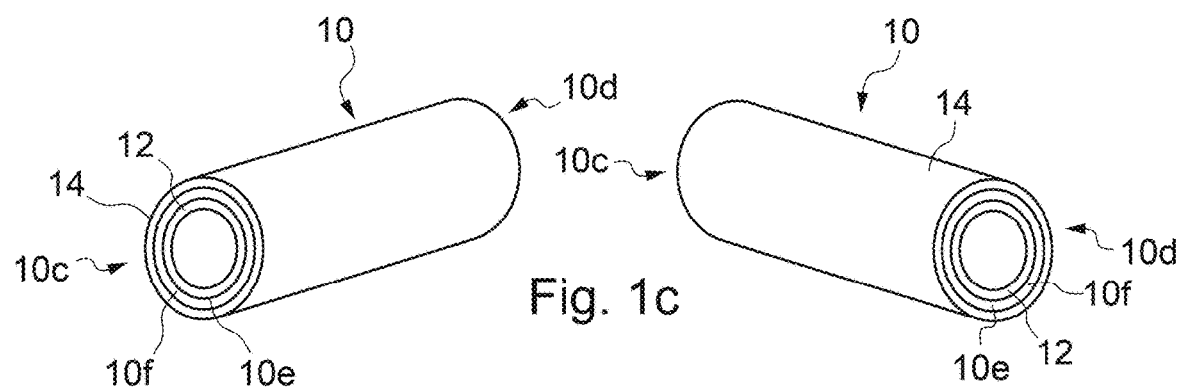
FIG. 1c depicts perspective views of the conduit of FIG. 1b after the addition of a sealant.

FIG. 1c shows the conduit 10 after the addition of the masking agent 12 and the sealant 14. In the embodiment described here, the sealant 14 is added to the conduit 10 from a sealant solution. In the embodiment described here, the sealant solution is a polymer solution comprising room temperature vulcanising silicone elastomer and xylene. However, it should be understood that the sealant solution could comprise at least one of polycarbonate, silicone, silicone elastomer, polyurethane, TPU, one or more thermoplastic elastomers, and/or aliphatic polycarbonate. It should also be understood that while the sealant 14 is added to the conduit 10 from a polymer solution comprising xylene, heptane could be used in place of xylene. Furthermore, in some embodiments the sealant solution may comprise a polar solvent, such as dimethylacetamide (DMAC) or tetrahydrofuran (THF).

When the sealant solution is applied to the conduit 10, solvent is evaporated from the sealant solution, which results in the formation of the sealant 14.

While in the embodiment illustrated and described here the sealant 14 is added to the conduit 10 from a sealant solution, it will be understood that the sealant 14 could be added to the conduit 10 in other ways and need not be added from a sealant solution.

The sealant 14 is added to the porous section 10e of the conduit 10. Therefore, in this embodiment, the sealant 14 is added to substantially all of the conduit 10, as in this embodiment the conduit 10 is entirely porous 10e. In other embodiments, the sealant 14 could be added to a part of the porous section 10e.

The presence of the masking agent 12 prevents the sealant 14 from adhering, or forming on, the inner surface 10a of the wall 10f of the conduit 10. The sealant 14 is applied to the conduit 10 by spraying the sealant 14 onto the outer section 10b of the conduit 10. However, it should be understood that other techniques for adding the sealant 14 to the conduit 10 could be used, such as brushing, wiping, immersing, dipping, vapour depositing, such as chemical vapour depositing, electrostatic spinning, and/or by casting.

In this embodiment, the sealant 14 is applied to the conduit 10, while the conduit 10 is in the extended state. However, it should be understood that the sealant 14 could be applied to the conduit 10 while the conduit 10 is in the contracted state or when the conduit 10 is moved between the contracted state and the extended state.

In this embodiment, the sealant 14 is added to the conduit 10 while the conduit 10 is rotated about its longitudinal axis at approximately 60 rpm. However, it should be understood that the conduit 10 could be rotated about its longitudinal axis at up to approximately 2,000 rpm.

In the embodiment described here, the sealant 14 comprises approximately 8 mg/cm$^2$ of silicone. However, it should be understood that the sealant could comprise between approximately 4 mg/cm$^2$ of silicone and approximately 19 mg/cm$^2$ of silicone.

Spraying and/or brushing the sealant 14 onto the outer surface 10b of the wall 10f of the conduit 10 is advantageous over some sealant application techniques because the sealant 14 is applied substantially only to the outer surface 10b of the conduit 10 and is not substantially applied to the inner surface 10a of the conduit 10. In this arrangement, the masking agent 12, and the addition of the sealant 14 to the conduit 10 by way of spraying, and/or brushing, the sealant 14 onto the conduit 10, mitigate presence of the sealant 14 on the inner surface 10a of the wall 10f of the conduit 10. However, it should be understood that other sealant 14 application techniques, such as wiping the sealant 14 onto the conduit 10, could be used.

In the embodiment illustrated and described here, it is advantageous if, when the sealant 14 is applied to the conduit 10, the masking agent 12 is not substantially covered, or blocked, by the sealant 14. The reason for this is that, if at least a part of the masking agent 12 is to be removed from the conduit 10, it is easier to remove the masking agent 12 if at least some of the masking agent 12 is exposed. For example, when removing at least a part of the masking agent 12 from the conduit 10 by applying a solvent, it is easier to do so if at least some of the masking agent 12 is exposed. In the embodiments described here, a significant amount of the masking agent 12 is exposed, and it is therefore relatively straightforward to use a variety of masking agent 12 removal techniques.

In this embodiment, the addition of the sealant 14 to the porous section 10e of the conduit 10 forms a sealing layer on the outer surface 10b of the wall 10f of the conduit 10. In this embodiment, the sealant 14 is biocompatible.

In this embodiment, the sealant 14, when applied to the conduit 10, is configured to mitigate against environmental stress cracking.

Figure 1D:
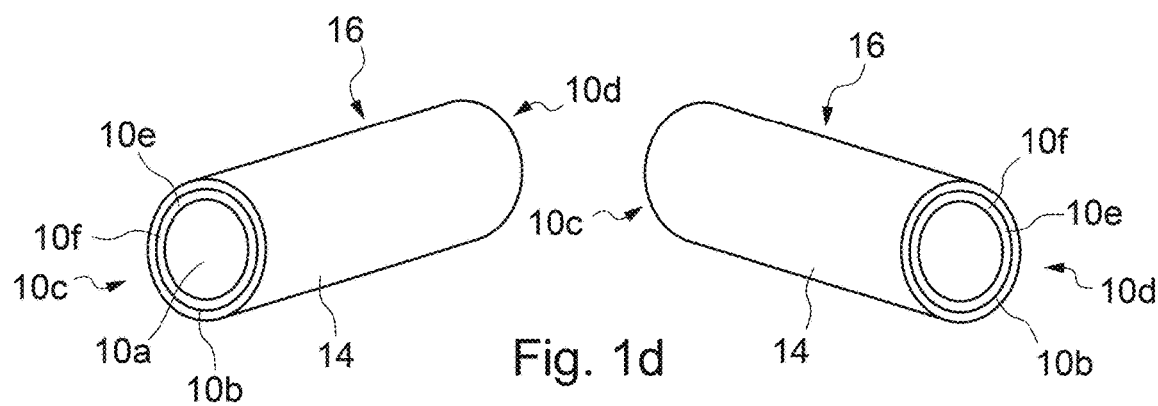
FIG. 1d depicts perspective views of the conduit of FIG. 1c after removal of substantially all of the masking agent.

FIG. 1d shows a vascular graft 16 (an example of a vascular prosthesis 16). In this embodiment, substantially all of the masking agent 12 has been removed from the conduit 10. The leaking of blood (an example of a fluid) through the wall 10f of the conduit 10 is now mitigated due to the addition of the sealant 14 to the conduit 10. Furthermore, the inner surface 10a of the wall 10f of the conduit 10 retains the porous, woven properties of the conduit 10, such that the inner surface 10a of the wall 10f of the conduit 10 allows for the ingrowth of biological tissue and also allows for biological tissue to have good adhesion thereto. The presence of the sealant 14 obviates the flow of blood through the wall 10f of the conduit 10, although it will be understood that blood can flow between the inlet 10c and the outlet 10d.

In the embodiment described here and shown in FIG. 1d, substantially all of the masking agent 12 has been removed from the conduit 10 by applying water to the conduit 10 at a temperature of approximately 95° C. (an example of a second masking agent removal step). In this second masking agent removal step, the masking agent 12 has been removed from the conduit 10 after the step of adding the sealant 14 to the conduit 10 has been carried out. In this process, water (an example of a solvent) has been used to remove substantially all of the masking agent 12 from the conduit 10. However, the masking agent 12 need not be removed substantially entirely from the conduit 10. Water need not be used as the solvent, as other solvents could be used to achieve the removal of the masking agent 12. It should be understood that the masking agent 12 could be removed from the conduit 10 in other ways, such as by etching, plasma etching, ablating, and/or abrading. While the masking agent 12 has been substantially removed from the conduit 10 at a temperature of approximately 95° C., it should be understood that the masking agent 12 could be removed from the conduit 10 at a temperature of between approximately 15° C. and approximately 140° C. In the embodiment described here, the step of removing the masking agent 12 from the conduit 10 is also used to cure the sealant 14 in a more efficient manner.

In the embodiment depicted in FIG. 1d, the masking agent removal step, carried out as described above, is carried out for approximately 51 minutes while the conduit 10 is agitated. Without wishing to be bound by theory, agitating the conduit 10 is thought to improve the efficiency of the masking agent 12 removal step. Whilst in this embodiment the masking agent removal step is carried out for approximately 51 minutes, it will be understood that the masking agent removal step could be carried out for between approximately 40 minutes and approximately 300 minutes. It will also be understood that multiple masking agent removal steps could be carried out.

In the embodiment illustrated and described here, the step of removing substantially all of the masking agent 12 from the conduit 10 does not result in the removal of the sealant 14 from the conduit 10.

As described in detail above, the manufacturing process comprises a first masking agent removal step, designed to improve the adhesion of the sealant 14 to the conduit 10, and a second masking agent removal step, designed primarily to remove the masking agent 12 from the inner surface 10a of the wall 10f of the conduit 10. However, it will be understood that multiple masking agent removal steps could be carried out. It should also be understood that for some embodiments of the invention it may not be necessary to carry out a masking agent removal step.

In the embodiment illustrated and described here, the vascular prosthesis 16 is reversibly sealable. That is, the sealant 14 could be removed from the conduit 10 and the sealant 14 could be applied to the conduit 10. For example, this could be necessary in the event of a manufacturing error. Similarly, the masking agent 12 may be added, and removed from, and subsequently added to the conduit 10. This could be necessary when carrying out more than one masking agent addition step.

In the embodiment illustrated and described here, the vascular prosthesis 16 can be sterilised by way of a gamma sterilisation process. However, it should be understood that the vascular prosthesis 16 could be sterilised by way of an electron beam sterilisation process. Another option for sterilising the vascular prosthesis 16 is to carry out ethylene oxide sterilisation. It will be appreciated that other sterilisation techniques could be applied to the vascular graft 16, either as an alternative to, or in addition to those described here.

The vascular prosthesis 16 depicted in FIG. 1d is configured to be implantable inside the human or animal body and is made from substantially entirely biocompatible materials. The vascular prosthesis 16 can be implanted in the human or animal body without being harmful or toxic to surrounding biological tissue.

The vascular prosthesis 16 illustrated in FIG. 1d is flexible, which allows the vascular prosthesis 16 to be manipulated by a medical practitioner in a more efficient way. In this embodiment, the addition of the sealant 14 to substantially all of the porous section 10e of the conduit 10 has converted the unprocessed conduit 10 to a vascular prosthesis 16.

Figure 2A:
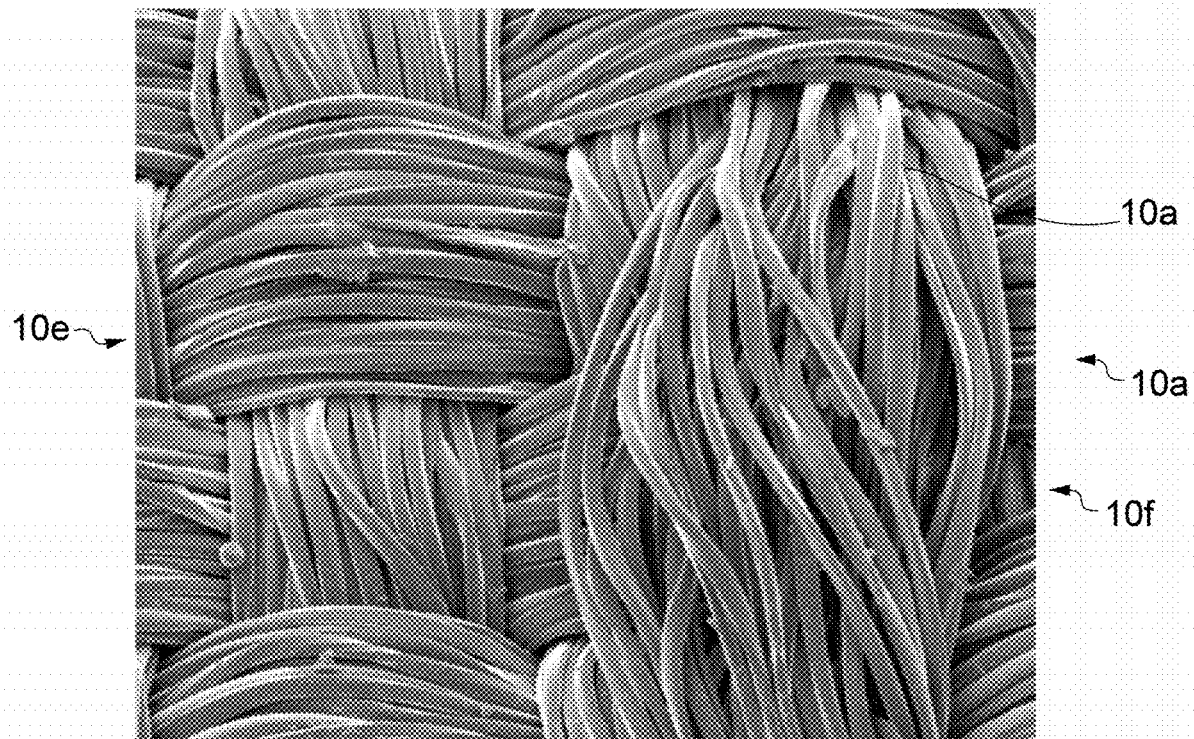
Figure 2B:
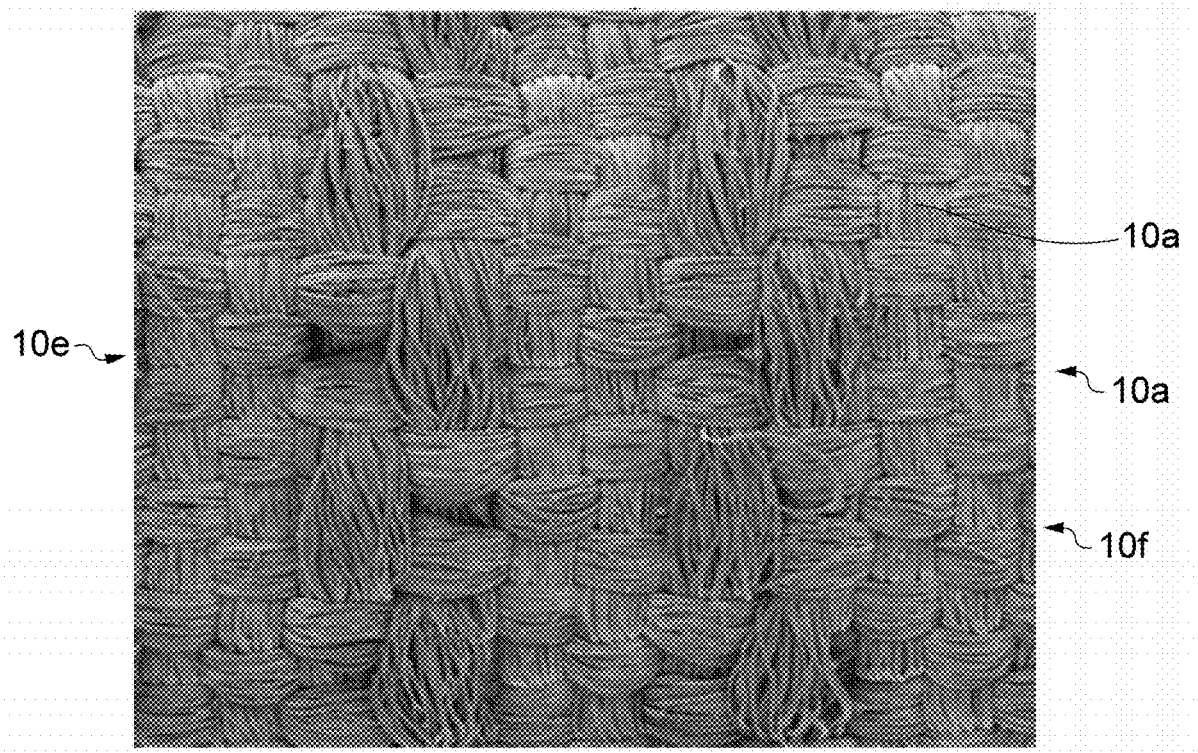

FIGS. 2a and 2b show the inner surface 10a of the wall 10f of the conduit 10 in more detail. FIGS. 2a and 2b show the porous nature of the conduit 10. The conduit 10 is a woven structure and, in this embodiment, is generally a 1/1 twill weave type. As described above, the unprocessed woven conduit 10 will allow blood to leak through the gaps in the fibres of the conduit 10, and it must therefore be sealed prior to implantation in the human or animal body.

The woven nature of the conduit 10 means that it is flexible. After applying the masking agent 12 and the sealing layer 14, the vascular graft 16 remains flexible, which helps to make the vascular graft 16 easier to manipulate and handle by, for example, a medical practitioner.

Figure 3A:
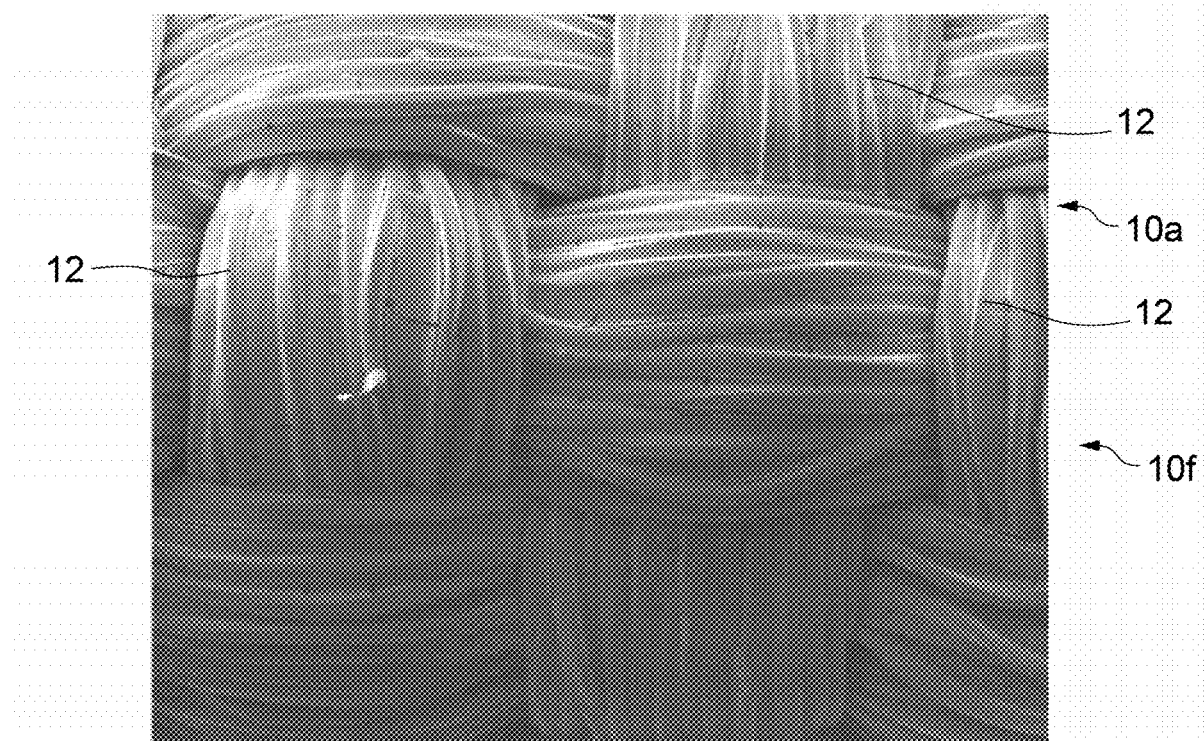
FIGS. 3a and 3b show a detailed view of the inner surface of the wall of the conduit of FIG. 1b after the addition of the masking agent.
Figure 3B:
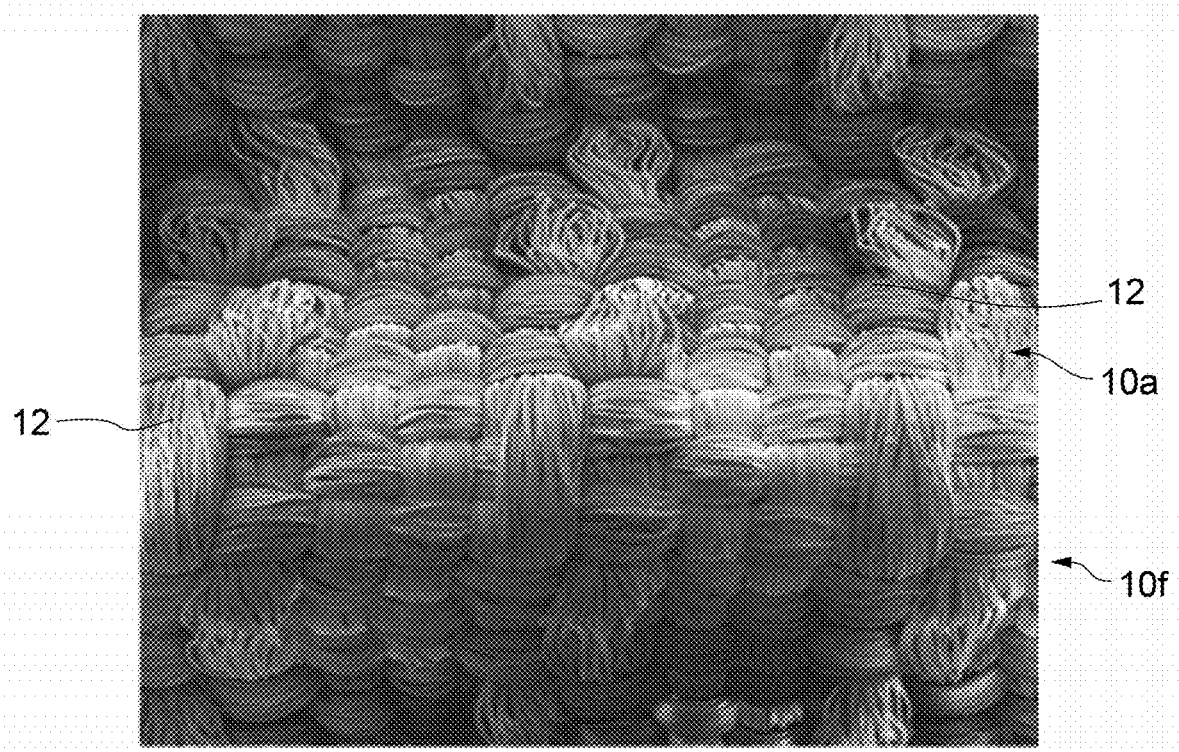

FIGS. 3a and 3b show a detailed view of the inner surface 10a of the wall 10f of the conduit 10 after the addition of the masking agent 12. In this embodiment, the masking agent 12 has been added to the conduit 10 from a polymer solution (an example of a masking agent solution) comprising approximately 5% w/v PVP in solution. In this embodiment, the conduit 10 has been immersed in the polymer solution. However, as described in more detail above, the masking agent 12 could be added to the conduit 10 in other ways and the polymer solution could comprise between approximately 5% w/v and approximately 30% w/v of polymer in solution. In the embodiment illustrated in FIGS. 3a and 3b, the conduit 10 has been immersed in the masking agent solution for approximately 1 minute. However, it should be appreciated that the conduit 10 could be immersed in the masking agent solution for other durations of time.

In the embodiment shown in FIGS. 3a and 3b, the masking agent 12 substantially blocks the porous section 10e of the conduit 10. When the sealant 14 is applied to the conduit 10, the masking agent 12 mitigates the presence of the sealant 14 on the inner surface 10a of the wall 10f of the conduit 10. In this embodiment, the masking agent 12 forms an oleophobic layer (an example of a masking layer). Without wishing to be bound by theory, it is thought that the oleophobic properties of the masking layer helps to mitigate the presence of the sealant 14 on the inner surface 10a of the wall 10f of the conduit 10. It should be understood that in some embodiments the masking agent 12 need not form an oleophobic layer.

Figure 4A:
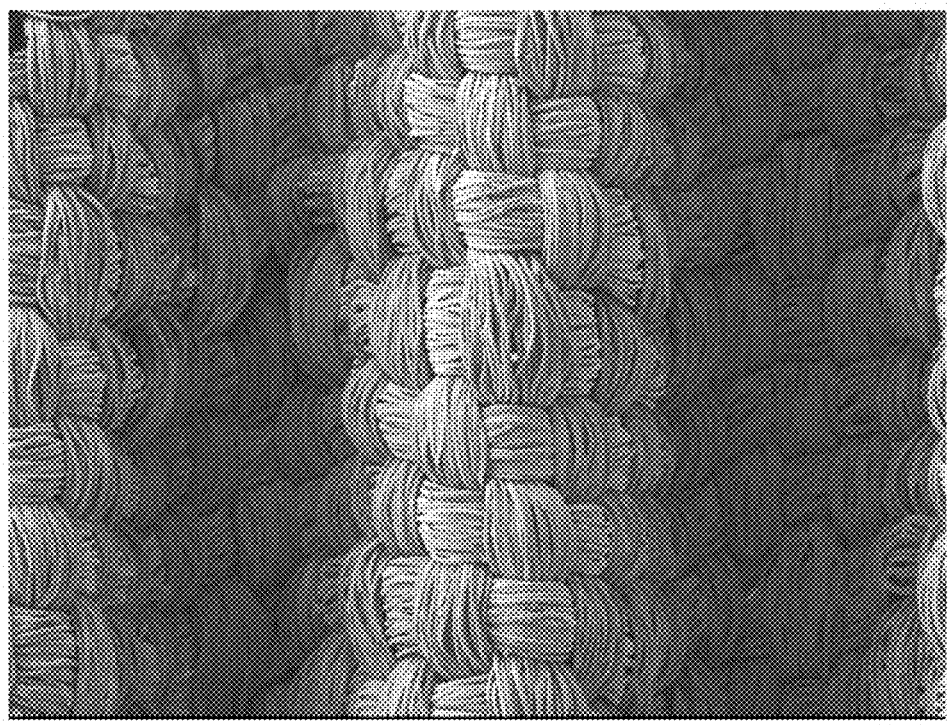
FIG. 4a shows a detailed view of the inner surface of the wall of the conduit of FIG. 1d.
Figure 4B:
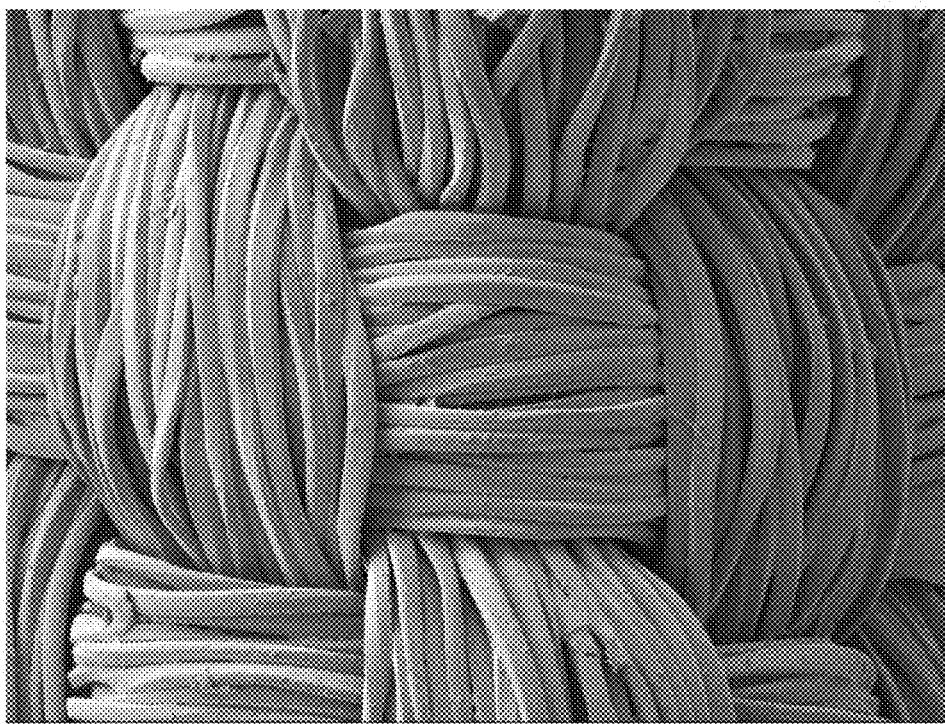
FIG. 4b shows a detailed view of the inner surface of the wall of the conduit of FIG. 1d.

FIGS. 4a and 4b show the inner surface 10a of the wall 10f of the conduit 10 after the sealant 14 has been added to the outer surface 10b of the wall 10f of the conduit 10. FIGS. 4a and 4b highlight the effectiveness of the masking agent 12 in mitigating the presence of sealant 14 on the inner surface 10a of the wall 10f of the conduit 10. In this embodiment, the masking agent 12 has been applied to the conduit 10 from a masking agent solution comprising approximately 7% w/v of PVP in solution. In the embodiment illustrated in FIGS. 4a to 5b, the sealant has been added to the outer surface 10b of the wall 10f of the conduit 10 by spray coating a sealant solution onto the outer surface 10b of the wall 10f of the conduit 10.

Figure 5A:
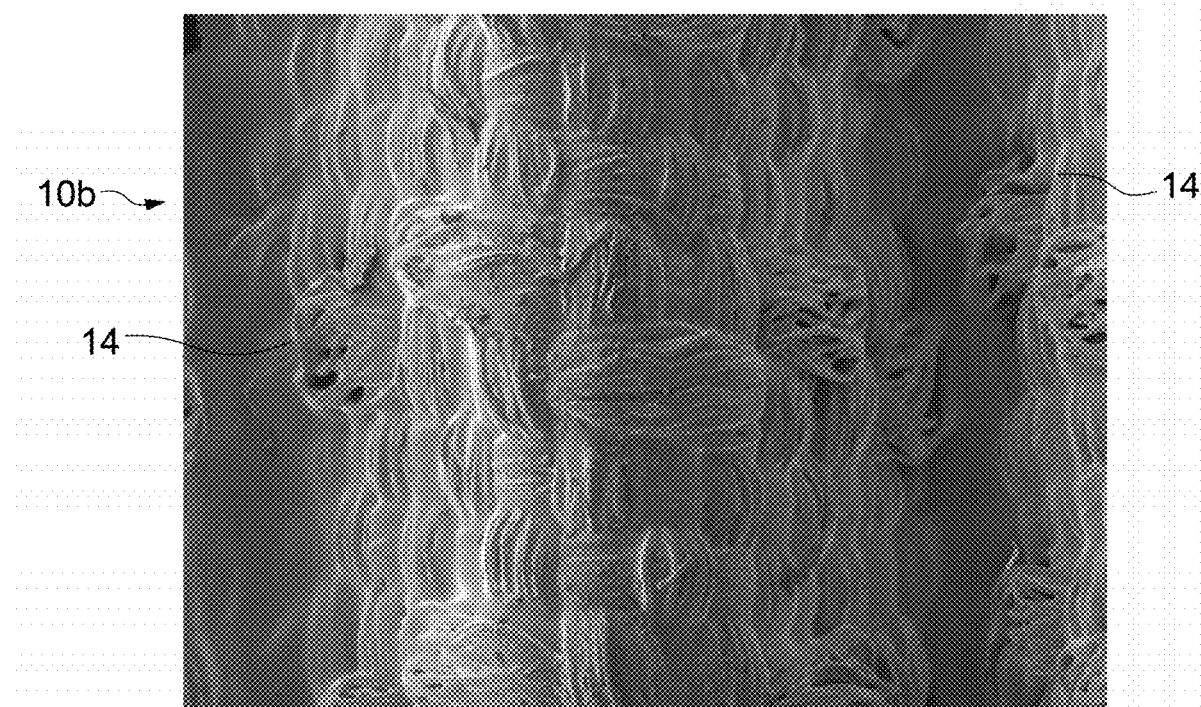
FIG. 5a shows a detailed view of the outer surface of the wall of the conduit of FIG. 1d.
Figure 5B:
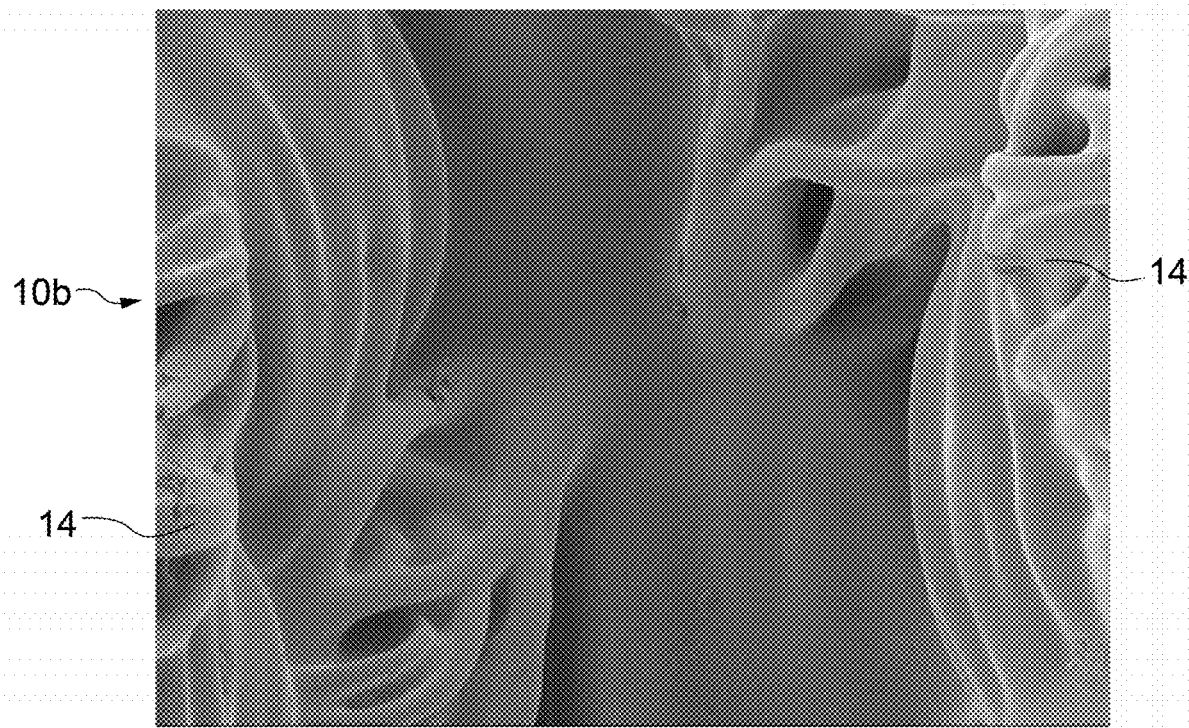
FIG. 5b shows a detailed view of the outer surface of the wall of the conduit of FIG. 1d.

FIGS. 5a and 5b show the presence of the sealant 14 on the outer surface 10b of the wall 10f of the conduit 10 of the embodiment shown in FIGS. 4a and 4b. In the embodiment shown in FIGS. 5a and 5b, the sealant solution comprises approximately 15% w/v of silicone in xylene.

FIGS. 4a and 4b, and FIGS. 5a and 5b, highlight the contrast between the inner surface 10a and the outer surface 10b of the wall 10f of the conduit 10 after the application of the sealant 14 to the conduit 10. The outer surface 10b of the conduit 10 is now substantially covered in the sealant 14, whereas the inner surface 10a of the wall 10f of the conduit 10 has retained the woven, porous properties of the conduit 10, because the inner surface 10a of the wall 10f of the conduit 10 is substantially devoid of the sealant 14. The masking agent 12 has mitigated the presence of the sealant 14 on the inner surface 10a of the wall 10f of the conduit 10. In this embodiment, the inner surface 10a of the wall 10f is configured to facilitate the growth of biological tissue thereon, and to allow for good adhesion between ingrowing biological tissue and the inner surface 10a. Presence of the sealant 14 on the inner surface 10a of the wall 10f of the conduit 10 could have an adverse impact on the ingrowth of biological tissue on the inner surface 10*a* of the wall 10*f* of the conduit 10, and on the adhesion between the biological tissue and the inner surface 10*a* of the wall 10*f* of the conduit 10.

Figure 6A:
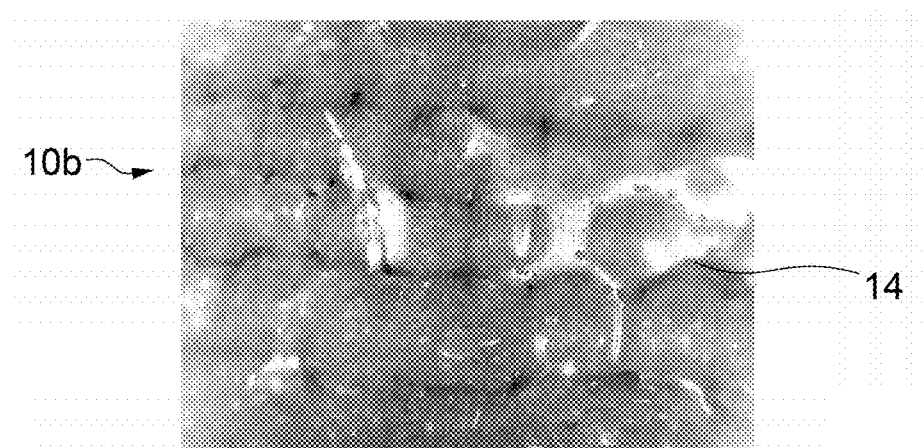
FIG. 6a shows a detailed view of the outer surface of the wall of the conduit of FIG. 1d.

FIG. 6*a* shows a detailed view of the outer surface 10*b* of the wall 10*f* of the conduit 10 after the addition of the sealant 14. In this embodiment, the sealant 14 is configured to mitigate movement of fluid through the wall 10*f* of the conduit 10. The wall 10*f* of the conduit 10 is substantially blood impermeable (i.e., blood cannot pass or leak through the wall 10*f* at an appreciable rate) after the addition of the sealant 14.

Figure 6B:
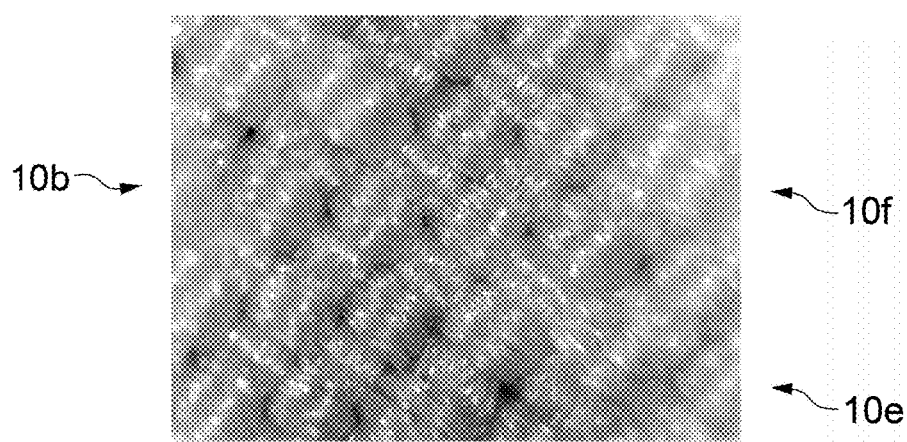
FIG. 6b shows a detailed view of the inner surface of the wall of the conduit of FIG. 1d.

FIG. 6*b* shows a detailed view of the inner surface 10*a* of the wall 10*f* of the conduit 10 after the addition of the sealant 14 to the conduit 10.

In the embodiment shown in FIGS. 6*a* and 6*b*, the masking agent 12 has been applied to the conduit 10 from a polymer solution comprising approximately 30% w/v PVP in solution, prior to the addition of the sealant 14. As described above, the masking agent 12 can be applied to the conduit 10 from a polymer solution comprising between approximately 5% w/v and approximately 30% w/v of polymer in solution.

One desirable feature for a sealed graft is that it may have sufficiently low levels of permeability to remain predominantly leak proof during the implant procedure. The applicable test method, as prescribed in ISO 7198, Whole Graft Permeability recommends testing using reverse osmosis (RO) filtered water at a test pressure of 120 mmHg. This parameter was based on a de facto standard established by the manufacturers of biologically sealed grafts (gelatin and collagen). A limit of 0.16 ml/min/cm$^2$ may be used to ensure that the graft meets and exceeds sealing capability of aforementioned grafts. Different applications, however, may have different permeability requirements, and such different permeability requirements are within the scope of the present invention.

Further embodiments were prepared according to the manufacturing process illustrated in FIGS. 1*a* to 6*b* and described above. The further embodiments are described in Table 1 below. The manufacturing process used to create the further embodiments listed in Table 1 is substantially the same as that illustrated and described in relation to FIGS. 1*a* to 6*b*, with the exception that different masking agents 12 and sealants 14 were used.

Commercial textile vascular grafts were used for the tests described hereinafter. Details for commercial graft samples are described below:

First Commercial Samples of Woven Graft Fabrics:
(a) Warp yarn: twisted, texturized, PET, 2 ply/44 denier per ply (or bundle)/27 filaments per ply or bundle.
(b) Weft yarn: twisted, texturized, PET, 2 ply/44 denier per ply (or bundle)/27 filaments per ply or bundle.
(c) Picks per cm, about 40 to 46.

Second Commercial Samples of Woven Graft Fabrics:
(a) Warp yarn: 80 Denier, 2 ply/40 denier per ply (or bundle)/27 filaments per ply (or bundle), PET, Spun Draw, texturized, 7.5 Twists per inch, Z twist.
(b) Weft yarn: 2 ply/40 Denier per ply (or bundle), 2 ply/40 denier per ply (or bundle)/27 filaments per ply (or bundle), PET, TXT, S & Z Twist.
(c) Picks per inch, about 155.

The tests done below in Table 1 were performed on the first commercial samples of woven graft fabrics.

TABLE 1

| Masking Agent | | Sealant | | Sealant Coating Method | Sealant Coverage (mg/cm$^2$) | Leak Rate (ml/min/cm$^2$) | Leak Rate ≤0.16 ml/min/cm$^2$ |
|---|---|---|---|---|---|---|---|
| Polymer | Solvent | Polymer | Solvent | | | | |
| 7% w/v PVP | Water | 30% w/v Silicone | Xylene | Brush × 1 | 11.33 | 0.19 | No |
| 7% w/v PVP | Water | 30% w/v Silicone | Xylene | Brush × 1 | 8.30 | 0.19 | No |
| 4% w/v PVP | Water | TPU and Silicone | THF | Brush × 1 | 2.00 | 5.79 | No |
| 4% w/v PVP | Water | TPU and Silicone | THF | Brush × 2 | 3.70 | 0.46 | No |
| 30% w/v PVP | Water | 30% w/v Silicone | Xylene | Brush × 1 | 5.3 | 1.78 | No |
| 30% w/v PVP | Water | 30% w/v Silicone | Xylene | Brush × 1 | 5.2 | 3.49 | No |
| 30% w/v PVP | Water | 30% w/v Silicone | Xylene | Brush × 1 | 7.6 | >12.24 | No |
| 25% w/v PVP and 18% w/v Glycerol | Water | 30% w/v Silicone | Xylene | Brush × 1 | — | — | No |
| 7% w/v PVP | Water | 30% w/v Silicone | Xylene | Brush × 1 | 4.8 | 0 | Yes |
| 7% w/v PVP | Water | 30% w/v Silicone | Xylene | Brush × 2 | 8.9 | 0 | Yes |
| 7% w/v PVP | Water | 30% w/v Silicone | Xylene | Brush × 3 | 8.3 | 0 | Yes |
| 7% w/v PVP | Water | 30% w/v Silicone | Heptane | Brush × 1 | 7.6 | 0.69 | No |
| 7% w/v PVP | Water | 30% w/v Silicone | Heptane | Brush × 2 | 13.8 | 0.02 | Yes |
| 7% w/v PVP | Water | 30% w/v Silicone | Heptane | Brush × 3 | 18.6 | 0 | Yes |
| 7% w/v PVP | Water | 30% w/v Silicone | Xylene | Brush × 1 | 8.0 | 0.09 | Yes |
| 7% w/v PVP | Water | 30% w/v Silicone | Xylene | Brush × 2 | 11.5 | 0.14 | Yes |

TABLE 1-continued

| Masking Agent | | Sealant | | Sealant Coating Method | Sealant Coverage (mg/cm$^2$) | Leak Rate (ml/min/cm$^2$) | Leak Rate ≤0.16 ml/min/cm$^2$ |
|---|---|---|---|---|---|---|---|
| Polymer | Solvent | Polymer | Solvent | | | | |
| 7% w/v PVP | Water | 30% w/v Silicone | Xylene | Brush × 2 | 11.5 | 0.05 | Yes |
| 7% w/v PVP | Water | 30% w/v Silicone | Xylene | Brush × 3 | 15.6 | 0 | Yes |
| 7% w/v PVP | Water | 30% w/v Silicone | Xylene | Brush × 1 | 7.1 | 0.01 | Yes |
| 7% w/v PVP | Water | 30% w/v Silicone | Xylene | Brush × 2 | 9.7 | 0.03 | Yes |
| 7% w/v PVP | Water | 30% w/v Silicone | Xylene | Brush × 2 | 9.1 | 0.03 | Yes |
| 7% w/v PVP | Water | 30% w/v Silicone | Xylene | Brush × 3 | 12.6 | 0.02 | Yes |
| 7% w/v PVP | Water | 30% w/v Silicone | Xylene | Brush × 1 | 6.0 | 0.22 | No |
| 7% w/v PVP | Water | 30% w/v Silicone | Xylene | Brush × 2 | 14.3 | 0.03 | Yes |
| 7% w/v PVP | Water | 30% w/v Silicone | Xylene | Brush × 2 | 9.8 | 0.10 | Yes |
| 7% w/v PVP | Water | 30% w/v Silicone | Xylene | Brush × 3 | 13.8 | 0.06 | Yes |
| 12% w/v PVP | Water | 30% w/v Silicone | Xylene | Brush × 2 | 11.0 | 6.25 | No |
| 12% w/v PVP | Water | 30% w/v Silicone | Xylene | Brush × 2 | 11.3 | 1.81 | No |
| 7% w/v PVP | Water | 15% w/v Silicone | Xylene | Spray × 1 | 3.5 | 7.24 | No |
| 7% w/v PVP | Water | 15% w/v Silicone | Xylene | Spray × 2 | 5.6 | 0.07 | Yes |
| 7% w/v PVP | Water | 15% w/v Silicone | Xylene | Spray × 3 | 5.3 | 0.57 | No |
| 7% w/v PVP | Water | 15% w/v Silicone | Xylene | Spray × 1 | 6.7 | 5.11 | No |
| 7% w/v PVP | Water | 15% w/v Silicone | Xylene | Spray × 1 | 8.7 | 0.01 | Yes |
| 7% w/v PVP | Water | 15% w/v Silicone | Xylene | Spray × 1 | 6.4 | 0.02 | Yes |
| 7% w/v PVP | Water | 15% w/v Silicone | Xylene | Spray × 1 | 4 | 8.41 | No |
| 7% w/v PVP | Water | 15% w/v Silicone | Xylene | Spray × 1 | 6.3 | 8.99 | No |
| 7% w/v PVP | Water | 15% w/v Silicone | Xylene | Spray × 1 | 3.8 | 5.05 | No |
| 7% w/v PVP | Water | 15% w/v Silicone | Xylene | Spray × 1 | 8.1 | 1.17 | No |
| 7% w/v PVP | Water | 15% w/v Silicone | Xylene | Spray × 1 | 7.9 | 0.14 | Yes |
| 7% w/v PVP | Water | 15% w/v Silicone | Xylene | Spray × 1 | 8.2 | 5.94 | No |
| 7% w/v PVP | Water | 15% w/v Silicone | Xylene | Spray × 1 | 8.8 | 1.08 | No |
| 7% w/v PVP | Water | 15% w/v Silicone | Xylene | Spray × 1 | 11.4 | 0.01 | Yes |
| 7% w/v PVP | Water | 15% w/v Silicone | Xylene | Spray × 1 | 6.8 | 5.93 | No |
| 7% w/v PVP | Water | 15% w/v Silicone | Xylene | Spray × 1 | 7.4 | 0.16 | Yes |
| 7% w/v PVP | Water | 15% w/v Silicone | Xylene | Spray × 1 | 11.9 | 0 | Yes |
| 6% w/v PVP and 1% w/v Glycerol | Water | 15% w/v Silicone | Xylene | Spray × 1 | 7.8 | 0.04 | Yes |

A hobby spray gun was used for all spray application tests where sealants were sprayed onto graft samples. The spray distance from the graft samples was approximately 50 mm. Grafts were held horizontally on mandrel and rotated in a rotisserie. Spray rates were not measured but were controlled by a combination of the nozzle traverse rate (estimated at 2 seconds/cm), graft rotation speed (estimated between one and three revolutions per second) and overall spray volume rate. Craft bristle brushes were used for all brush application tests where sealants were brushed onto graft samples.

As indicated in Table 1, if the wall 10*f* has a Leak Rate ≤0.16 ml/min/cm$^2$ then the conduit 10 is considered suitable for implantation and is considered substantially impermeable. In some further embodiments, the masking agent 12 comprises glycerol. Without wishing to be bound by theory, the presence of glycerol in the masking agent 12 is thought to mitigate cracking of the masking agent 12 when applied to the conduit 10.

Masking agents described herein prevent sealants, such as the liquid silicone elastomer dispersion, from penetrating throughout the thickness of the graft wall and reaching the lumen or blood contacting surface of the graft. Sealants, such as silicone, are believed to adhere to graft fibres on the external surface of the graft through two mechanisms:

a. Where graft fibres have had the mask agent ablated or otherwise free of the masking agents, the liquid silicone elastomer dispersion adheres to the surface of the graft fibres, such as PET fibres.

b. Where surface fibres are individually sheathed by the masking agent, these fibres are encapsulated and a mechanical interlocking takes place rather than surface adhesion.

Silicone will adhere to the PET fibre surface where there is no masking agent, but will also encapsulate PET fibres which are sheathed in masking agent.

The masking agent is believed to act like a slurry when applied to a textile and can flow and cover gaps between the yarn bundles and also seep between the yarn fibers. It acts as a viscous mixture moving through the fabric and settling and collecting at areas of low energy. Rather than attaching to individual fibers it continues to move and pool until a masking agent drying process initiates and through the evaporation of its solvent, such as water, the masking agent then solidifies wherever it has gathered.

The elastomeric sealant (e.g., silicone) may not adequately attach to the textile surface where excessive concentrations of masking agent are present. If the masking agent is too viscous and has fully encapsulated an area of fabric and then dried, there may be no exposed yarn filaments for the silicone to mechanically encapsulate and lock onto. Without this mechanical encapsulation of the yarn by the silicone, then the adhesion may be poor and possibly non-existent once the masking agent is removed.

While the masking agent may appear to thinly coat the individual filaments as it moves or washes through the textile, the concentrations remaining in these washed through areas after drying are not sufficient to prevent subsequent encapsulation and adhesion of the silicone adhesive to the yarn bundles.

Any synthetic hydrophilic polymer and any biological hydrophilic polymer, e.g., gelatin, partially hydrolysed collagen, dextran, hyaluronic acid, alginates and starches (e.g., hydroxyethyl starch) and chitosan may be used as masking agents. Pluronic F127 PEG, which is soluble in cold water but insoluble in warm water, may also be used as a masking agent. Desirably, masking agents derived from animal products may are removed prior to vascular applications. As such, the masking agents, including animal derived masking agents, if any, are removed from the final product, such grafts may suitable be used in vascular applications. Furthermore, as the masking agents are removed from the textile graft prior to any applications with a patient, including vascular applications, the masking agents need not be biocompatible.

Desirably, the masking agent is highly soluble in water. It can be any polymer which can swell in a liquid which has a Hildebrand Solubility Parameter (Delta SI units) of 24 or higher.

Masking agents useful with the present invention may have molecular weights from about 400 or 1,000 to about 1,000,000. Desirably, the molecular weight may vary from about 3,000 to about 30,000, and more desirably from about 6,000 to about 15,000

One useful sealant may be a dispersion of silicone in a nonpolar 'solvent' or carrier medium. Useful cross linking is through acetoxy 'room temp vulcanisation' chemistry but two part platinum cure chemistry could also be used as well as ultraviolet (UV) curing.

For samples employing a polymer supplied as a dispersion, for example NuSil MED 6605 and Med 6606, discrete amounts of polymer dispersion were decanted by weight into individual pots for either direct coating onto the graft or further addition of solvent, by weight.

All silicone dispersions used were acetoxy curing. Curing schedules are recommended at 72 hours, however due to the extremely thin cross section/large surface area of the graft, full cures have been observed apparent within 24 hours. Subsequent washing of the device in water may speed up the curing and ensure full cross linking. These times are, however, non-limiting, and other cure times and conditions may suitably be used.

The preferred polymers for coating, in order to achieve a soft and flexible graft with handling characteristics similar to that of a gelatin sealed graft, are those with very low Shore hardness values. The preferred silicone elastomers, MED 6605 and MED 6605 have Durometer Type A values of 25 and 20 respectively. Both of these grades can provide grafts with suitable flexibility and handling characteristics, when thin coatings are applied. As multiple coatings are applied, stiffness may increase and flexibility may reduce.

Harder grades can be used as an alternative to thicker coatings in order to create stiffer grafts if required.

Alternative coatings, such as TPU-Silicones (Advansource Chronosil 75 A or Aor-Tech Elast-Eon E5-130) can be used however, these have Durometer Hardness of 75 A and 77 A respectively, therefore may create grafts which may be stiffer, if desired, than current gelatin sealed grafts. Such stiffer grafts may have some benefits for specific applications, however, may not meet expectations for conventional surgeon handling.

Additional useful sealant materials include, but are not limited to:

(a) Applied Silicone Corporation, PN 40021, Implant grade high strength RTV Silicone Elastomer Dispersion in Xylene. This material is suitable for use in fabricating high strength, elastic membranes of any shape and thickness using processes such as dipping, casting, spraying or brushing. After evaporating the solvent, the silicone is room temperature vulcanized (RTV) by exposure to ambient air. The key features of this material are high strength, low durometer, (Shore A 24) and is supported by ISO 10993 testing and compendium to support regulatory submissions.

(b) AdvanSource Biomaterials Corporation, ChronoFlex AR, polycarbonate based thermoplastic urethanes. These materials may be used for moulding, casting and dip-coating and are fully synthesized in liquid providing high strength & elongation while maintaining the inherent polycarbonate advantage of long-term permanent durability and resistance to environmental stress cracking (ESC). Additionally, they may be electrospun or used in water emulsion processes. Examples of specific useful materials include, but are not limited to, ChronoFlex C80 A 5% and ChronoFlex AR 23%.

Suitable sealants are low durometer elastomers (desirably less than or equal to about 40 A durometer or shore hardness 40 A, more desirably less than or equal to about 30 A durometer or shore hardness 30 A, even more desirably less than or equal to about 20 A durometer or shore hardness 20 A) and have good biostability.

One parameter which may be considered in the choice of sealant is the stiffness or elastic modulus. Usually with elastomers the modulus is not linear thus at each elongation the stress (or force) is measured. A material with lower stress @ % strain will provide less resistance to extension and will therefore feel more flexible and closer to matching the handling of a gelatin sealed graft.

Preferred materials are low stress silicone rubbers, such as NuSil MED 6605 and MED 6606, with Stress @ Strain values <180 @ 200%.

Useful Polyurethane and Silicone-polyurethane grades, include, but are not limited to:

TABLE 2

| Material | Manufacturer | Grade | Stress (psi) at % elongation |
|---|---|---|---|
| Silicone Rubber | NuSil | MED 6606 | 50 @ 100% |
| Silicone Rubber | NuSil | MED 6605 | 160 @ 300% |
| Silicone Rubber | Applied Silicone | Dispersion PN 40021 | 170 @ 300% |
| TPU - Silicone | Advansource | ChronoSil adjusted | 570 @ 200% |
| TPU - silicone | Biomerics | Quadrasil Elast-EON E5-130 | 725 @ 200% |
| TPU - aliphatic polycarbonate | Advansource | Chronoflex AL 75A | 800 @ 200% |
| TPU - 10% silicone | Advansource | ChronoSil 75A 10% Si | 834 @ 200% |

The present invention is not limited to the use of silicone as the polymeric sealant. Other useful coating materials for both medical and non-medical textiles may include, for example, polytetrafluoroethylene, polyethylene, poly(hydroxyethly methacrylate), poly(vinyl alcohol), polycaprolactone, poly(D, L-lactic acid), poly(L-lactic acid), poly(lactide-co-glycolide), poly(hydroxybutyrate), poly(hydroxybutyrate-co-valerate), polydioxanone, polyorthoester, polyanhydride, poly(glycolic acid), poly(glycolic acid-cotrimethylene carbonate), polyphosphoester, polyphosphoester urethane, poly(amino acids), cyanoacrylates, poly(trimethylene carbonate), poly(iminocarbonate), copoly(ether-esters), polyalkylene oxalates, polyphosphazenes, polyiminocarbonates, aliphatic polycarbonate, polyethylene oxide, polyethylene gylcol, poly(propylene oxide), polyacrylamide, polyacrylic acid (30-60% solution), polymethacrylic acid, poly(N-vinyl-2-pyrollidone), polyurethane, poly(aminoacid), cellulosic polymer (e.g. sodium carboxymethyl cellulose, hydroxyethyl celluslose), collagen, carrageenan, alginate, starch, dextrin, gelatin, poly(lactide), poly(glycolide), polydioxanone, polycaprolactone, polyhydroxybutyrate, poly(phospazazene), poly(phosphate ester), poly(lactide-co-glycolide), poly(glycolide-co-trimethylene carbonate), poly(glycolide-co-caprolactone), polyanhydride, polyamide, polyesters, polyether, polyketone, polyether elastomer, parylene, polyether amide elastomers, polyacrylate-based elastomer, polyethylene, polypropylene, and/or and derivatives thereof. Other useful coating materials, in particular for but not limited to non-medical textiles, may include natural rubbers, natural gums, acrylic polymers, polybutadienes, styrene-butadiene copolymers or rubbers, butadiene-acrylonitrile copolymers, polyisobutylenes, isoprene-isobutylene copolymers, polysulfide rubbers, chloroprene rubbers (neoprene), chlorosulfonated polyethylene, fluorinated polymers, vinyl resins, and the like. Further, coating materials may include metallic materials and powdered materials.

Figure 7:
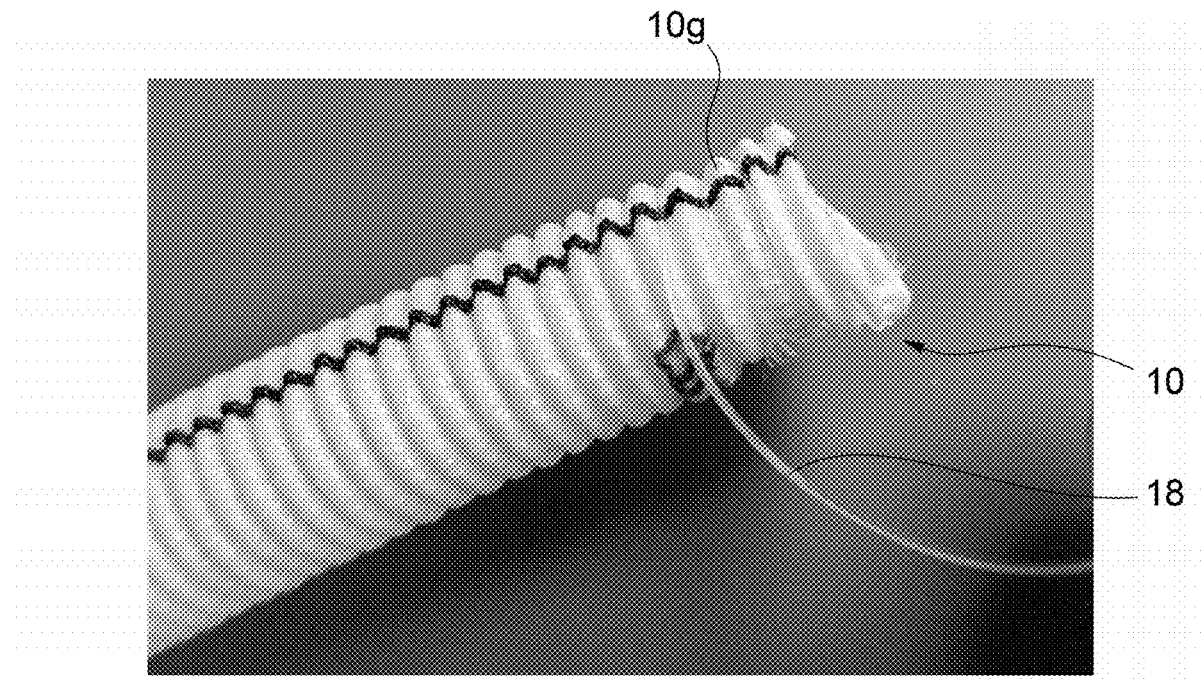

FIG. 7 depicts a further embodiment of the conduit 10. As best shown in FIG. 7, the conduit 10 comprises a number of crimps 10g. In this embodiment, a support member 18 is added to the outer surface 10b, of the wall 10f of the conduit 10. In particular, the support member 18 is added by multiple stages of sealant application. For example, the sealant may be added to the outer surface of the conduit 10 as described above, then the support member 18 may be disposed over the sealed graft, followed by applying another stage of sealant application, which after drying and/or curing will aid in the securement of the support member 18 to the conduit 10. However, it should be understood that the support member 18 could be added to the conduit 10 in other ways. The step of adding the support member 18 to the outer surface 10b of the wall 10f of the conduit 10 is carried out prior to the step of adding the sealant 14 to the conduit 10. The sealant 14 is configured to attach the support member 18 to the conduit 10. In this embodiment, the support member 18 is added to the conduit 10 and the sealant 14 is then added to the conduit 10 in order to seal the conduit 10, and to attach the support member 18 to the conduit 10. Moreover, it should be understood that it is within the scope of the present invention to have multiple applications of masking agent and/or sealant either after or prior to drying and/or curing the prior application.

The support member 18 is a flexible, polymer wire, which in this embodiment is wrapped around the outer surface 10b of the wall 10f of the conduit 10 and is arranged to nest between the crimps 10g of the conduit 10. One of the advantages of adding the support member 18 to the conduit 10, as illustrated and described here, is that the conduit 10 is made more robust while retaining much of its flexible characteristics. As stated above, the conduit 10 is able to be manipulated by a medical practitioner in a more efficient way because the conduit 10 is flexible.

In the embodiment illustrated in FIG. 7, the support member 18 is made from polyethylene terephthalate (PET). However, it is understood that the support member 18 could comprise at least one of: a polymer material, a metal material, a shape memory alloy, and a superelastic alloy. In some embodiments, the support member 18 could comprise at least one of: polyethylene terephthalate, polytetrafluoroethylene, polyurethane, polycarbonate, silicone, stainless steel, titanium, nickel, and nickel titanium (Nitinol).

Figure 8:
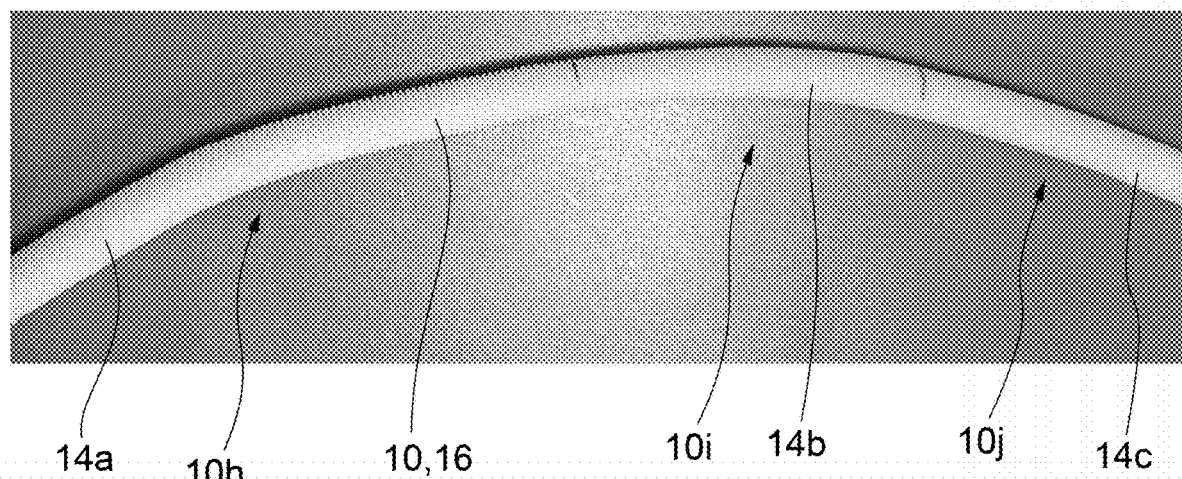
FIG. 8 depicts an alternative embodiment of a conduit manufactured according to the process of FIGS. 1a to 1d.

FIG. 8 shows an alternative embodiment of a conduit 10 manufactured according to the process illustrated in FIGS. 1a to 1d. The conduit 10 depicted in FIG. 8 has been manufactured in the same way as that depicted in FIG. 1d, with the following differences. The conduit 10 has three sections 10h, 10i, 10j. Sealant 14a, 14b and 14c has been selectively added to the sections 10h, 10i, 10j, such that each section 10h, 10i, 10j, has a different amount of sealant 14a, 14b, 14c, present thereon. In this embodiment, each of the sections 10h, 10i, 10j have a substantially different degree of flexibility. The first section 10h has a higher degree of flexibility than the second section 10i. Similarly, the second section 10i has a higher degree of flexibility than the third section 10j. As shown in FIG. 8, the crimps 10g of the first section 10h are more visible than in the second section 10i and third section 10j, because the second and third sections 10i, 10j, have a higher amount of sealant added thereto, which causes the crimps 10g in these sections 10i, 10j, to be less pronounced. In applications where a further prosthesis is connected to an end of the vascular prosthesis 16, the end of the third section 10j is more suited for connection to the further prosthesis.

An example of how the vascular graft 16 may be used will now be provided.

The vascular graft 16 described in FIGS. 1a to 6b, which may be thought of as a sealed, processed conduit 10, is capable of being implanted in the human or animal body over the long term. This is because the vascular graft 16 is biocompatible, that is it will not illicit a foreign body response in the human or animal body, and it is not toxic to surrounding biological tissue.

The masking agent 12 is configured to biodegrade in the body. Therefore, any residual masking agent 12 present on the conduit 10 will biodegrade in the body. However, as described in more detail above, the masking agent 12 need not be biodegradable, as in some embodiments the masking agent 12 will be removed substantially entirely from the conduit 10. In other embodiments, the masking agent 12 need not be removed from the conduit 10.

The vascular graft 16 can be used to bypass a region, or a section of a blood vessel. For example, if a medical practitioner identifies a blocked, a diseased region or partially blocked region of a blood vessel, they may decide to bypass that region by using the vascular graft 16. In this example, the inlet 10c of the vascular graft 16 may be attached to one point of the blood vessel, and the outlet 10d of the vascular graft 16 may be attached to another point of the blood vessel. In another example, the blood vessel could be diseased, or have been severed or bisected in order to connect the vascular graft 16 to two ends of the severed blood vessel. Because the vascular graft 16 is sealed, blood may flow through the vascular graft 16 in order to bypass the blocked, diseased, or partially blocked region of the blood vessel, and the leaking of blood through the walls 10f of the conduit 10 is mitigated by the presence of the sealant 14.

Once the vascular graft 16 is in place, biological tissue will grow into the inner section 10a of the vascular graft 16 in order to form a pseudointima. Over time, the psuedointima will form, adhering to the inner section 10a of the vascular graft 16. During this time, the vascular graft 16 prevents leakage of blood through the wall 10f and acts as a scaffold for the ingrowing biological tissue.

The vascular graft 16 may also be used to connect a further prosthesis, such as a heart assist device, a biological heart valve or a synthetic heart valve, to a blood vessel. For example, the inlet 10c of the vascular graft 16 may be connected to an outlet of a synthetic heart valve, and the outlet 10d of the vascular graft 16 may be connected to an end of a blood vessel. The advantage of this use of the vascular graft 16 is that a heart assist component can be used with a wide variety of shapes and sizes of blood vessels, as the vascular graft 16 can be provided in a range of sizes. The medical practitioner is then able to select which particular vascular graft 16 will interface well with the synthetic heart valve and the blood vessel. This avoids the need for a range of different configurations of heart assist device to be used, as a standard part can be used and customised by adding different types and sizes of vascular graft 16. It will be appreciated that, depending on the nature of the heart assist device, multiple vascular grafts 16 could be used with the heart assist device.

While the embodiments illustrated and described here show a cylindrical conduit 10 with an inlet 10c and an outlet 10d, other shapes of conduit 10 could be used. For example, a Y shaped, T-shaped, or a multi-channel conduit 10 could be used.

Figure 9A:
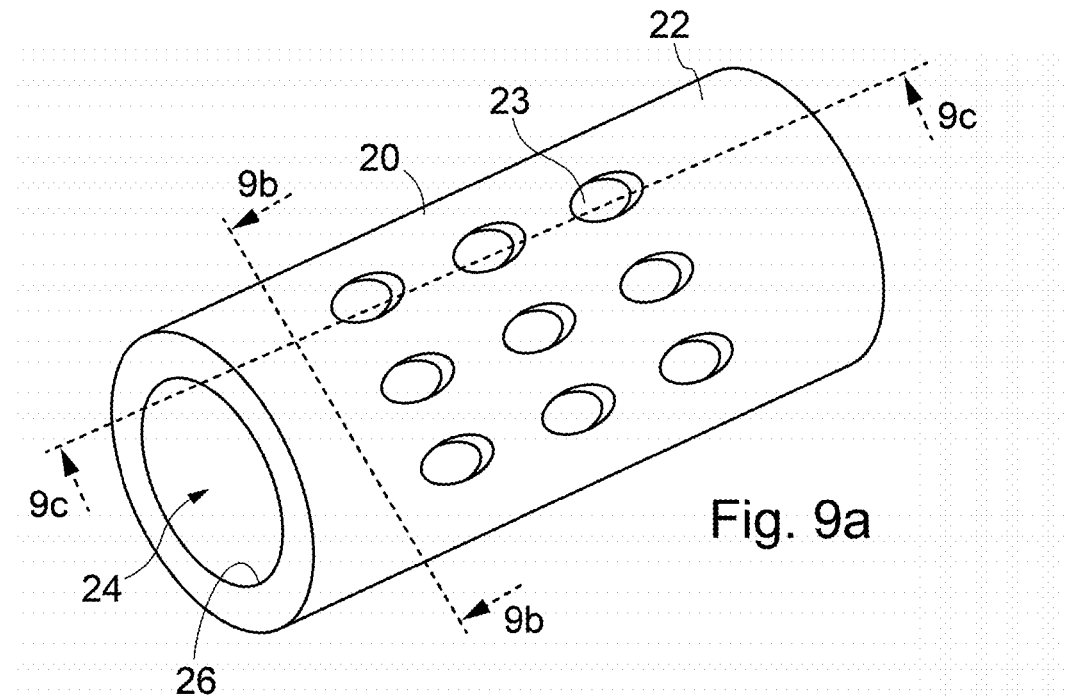
FIG. 9a is a perspective view of a hollow and perforated mandrel for use with the present invention.
Figure 9B:
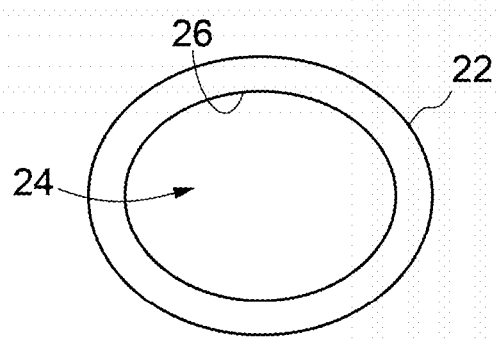
FIG. 9b is a cross-section view of the mandrel of FIG. 9a taken along the 9b-9b axis showing a hollow lumen passageway through the mandrel.
Figure 9C:
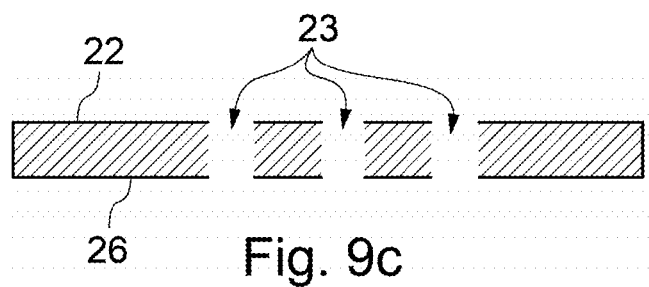
FIG. 9c is a partial cutaway view of the wall of the mandrel of FIG. 9a taken along the 9c-9c axis showing perforations or holes through the mandrel wall.

FIG. 9a is a perspective view of a perforated mandrel 20 useful with the systems and/or kits of the present invention for processing textile substrates in accordance with the present invention. As depicted in FIGS. 9a and 9b, the mandrel 20 may be a hollow mandrel having an open lumen 24. One or both ends 26 of the mandrel 20 may be open ends. Alternatively, one or both ends 26 of the mandrel 20 may be closed ends (not shown). As depicted in FIGS. 9a and 9c, perforations or holes 23 may be disposed within the tubular wall of the mandrel 20.

The mandrel 20 may be used for a variety of purposes. For example, the mandrel 20 could be used to deliver the masking agent or the water-soluble material to a tubular textile, such as a graft. In such a use, a tubular textile (not shown) may be disposed over the outer surface 22 of the mandrel 20. The masking agent or the water-soluble material may be delivered into the open lumen 24 of the mandrel 20, for example into the open lumen 24 via an open end 26. The opposed end may be closed or open, such as in the case of a circulating system for the fluid masking agent or water-soluble material. The fluid masking agent or water-soluble material would flow through the perforations or holes 23 and onto and into the graft (not shown) disposed over the mandrel 20.

The mandrel 20 may have a controlled amount of fluid masking agent or water-soluble material within the lumen 24 to control the amount of fluid masking agent or water-soluble material exposed to the graft (not shown). The fluid masking agent or water-soluble material contained within the mandrel 20 may be forced onto the graft through the use of a pressure differential (higher pressure within the lumen 24 than outside the lumen 24) or through rotational forces when the mandrel 20 is disposed on or within a rotating or spinning device.

A mandrel not having the perforations 20 (not shown) may be used to dispose a layer of fluid masking agent or water-soluble material over the outer surface of the mandrel. The masking layer may be viscous enough or partially cured to remain on the mandrel until a graft is disposed over the mandrel. The masking layer may then be releasably disposed over the inner surface of the graft.

The mandrel 20 may also be used for control of fluid migration. For example, the pressure within the lumen 24 may be lower than the pressure outside of the lumen 24. Such a negative pressure or vacuum may be used to migrate the masking agent or water-soluble material away from the outer surface of a graft (not shown).

The mandrel 20 may also be used for drying the fluid masking agent or water-soluble material. A warm gas, such as air, may be introduced into the lumen 24, flow through the perforations or holes 23, and dry the fluid masking agent or water-soluble material. Alternatively, a heat source may be disposed outside of the mandrel 20, and the flow of heat, such as heated air, may be controlled through the application of a negative pressure at the lumen 24.

A mandrel, either the same or different, may be used throughout different applications and techniques described herein, such as, but not limited to, masking agent application and/or dispersion, masking agent drying, sealant application and/or dispersion, sealant drying and/or curing, textile washing, and the like. A tubular textile may be substantially disposed over a mandrel or only a portion of the tubular textile may be disposed over a mandrel. For example, one end of a tubular textile may be supported by a mandrel and the other end of the tubular textile may be supported by a different mandrel, and the like.

The substantially water-insoluble sealant may also be applied to the graft while the graft is on a solid or non-perforated mandrel or on a perforated mandrel 20. The substantially water-insoluble sealant may be applied to the graft by any suitable means, such as by brushing, spraying, roller coating, spinning the substantially water-insoluble sealant thereon.

Furthermore, if desired the substantially water-insoluble sealant may be cured with the graft disposed over a mandrel.

Further, other materials, such as colorants, therapeutic agents, dyes, fluorescent indicators, and the like maybe applied to the graft.

Therapeutic agents may include, but are not limited to: anti-thrombogenic agents (such as heparin, heparin derivatives, urokinase, and PPack (dextrophenylalanine proline arginine chloromethylketone); anti-proliferative agents (such as enoxaprin, angiopeptin, or monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); anti-neoplastic/antiproliferative/anti-miotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl keton, an RGD peptide-containing compound, heparin, antithrombin compounds, platelet receptor antagonists, anti-thrombin antibodies, anti-platelet receptor antibodies, aspirin, prostaglandin inhibitors, platelet inhibitors and tick antiplatelet peptides); vascular cell growth promoters (such as growth factor inhibitors, growth factor receptor antagonists, transcriptional activators, and translational promotors); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; agents which interfere with endogenous or vasoactive mechanisms; and combinations thereof.

Masking Agent Drying and Uniformity Tests

Tests were performed to determine how long it took for a standard woven graft immersed in PVP to dry at different concentrations, and if PVP dried in a homogeneous fashion throughout the textile. A series of tests at different concentrations of PVP were done to determine if the concentration made a difference on the drying nature of the substance.

The tests used 15%, 10% & 5% PVP solution profiles. First, a 15% solution of PVP was made with 15 g of PVP and 100 mL of water. This was agitated until PVP was fully dissolved into solution. Graft samples were prepared by cutting approximately 50 mm of a commercial tubular graft. The graft samples were, if necessary, dried and were weighed. Graft samples were then soaked in the 15% PVP solution. The wet grafts were weighed to provide initial weights. The samples were placed vertically near a running fan. The graft samples were weighed at 5-minute intervals until there was a constant weight being displayed. The graft samples were cut into 4 labelled pieces. Each quarter piece was weighed. The quarter pieces were then washed, dried, re-weighed when fully dry. The lengths of the dry-washed graft were measured.

Next, 50 mL of water was added to the 15% PVP solution in order to make a 10% PVP solution. The above textile processing steps were repeated for the 10% PVP solution Next 150 mL of water was added to the 10% PVP solution to make a 5% PVP solution. The above textile processing steps were repeated for the 5% PVP solution.

Results: 15% PVP Profile

TABLE 3

| Time (min) | Weight (g) |
|---|---|
| Dry | 1.709 |
| 0 | 4.817 |
| 5 | 4.229 |
| 10 | 3.81 |
| 15 | 3.399 |
| 20 | 3.056 |
| 25 | 2.775 |
| 30 | 2.543 |
| 35 | 2.36 |
| 40 | 2.235 |
| 45 | 2.152 |
| 50 | 2.122 |
| 55 | 2.117 |
| 60 | 2.113 |
| 65 | 2.113 |

| Length measured | Length (mm) |
|---|---|
| Initial | 51 |
| Final | 52 |

| Quarter | With PVP | Without PVP | wt % PVP in piece |
|---|---|---|---|
| 1 | 0.507 | 0.418 | 17.6 |
| 2 | 0.519 | 0.421 | 18.9 |
| 3 | 0.569 | 0.461 | 19.0 |
| 4 | 0.516 | 0.427 | 17.2 |
| Total | 2.111 | 1.727 | 18.2 |
| Total expected | 2.113 | 1.709 | |

Table 3 showed that the 15% PVP coated graft took over an hour to dry fully in ambient air, it also showed that there was a slight increase in the length of the graft after being coated, washed and dried. After drying, the samples averaged 18.2 weight percent PVP. Further, the distribution of PVP among the samples was substantially consistent. Graft samples or pieces 2 and 3 had slightly higher PVP levels. These pieces had a seam of the graft on them, so it appeared that the seam was probably absorbing more PVP. Thus, about 15 to about 21 weight percent PVP was deposited onto the graft when immersed in the 15% PVP solution.

Results: 10% PVP Profile

TABLE 4

| Time (min) | Weight (g) |
|---|---|
| Dry | 1.699 |
| 0 | 4.891 |
| 5 | 4.292 |
| 10 | 3.881 |
| 15 | 3.491 |
| 20 | 3.159 |

TABLE 4-continued

| | |
|---|---|
| 25 | 2.849 |
| 30 | 2.580 |
| 35 | 2.124 |
| 40 | 2.040 |
| 45 | 2.000 |
| 50 | 1.994 |
| 55 | 1.994 |

| Length measured | Length (mm) |
|---|---|
| Initial | 48 |
| Final | 51 |

| Quarter | With PVP | Without PVP | wt % PVP in piece |
|---|---|---|---|
| 1 | 0.543 | 0.469 | 13.6 |
| 2 | 0.598 | 0.51 | 14.7 |
| 3 | 0.394 | 0.334 | 15.2 |
| 4 | 0.459 | 0.394 | 14.2 |
| Total | 1.994 | 1.707 | 14.4 |
| Total expected | 1.994 | 1.699 | |

Table 4 showed that the 10% PVP covered graft took just under an hour to dry completely, and that the 10% PVP solution covering, washing and drying had also caused a slight increase in the length of the graft. The slightly higher weight % of PVP in pieces 2 and 3 also suggested that the seam of the graft absorbed more of the PVP than the rest of the graft. After drying, the samples averaged 14.4 weight percent PVP. Thus, about 10 to about 18 weight percent PVP was deposited onto the graft when immersed in the 10% PVP solution.

Results: 5% PVP Profile

TABLE 5

| Time (min) | Weight (g) |
|---|---|
| Dry | 1.514 |
| 0 | 3.197 |
| 5 | 2.735 |
| 10 | 2.385 |
| 15 | 2.070 |
| 20 | 1.820 |
| 25 | 1.650 |
| 30 | 1.590 |
| 35 | 1.588 |
| 40 | 1.588 |

| Length measured | Length (mm) |
|---|---|
| Initial | 47 |
| Final | 47 |

| Quarter | With PVP | Without PVP | wt % PVP in piece |
|---|---|---|---|
| 1 | 0.357 | 0.348 | 2.5 |
| 2 | 0.423 | 0.406 | 4.0 |
| 3 | 0.432 | 0.412 | 4.6 |
| 4 | 0.371 | 0.354 | 4.6 |
| Total | 1.583 | 1.52 | 4.0 |
| Total expected | 1.588 | 1.514 | |

Table 5 showed that the 5% PVP covered graft took the least time to dry completely, and that its length did not seem to alter after coating, washing and drying, the PVP did to a minor degree to 'sink' to the bottom of this graft. Thus, about 2 to about 8 weight percent PVP was deposited onto the graft when immersed in the 5% PVP solution.

Conclusions

The 15% PVP covered graft took the most time to dry by approximately 25 minutes. In terms of drying evenly anyone of these concentrations was acceptable.

Various drying techniques are suitable for use with the present invention. For example, textile grafts and/or textile substrates may be dried at room temperature to remove the solvent(s) from the deposited masking agent solution and/or from the sealant solution. Forced air, such as use of a fan or fans or other sources of air movement and/or sources of pressurized air, may be used to facilitate drying. The forced air, if any, may be applied at any suitable angle or combination of angles. The air may or may not flow into the interior lumen of the graft. For example, forced air may be directed towards outer surface of a tubular graft, either perpendicularly, substantially perpendicularly, at an acute angle, and/or at an obtuse angle. Moreover, forced air may be directed towards the interior lumen of the tubular graft, such as towards one open end of the tubular graft, or even from within the interior lumen of the tubular graft. The direction of air flow and the amount of extend of the air flow may be varied to control drying times and even to control resultant physical properties of the graft. Forced air flow may also be useful in aiding migration of the masking agent towards the interior portions of the graft and away from exterior portions of the graft. In other words the masking agent desirably retracts when drying. This would aid in the securement of the sealant material at the exterior portions of the textile graft while also aiding in the blocking of sealant migration towards the interior portions of the graft. The present invention, however, is not limited to the use of air as a drying medium, and other suitable media, including gaseous media, may be used. Further, the present invention is not limited to room temperature drying, and elevated drying temperatures above room temperature may suitably be used.

Moreover, a fluid, such as water, including heated water, may be used with the present invention as described below. The use of heated water aids in the removal of the water-soluble masking agent from the textile product. Further, the use of heated water may also aid in curing of the sealant or sealing agent.

Furthermore, drying and/or curing the sealant material may also be controlled using forced air or other medium, ambient forced air or other medium, heated forced air or other medium, non-forced ambient air or other medium, non-forced heated air or other medium, and the like. Not only may curing times of the sealant material be controlled, but also, to some extent, the properties of the sealant layer may be controlled. The sealant material may be selected, dried or cured, and or selectively deposited, such that the sealant material, as is cures, shrinks about the textile substrate, e.g., the outer surface of the textile graft.

Masking Agent Removal Tests

Different washing methods for the grafts were performed to determine which method would extract the highest levels of PVP and if the chosen method has any effect on the length and crimp of the graft.

Two wash processes were considered, an Ultrawave ultrasonic bath and a domestic washing machine.

Procedures

Part 1: No Sealant Coating

This trial was first done on 6 grafts that were not coated with silicone in order to establish if 100% of the PVP could be removed with the chosen washing methods.

Grafts were prepared by cutting approximately 6×60 mm lengths of commercial woven grafts. All 6 grafts were measured, weighed, and labelled with notches cut into the side. A 15% PVP solution was made with 15 g of PVP and 100 mL of water. All 6 samples were submerged in the 15% PVP in solution. All 6 samples were dried vertically near a running fan. All dried samples were weighed.

An ultrasonic bath was set to 40 degrees Celsius. Samples 1, 2, and 3 were submerged into the ultrasonic bath. Samples 1-3 were left in the ultrasonic bath for 15 minutes. These samples were removed from the ultrasonic bath and were dried vertically near a fan. The dried 1-3 samples were weighed and their lengths were measured and recorded.

Samples 4, 5, and 6 were placed in a washing bag and then into a washing machine. The washing machine was set to a 40 degrees Celsius, 800 RPM, 51 minute wool wash setting. Samples 4-6 were removed from the washing machine and were allowed to dry. Samples 4-6 were weighed and their lengths were recorded.

Part 2: Silicone in Heptane Sprayed Sealant Coating

Samples 1-3 were re-washed, dried, measured and weighed. Samples 1-3 were then submerged in the 15% PVP solution. All 6 samples were dried vertically near a running fan. The dried samples were weighed.

All 6 samples were stretched out and sprayed with silicone in heptane coating. The 6 samples were then allowed to return to their relaxed states under a fume hood and were allowed to dry. An ultrasonic water bath was set to 40 degrees Celsius. Once dry, samples 1-3 were submerged in the ultrasonic bath for 15 minutes. These samples were removed from the bath and were dried vertically near a fan. The dried samples 1-3 were weighed, and their lengths were measured and recorded.

Once dry, samples 4-6 were placed in a washing bag and then into a washing machine. The washing machine was set to a 40 degree Celsius, 800 RPM, 51 minute wool wash setting. The samples were removed from the washing machine and were allowed to dry. Once dry, the samples 4-6 were weighed, and their lengths were measured and recorded.

Results

TABLE 6

| | No Sealant Coating | | | | | |
| --- | --- | --- | --- | --- | --- | --- |
| | Ultrasonic Bath at 40 Degrees | | | Washing Machine Wool Setting | | |
| Measurement | Sample 1 | Sample 2 | Sample 3 | Sample 4 | Sample 5 | Sample 6 |
| Initial Weight (g) | 2.747 | 3.177 | 2.456 | 2.641 | 2.772 | 2.846 |
| Dried PVP weight (g) | 3.508 | 4.048 | 3.179 | 3.445 | 3.568 | 3.658 |
| Washed Weight (g) | 2.779 | 3.212 | 2.467 | 2.641 | 2.772 | 2.847 |
| PVP left (g) | 0.032 | 0.035 | 0.011 | 0.000 | 0.000 | 0.001 |
| Initial Length (mm) | 62.5 | 61 | 57 | 57 | 56 | 63.5 |
| Final Length (mm) | 62.5 | 62 | 57 | 57 | 56 | 63.5 |

The majority of the samples that were put in the washing machine were cleared of PVP while the samples that were put in the ultrasonic bath all still had some minor PVP on them after washing.

TABLE 7

| | Silicone in Heptane Sprayed Sealant Coating | | | | | |
| --- | --- | --- | --- | --- | --- | --- |
| | Ultrasonic Bath at 40 Degrees | | | Washing Machine Wool Setting | | |
| Measurement | Sample 1 | Sample 2 | Sample 3 | Sample 4 | Sample 5 | Sample 6 |
| Initial Weight (g) | 2.747 | 3.177 | 2.456 | 2.641 | 2.772 | 2.847 |
| Dried PVP weight (g) | 3.510 | 3.911 | 3.123 | 3.389 | 3.538 | 3.57 |
| Dried PVP + Coating weight (g) | 3.737 | 4.08 | 3.323 | 3.583 | 3.843 | 3.825 |
| Washed Weight (g) | 2.779 | 3.212 | 2.467 | 2.641 | 2.772 | 2.847 |
| Silicone applied (g) | 0.227 | 0.169 | 0.200 | 0.194 | 0.305 | 0.255 |
| PVP + silicone left on graft (g) | 0.252 | 0.186 | 0.214 | 0.206 | 0.312 | 0.266 |
| PVP left (g) | 0.025 | 0.017 | 0.014 | 0.012 | 0.007 | 0.011 |
| Initial Length (mm) | 62.5 | 61 | 57 | 57 | 56 | 63.5 |
| Length after coating (mm) | 81 | 79 | 73 | 79 | 79 | 79 |
| Final Length (mm) | 70 | 66 | 62 | 61 | 64 | 65 |
| Ratio of PVP Applied to Silicone Applied, wt./wt. | 3.4 | 4.3 | 3.3 | 3.9 | 2.5 | 2.8 |
| Ratio of Silicone Applied to PVP Applied, wt./wt. | 0.29 | 0.23 | 0.30 | 0.26 | 0.40 | 0.36 |

TABLE 7-continued

| | Silicone in Heptane Sprayed Sealant Coating | | | | | |
|---|---|---|---|---|---|---|
| | Ultrasonic Bath at 40 Degrees | | | Washing Machine Wool Setting | | |
| Measurement | Sample 1 | Sample 2 | Sample 3 | Sample 4 | Sample 5 | Sample 6 |
| Percent PVP Removed, wt. % | 96.7 | 97.7 | 97.9 | 98.4 | 99.1 | 98.5 |

Although there was some PVP left on the grafts that went in the washing machine, there is significantly less PVP left on them as opposed to the grafts washed in the ultrasonic bath. In all cases, greater than about 90 weight percent of the PVP was removed. Indeed, in all cases greater than about 95 weight percent of the PVP was removed.

In Table 7, the weight ratio of PVP to silicone applied varied from about 2.5:1.0 to about 4.3:1.0. Conversely, the weight ratio of silicone to PVP applied varied from about 0.40:1.0 to about 0.23:1.0.

Further, ratios are described in Table 11 below.

The ratios described in Tables 7 and 11 are non-limiting.

The weight ratio of PVP (or other masking agents) to silicone (or other sealant agents) may vary from about 10:1 wt. PVP (or other masking agents)/wt. silicone (or other sealant agents) to about 0.01:1 wt. PVP (or other masking agents)/wt. silicone (or other sealant agents), desirably from about 1:1 wt. PVP (or other masking agents)/wt. silicone (or other sealant agents) to about 0.05:1 wt. PVP (or other masking agents)/wt. silicone (or other sealant agents), more desirably from about 0.5:1 wt. PVP (or other masking agents)/wt. silicone (or other sealant agents) to about 0.1:1 wt. PVP/wt. silicone.

Conversely, the weight ratio of silicone (or other sealant agents) to PVP (or other masking agents) may vary from about 0.1:1.0 wt. silicone (or other sealant agents)/wt. PVP (or other masking agents) to about 100:1 wt. silicone (or other sealant agents)/wt. PVP (or other masking agents, desirably from about 1:1 wt. silicone (or other sealant agents)/wt. PVP (or other masking agents to about 20:1 wt. silicone (or other sealant agents)/wt. PVP (or other masking agents, more desirably from about 2:1 wt. silicone (or other sealant agents)/wt. PVP (or other masking agents to about 10:1 wt. silicone (or other sealant agents)/wt. PVP (or other masking agents.

Mask and Dye Tests

Materials

Fabric—Diameter 22 mm, flat tube twill weave and Diameter 10 mm. Crimped twill weave.

Silicone—NuSil Med16-6606 (Temporary implant grade).

Solvent—n-Heptane, 50:50 with silicone dispersion.

Dye—Easy Composites Royal blue pigment for RTV silicone, mixed to approx. 10% of silicone solid content.

Sample Description

For Flat 22 mm fabric samples, the following masking agent formulations were used:

71 A—Bare Fabric
71 B—6% PVP
71 C—6% PVP+1.5% Glycerol (by volume of Mask solution)
71 D—6% PVP+1.5% Glycerol+4% PVP (Total 10% PVP)

The #71B-D flat fabric samples were immersed into the PVP solution and then removed. All #71 samples were mounted on suspended mandrels (Post masking, Pre-coating).

For Crimped Diameter 10 mm fabric samples, the following masking agent formulations were used:

70 A—Bare Fabric
70 B—6% PVP
70 C—6% PVP+1.5% Glycerol (by volume of Mask solution)
70 D—6% PVP+1.5% Glycerol+4% PVP (Total 10% PVP)

The #70B-D crimped fabric samples were immersed into the PVP solution and then removed. All #70 samples were mounted on suspended mandrels (Post masking, Pre-coating).

Masking Agent Preparation

Masking agents were prepared using the same method as described above, with the additional steps to add glycerol for samples B and C (both #70 and #71) and then additional PVP for samples D (both #70 and #71).

Measured the target weight of PVP into plastic beaker on scale balance. A 100 ml masking agent solution was prepared therefore target mass of 4 g PVP required (4% concentration). Measured the target volume of de-ionised water into a 100 ml plastic measuring cylinder. A 100 ml Mask solution to be prepared therefore target volume of 96 ml required. Added de-ionised water into the PVP in plastic beaker. Placed magnetic stirrer in the water and place the beaker on the magnetic stirrer. Turned the magnetic stirrer on at a speed of 350-450 RPM, ensuring the stirrer is centred in the beaker. The stirring was done at room temperature. Stirring was continued until there was no visible PVP solute, or for a minimum of at least 2 minutes. After stirring the masking agent solution was removed from stirrer and used for graft preparation, samples B.

Additional steps were used for samples C, i.e. added glycerol. Returned the plastic beaker to scale balance, tared, and added required quantity of glycerol to the mask agent solution. The target glycerol content was 1.5% by volume of masking agent solution. This corresponded to a target weight of 1.5 g. (Note this corresponded to 25% Glycerol to PVP). Set beaker on stirrer and stirred for at least 2 minutes. This masking agent solution used for samples C.

Additional steps were used for samples D, i.e., additional PVP. Returned the plastic beaker to scale balance, tared, and added the required quantity of PVP to the masking agent solution. The target PVP content was 10% by volume of Mask solution. This corresponded to an additional 4 g PVP added. (Note this effectively reduced the glycerol to PVP ratio from 25% to 15%). This masking agent solution was used for samples D.

Sealant Preparation

The silicone sealant dispersion as-supplied had a 30% solid content, the dispersion was diluted by an additional 100% of solvent. This reduced the solid content to 15%. Additionally, a blue dye was added to the silicone dispersion to provide a visual indication of the coverage and depth of penetration of silicone into the fabric structure.

In particular, 20 ml of silicone dispersion was measured out from its container, in the as-supplied state, and placed into a plastic beaker. An additional 20 ml of n-Heptane solvent was added. The mixture was beaked and was set on scales, tared, and drops of dye were added using dropper. The recommended dye concentration range was 0.3% to 5%, depending of section thickness, therefore a target of 5% was set in order to provide a strong blue colour for visualization. A deviation from this target was due to a calculation of the solid content being at 30% rather than 15%, therefore the actual concentration of dye to silicone was 10% rather than 5%.

Sample Preparation

The individual samples were prepared with masking agent formulations according to the following table.

TABLE 8

|  | No Mask | 6% PVP | 6% PVP + Glycerol (@25% of PVP) | 10% PVP + Glycerol (@15% of PVP) |
|---|---|---|---|---|
| Flat Fabric | 71A | 71B | 71C | 71D |
| Crimped Fabric | 70A | 70B | 70C | 70D |

Samples B-D were immersed in the mask agent solution, as per the above table. The samples were assembled onto mandrel such that each fabric was held at diameter by sized end bungs, but remained unsupported on the inner surface. The inner surface of each fabric was not in contact with the mandrel to avoid affecting mask performance, location and concentrations.

Dispersion drop assessment was undertaken as described below.

Each sample was fully coated with at least 2 coats of silicone dispersion. The intention was to ensure sufficient silicone was present on the outer surface to effect a suitable coverage without concerns for lack of silicone during visual evaluations. Brush coating was done onto a rotating graft on rotisserie at approximately one revolution per second. Grafts were left overnight for solvent evaporation. Grafts were left to fully cure for recommended 72 hrs before being removed from mandrel for washing. The grafts were then placed in a delicate bag and put on 95° C. Tumble Machine Wash cycle for approximately 2 hours 30 mins.

Samples were masked, coated, washed and cut opened flat.

Dispersion Drop Assessment

Prior to full coating, a single drop of polymer dispersion was applied to each sample, and video recorded in order to visually assess if there were noticeable differences in the behaviour of the dispersion on the masked fabric.

Sample A—No Mask. Slow spread of the single drop of polymer dispersion across fabric. Appeared to be soaking into and through fabric Sample B—6% PVP Mask. Rapid spread of the single drop of polymer dispersion across fabric. Appeared to spread more readily than soaking into and through fabric Sample C—6% PVP+1.5% Glycerol Mask. First drop of the single drop of polymer dispersion had rapid spread across fabric. The second drop of the single drop of polymer dispersion was inconclusive, possibly due to sagging fabric holding the pool.

Sample D—10% PVP+1.5% Glycerol Mask. Inconclusive—possibly due to sagging fabric holding the pool Dispersion Drop Assessment across face of the graft Sample A—No Mask. Slower spread of the single drop of polymer dispersion across fabric. Appeared to soak into fabric.

Sample B—6% PVP Mask. Rapid spread of the single drop of polymer dispersion across fabric. Coverage was more uneven with pooling of dispersion in valleys.

Sample C—6% PVP+1.5% Glycerol Mask. Fabric clearly resisted dispersion soaking in.

Sample D—10% PVP+1.5% Glycerol Mask. Fabric clearly resisted dispersion soaking in.

In summary, this Dispersion Droplet Assessment showed that even the lower concentration of masking agent, (Samples B, 6% PVP), appeared to initiate a significantly different response when compared to a non-masked fabric.

A "pooling" effect was seen on the flat fabrics, samples 71C, 71D, was most likely a result of the excess dispersion being unable to run off the fabric or through the fabric. This effect was perhaps also evident in the crimped fabric, particularly Samples 70B, 70D, where there was pooling of the dispersion in the valleys, highlighted by the darker colour, unlike the non-masked sample 70 A, which appears far more uniform in colour/coverage.

Assessment of Sealant Coverage and Penetration

Following the wash cycle to remove the masking agent the grafts were cut lengthways to provide visualization of inner and outer surfaces. Each graft was visualized under optical microscopy on: (a) the outer surface—to confirm presence and uniformity of sealant coating; (b) the inner surface—to confirm presence or ingress of blue silicone, either through the fabric or between the yarn filaments; and (c) sectional view—to assess the level of penetration through the yarn bundles.

Results

Both samples without mask appeared to have permitted the dyed blue silicone dispersion into the yarn bundles and penetrate to the inner surface while the application of the mask appears to have prevented this ingress on all samples.

TABLE 9

|  | Mask Applied | Penetration of Polymer to Inner Surface |
|---|---|---|
| Flat Fabric Samples | | |
| 71A | None | Yes |
| 71B | 6% PVP | No |
| 71C | 6% PVP + Glycerol | No |
| 71D | 10% PVP + Glycerol | No |
| Crimped Fabric Samples | | |
| 70A | None | Yes |
| 70B | 6% PVP | No |
| 70C | 6% PVP + Glycerol | No |
| 70D | 10% PVP + Glycerol | No |

Figure 10A:
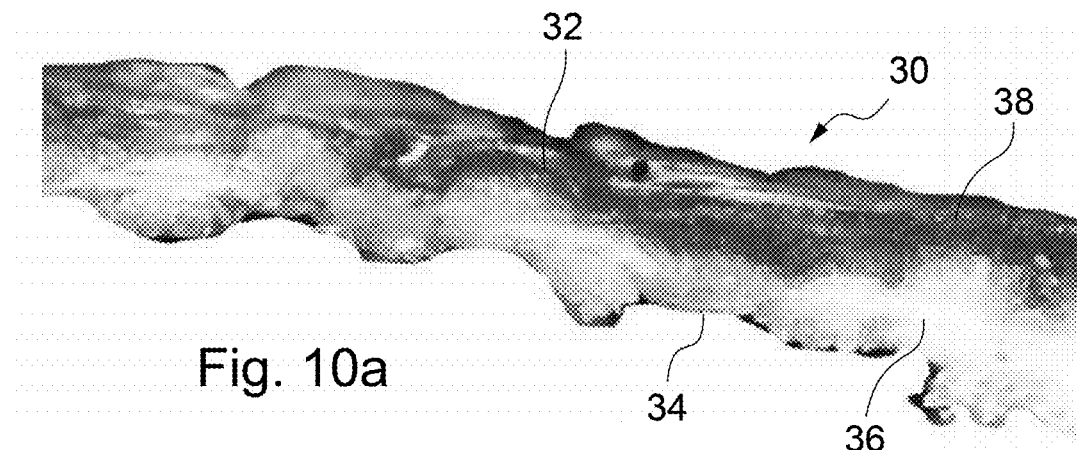
FIG. 10a is a photograph of a cross-section of a textile graft of the present invention showing sealing layer or coating on outer surface portions of the textile graft and showing the inner surface portions of the textile graft being substantially free of any sealing layer or coating.
Figure 10B:
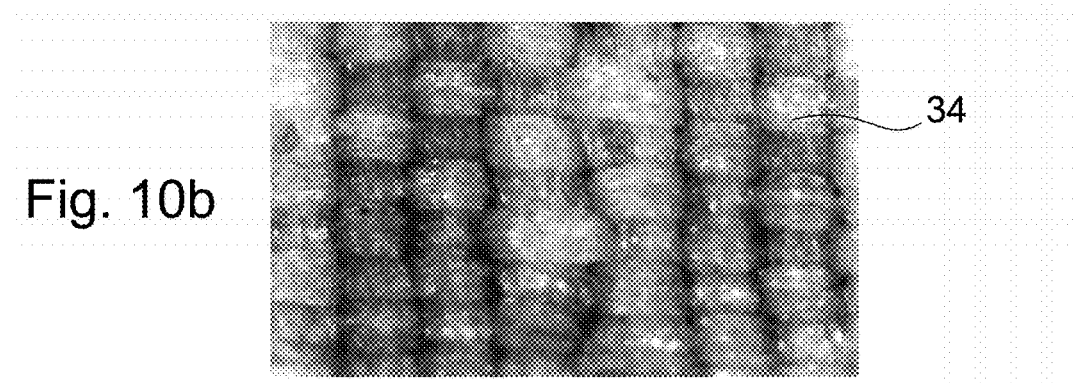
FIG. 10b is a photograph of a portion of the inner surface of the textile graft of FIG. 10a showing the inner surface portion of the textile graft being substantially free of any sealing layer or coating.
Figure 10C:
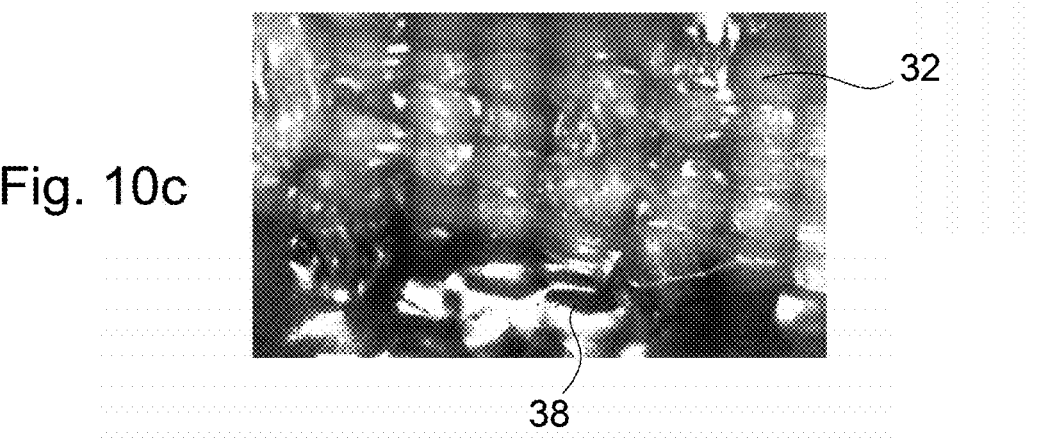
FIG. 10c is a photograph of a portion of the outer surface of the textile graft of FIG. 10a showing the outer surface portion of the textile graft being substantially covered with the sealing layer or coating.

Photographs of crimped fabric sample 70D are provided in FIGS. 10a-10c. FIG. 10a is a photograph of a portion of the cross-section of the tubular wall of the crimped fabric sample 70D. As shown in FIGS. 10a-10c, the fabric sample or textile graft 30 includes an outer textile surface 32, an opposed inner textile surface 34, and a textile wall 36 disposed therein between. As shown in FIGS. 10a and 10c, a sealing layer or coating 38 is disposed over the outer surface 32. Moreover, as shown in FIG. 10a, the sealing layer or coating 38 extends into a portion of the textile wall. As shown in FIGS. 10a and 10b, the inner surface 34 is substantially, including completely, free of the sealing layer or coating 38.

Figure 11:
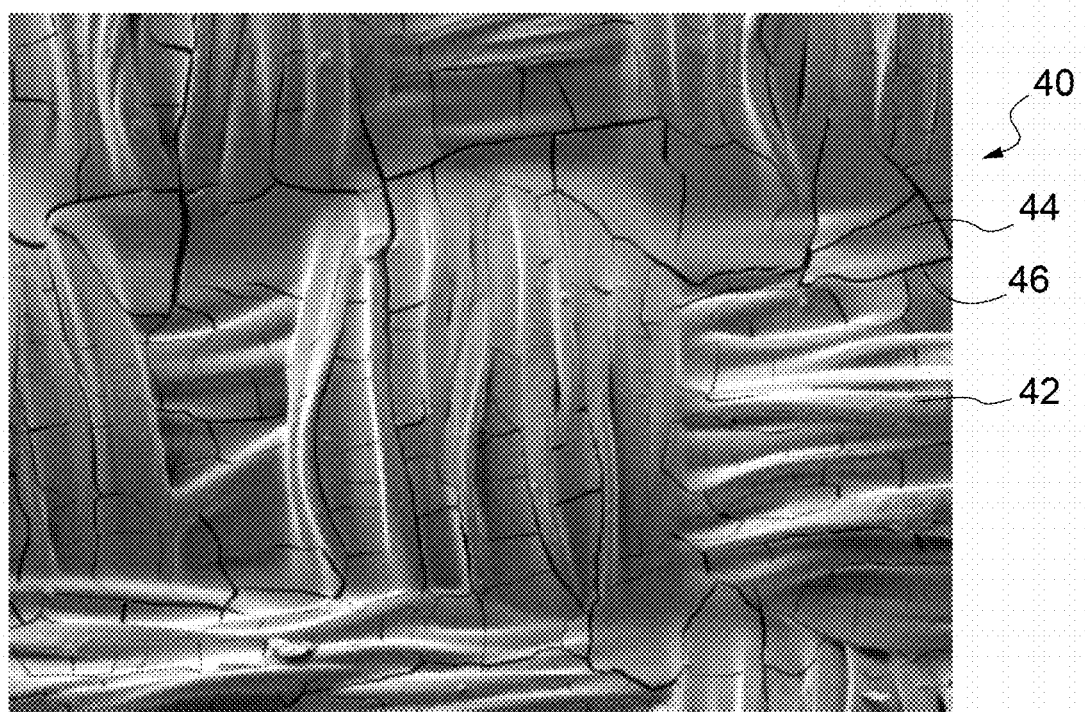
FIG. 11 is a photograph of a dried 40% PVP masking agent concentration applied to a graft sample.

FIG. 11 shows a microphotograph or scanning electron microscope (SEM) photograph of a dried 40% PVP masking agent concentration applied to a graft sample 40. The dried masking agent slurry 44 gathered and encapsulated the yarn structure 42 and had cracks 46. It is evident that the silicone sealant would not be able to effect any permanent adhesion or encapsulation onto this surface fully encapsulated by the masking agent.

The masking agent solution may encapsulate whole yarn bundles and individual yarn fibers, depending on the concentration of the masking agent solution. The higher concentrated masking agent solution (i.e. >30% w/w PVP, >20% w/w of PVP glycerol in water) seems to be too thick to flow into the yarn bundles and coat individual fibers, as seen in FIG. 11. Additionally, high concentrations of masking solution dries as a thick, brittle mask layer, in which many samples develop micro cracks 46 throughout the masking layer 44, as seen in FIG. 11. If the masking agent solution concentration is low (<10% w/w PVP, with or without glycerol in water), the masking agent may encapsulate the yarn bundle and individual fibers, however, a limitation of using a low concentration of masking agent solution may be lack of complete, consistent coverage around each yarn bundle and/or fiber. If this is the case, portions of the fiber are exposed for a surface for potential sealant attachment. Some results show, using low concentrations of masking agent solution, the sealant encapsulates and traps the masking layer; therefore, the masking is not fully washed out of the final product. The key of an appropriate masking solution that works is to have a controlled application process of a targeted concentration for each application as set forth by the present invention.

The overall mechanism of masking agent may include two main concepts, depending on the size of the void or gap: (1) a physical effect for macro pathways (i.e. voids between yarn bundles) and (2) chemical effect for micro pathways (i.e. voids between fibers and voids in micro cracks within the masking layer).

(1) Physical Effect: Filling macro pathways is based on the physical ability for the masking agent solution to penetrate and flow into large voids between the yarn bundles. When the yarn bundles are completely encapsulated with a masking agent layer, the masking agent layer fills the voids between each yarn bundle and blocks entry into the yarn bundle. In turn, the sealant would not be able to penetrate within the macro pathways between each yarn or micro pathways between each fiber due to the presence of masking to fill these voids.

(2) Chemical Effect: For micro pathways throughout the textile, whether micro pathways refer to micro cracks within the masking layer, micro voids between the yarn bundles or micro voids between individual fibers, the chemical mechanism of the masking solution's repulsion effect or ability to repel away from the sealant causes the sealant not to fill the micro voids. The repelling mechanism occurs when the oleophobic sealant tries to come into contact or close proximity with the highly hydrophilic masking layer. This is proven using solution solubility theory and solubility parameters developed by Joel H. Hildebrand. SI Hildebrand values ($\partial[SI]$) demonstrate the masking solution and sealant solubility parameters indicating the solvency behavior of their specific solvents when they come into contact with one another. As noted in the Handbook of Solubility Parameters, CRC Press, 1983, the solvents in the masking solution (water and glycerol) are on the hydrophilic end of the solubility parameter range, whereas the solvent of the sealant (Heptane) is on the opposite end of the solubility parameter range. The $\partial[SI]$ of water is 48.0, $\partial[SI]$ of glycerol is 36.2, and $\partial[SI]$ n-Heptane is 15.3.

Thus, the masking agents of the present invention hinder undesirable migration of the sealant through, physical (e.g., blocking) and repulsion mechanisms. Thus, it may be desirable to use a sealant(s) whose solvent(s) has a solubility parameter of less than about 20 $\partial[SI]$, for example from about 10 $\partial[SI]$ to about 20 $\partial[SI]$ and a masking agent solution(s) whose solvent(s) has a solubility parameter of greater than about 30 $\partial[SI]$, for example from about 30 $\partial[SI]$ to about 50 $\partial[SI]$.

Conclusions

The use of blue dye in the silicone dispersion provided an excellent visual assessment of silicone penetration into the fabric. Both samples coated without prior mask application demonstrated substantial ingress of blue silicone sealant through the fabric to the inner surface. All three masking agent formulations appeared to substantially prevent ingress of silicone to the inner surface.

Silicone Sealing Tests for Commercial Vascular Grafts

The following equipment and materials were used to test sealing commercial grafts according to the present invention.

8 mm crimped polyester fabric commercial graft 14 mm crimped polyester fabric commercial graft Polyvinylpyrrolidone (PVP) Powder NuSil MED-6606 RTV Silicone N-Heptane Royal Blue Pigment De-ionised water Magnetic Stirrer Coating Variable Ranges The following values were used for the testing of the inventive sealing techniques of the present invention.

PVP concentration in de-ionised water was varied on a weight basis at 1%, 2%, 4%, 6%, 8%, 10%, 15%, 20%, 25%, and 30%.

Glycerol and silicone dispersion concentration was tested at PVP concentrations of 4%, 8%, 15%, and 30%. Glycerol concentrations were used on PVP concentrations of 5%, 15%, and 30%. These concentrations were percentage of glycerol to PVP.

The variations of PVP, glycerol, and silicone tested were as follows:

TABLE 10

| Sample | PVP Concentration (%) | | | | | | | | | | Glycerol Concentration (% of PVP) | | | Silicone Concentration (%) | |
|---|---|---|---|---|---|---|---|---|---|---|---|---|---|---|---|
| | 1 | 2 | 4 | 6 | 8 | 10 | 15 | 20 | 25 | 30 | 5 | 15 | 30 | 15 | 30 |
| 1 | X | | | | | | | | | | | | | X | |
| 2 | | X | | | | | | | | | | | | X | |
| 3 | | | X | | | | | | | | | | | X | |
| *4 | | | | X | | | | | | | | | | X | |
| 5 | | | | | X | | | | | | | | | X | |
| 6 | | | | | | X | | | | | | | | X | |
| *7 | | | | | | | X | | | | | | | X | |
| 8 | | | | | | | | X | | | | | | X | |
| 9 | | | | | | | | | X | | | | | X | |
| *10 | | | | | | | | | | X | | | | X | |
| *11 | | X | | | | | | | | | X | | | X | |
| 12 | | X | | | | | | | | | | | X | X | |
| 13 | | | | | X | | | | | | X | | | X | |
| 14 | | | | | X | | | | | | | | X | X | |
| 15 | | | | | | | X | | | | X | | | X | |
| *16 | | | | | | | X | | | | | | X | X | |
| 17 | | | | | | | | | X | | X | | | X | |
| 18 | | | | | | | | | X | | | | X | X | |
| *19 | | X | | | | | | | | | | X | | X | |
| 20 | | X | | | | | | | | | | X | | | X |
| 21 | | | | | X | | | | | | | X | | X | |
| 22 | | | | | X | | | | | | | X | | | X |
| 23 | | | | | | | X | | | | | X | | X | |
| 24 | | | | | | | X | | | | | X | | | X |
| 25 | | | | | | | | | X | | | X | | X | |
| *26 | | | | | | | | | X | | | X | | | X |

*Denotes samples to be applied to both types of grafts, i.e., First and Second graft samples.

Sample Preparation

Each sample was made from of a section of the commercial grafts. The grafts were first cut to length by first fully stretching the graft to remove the crimps, and then a section of 180 mm length was cut with a single edge razor blade. Each sample was weighed.

Mask Preparation

A measured amount of de-ionised water was placed into a 100 ml plastic beaker. A magnetic stirrer was placed into the de-ionised water. While stirring, PVP and glycerol (if any) were added. Stirring continued until there was no solute visible.

Masking Agent Application

The graft samples were coated by immersing the graft samples within the mask solution and agitating the graft by gloved hands, so the samples were fully coated inside and out.

Once the grafts were fully coated, excess mask solution, if any, was removed. Next, each graft was attached to a mandrel by using cable ties. One end of the graft was secured to the mandrel by a cable tie, then the graft was extended to 60% of its overall extended length (108 mm), and the other end of the graft was secured to the mandrel by another cable tie. The mandrel was then placed horizontally on a rotating mount and allowed to air dry. Once dry, the masked grafts were weighed.

Sealant Preparation

The silicone dispersion was supplied as a 30% solid content. Additional amounts of n-Heptane were added to reduce that solid content to 22.5% then 15. A blue dye was added to the silicone dispersion.

Sealant Application

The mandrel with the graft mounted was be placed on the rotary motor to slowly spin the graft. The sealant was applied with a paint brush starting at one end and working to the other end. This was repeated until there was an excess of sealant dispersion on the graft. Once the targeted level of silicone was applied onto the graft, the graft was transferred to a rotating mount and allowed to air dry. Once dry, the sealed graft was weighed.

Masking Agent Removal

Once the grafts were fully dried, the masking agents were removed. This was done by washing the grafts in a washing machine on a 90° C. wash (with no detergent). This caused the PVP to dissolve in the water and thus be removed from the graft. The 90° C. temperature also aided in complete curing of the silicone. When the wash was complete, the grafts were hung up to air dry. After drying, the finished grafts were weighed.

Silicone Adherence

A good coating adhesion can also be demonstrated if the graft coating maintains its integrity in a high pressurised state. Pressure can be used as a measure over all sizes of grafts because most of the overall hoop stress is borne by the stiffer fabric material of the graft. Furthermore, most of the forces acting on the silicone coating for delaminating it happen in the gaps between bundles of fibres as the weave structure does not change for different diameters of graft, then this area and consequently the force acting on that area will be consistent. Therefore, irrespective of the size of graft the same pressure will produce the same force to delaminate the silicone coating.

To ensure the position of the bundles within the fabric are as uniform as possible over all diameters, the fabric was crimp removed so the graft is in its fully extended shape. In accomplishing this, the pressure applied was above the pressure that it takes to fully extend the graft. Since this pressure will be different for each size of graft, the graft that needs the highest pressure to fully extend itself (i.e., the one of smallest diameter) will be used as a worst-case scenario. Once this worst-case pressure is determined, a factor of safety (FOS) is applied and it is this FOS corrected pressure that is used as a minimum requirement for all grafts. If the graft can be pressurised to this FOS corrected pressure with no visual signs of the coating delaminating (bubbles forming), then it can be deduced that the coating has sufficient and acceptable adhesion/integrity.

One method of testing for delamination is as follows:
Connect the graft to a pressure rig, ensuring one end is plugged;
Slowly apply pressure to the graft;
Stop at 120 mmHg (clinical pressure) and look for signs of delamination (bubbles);
Measure the leak rate and record it in mm/cm²/min;
Increase the pressure in increments up to the FOS corrected figure is reached;
If any signs of delamination are visible at any point stop the test, mark as failed;
Hold at the FOS corrected pressure for 1 min; and
If no signs of delamination are present, mark graft as pass.

The following pressure tests were conducted:
The grafts were pressurised with water to observe if there were any signs of the silicone losing its bond from the graft. The pressure was to be increased slowly to a maximum pressure of 600 mmHg. The adherence was noted as follows:

0—Silicone is well adhered to graft and showing no signs of failure;
1—Graft reached the maximum pressure, but the leak rate has visibly increased;
2—Silicone coating has started to fail, showing jets of water coming from the graft; and
3—Silicone coating has failed, and a bubble has appeared on the surface.

Penetration Depth

The effectiveness of the mask was determined by how far the silicone wicked through the fabric. Desirably, the silicone will sit on the outside surface of the graft and not unduly penetrate the graft structure. If the masking agent was not effective, then the silicone was visible within the fabrics and on the inside edge. To visualise this, the grafts were cut lengthways and a cross section was examined under high magnification.

The degree of penetration was noted as follows;
0—Silicone only visible on the outer surface of the graft;
1—Silicone is visible between fibres of the graft but only up to 50% of the thickness;
2—Silicone is visible penetrating to the inside surface; and
3—Silicone visible everywhere, the entire graft structure is blue.

Test Results Summaries

TABLE 11

| | WEIGHT SUMMARIES | | | | | | |
|---|---|---|---|---|---|---|---|
| | | Weight of Graft Segment | | | Amount | | Ratio of |
| Sample Name | Initial (g) | After Masking and Drying (g) | After Sealant and Curing (g) | After Washing and Drying (g) | of Masking Agent Applied (g) | Amount of Sealant Applied (g) | Sealant to Masking Agent (g/g) |
| 1 | 0.703 | 0.714 | 1.496 | 1.485 | 0.011 | 0.782 | 71.1 |
| 2 | 0.714 | 0.739 | 1.484 | 1.46 | 0.025 | 0.745 | 29.8 |
| 3 | 0.741 | 0.779 | 1.436 | 1.392 | 0.038 | 0.657 | 17.3 |
| 4 | 0.673 | 0.721 | 1.239 | 1.182 | 0.048 | 0.518 | 10.8 |
| A4 | 1.089 | 1.159 | 2.31 | 2.229 | 0.07 | 1.151 | 16.4 |
| 5 | 0.689 | 0.778 | 1.199 | 1.1 | 0.089 | 0.421 | 4.7 |
| 6 | 0.698 | 0.778 | 1.216 | 1.129 | 0.08 | 0.438 | 5.5 |
| 7 | 0.694 | 0.813 | 1.454 | 1.319 | 0.119 | 0.641 | 5.4 |
| A7 | 1.026 | 1.198 | 2.047 | 1.86 | 0.172 | 0.849 | 4.9 |
| 8 | 0.695 | 0.864 | 1.492 | 1.31 | 0.169 | 0.628 | 3.7 |
| 9 | 0.688 | 0.939 | 1.541 | 1.276 | 0.251 | 0.602 | 2.4 |
| 10 | 0.663 | 0.969 | 1.537 | 1.207 | 0.306 | 0.568 | 1.9 |
| 11 | 0.739 | 0.778 | 1.382 | 1.339 | 0.039 | 0.604 | 15.5 |
| A11 | 1.08 | 1.119 | 2.086 | 2.041 | 0.039 | 0.967 | 24.8 |
| 12 | 0.658 | 0.712 | 1.262 | 1.201 | 0.054 | 0.55 | 10.2 |
| 13 | 0.717 | 0.83 | 1.486 | 1.368 | 0.113 | 0.656 | 5.8 |
| 14 | 0.719 | 0.816 | 1.463 | 1.357 | 0.097 | 0.647 | 3.7 |
| 15 | 0.717 | 0.853 | 1.513 | 1.367 | 0.136 | 0.66 | 4.9 |
| 16 | 0.701 | 0.888 | 1.502 | 1.298 | 0.187 | 0.614 | 3.3 |
| A16 | 0.896 | 1.103 | 1.731 | 1.503 | 0.207 | 0.628 | 3.0 |
| 17 | 0.738 | 1.067 | 1.879 | 1.531 | 0.329 | 0.812 | 2.5 |
| 18 | 0.719 | 1.183 | 1.881 | 1.395 | 0.464 | 0.698 | 1.5 |
| 19 | 0.705 | 0.754 | 1.502 | 1.446 | 0.049 | 0.748 | 15.3 |
| A19 | 0.878 | 0.924 | 1.682 | 1.632 | 0.046 | 0.758 | 16.5 |
| 20 | 0.717 | 0.759 | 2.063 | 2.016 | 0.042 | 1.304 | 31.0 |
| 21 | 0.709 | 0.809 | 1.46 | 1.355 | 0.1 | 0.651 | 6.5 |
| 22 | 0.741 | 0.844 | 2.121 | 2.007 | 0.103 | 1.277 | 12.4 |
| 23 | 0.715 | 0.855 | 1.487 | 1.333 | 0.14 | 0.632 | 4.5 |
| 24 | 0.688 | 0.867 | 2.03 | 1.846 | 0.179 | 1.163 | 6.5 |
| 25 | 0.711 | 1.057 | 1.818 | 1.451 | 0.346 | 0.761 | 2.2 |
| 26 | 0.699 | 1.038 | 2.464 | 2.115 | 0.339 | 1.426 | 4.2 |
| A26 | 1.356 | 2.058 | 4.448 | 3.689 | 0.702 | 2.39 | 3.4 |

The ratio of sealant to masking agent on a gram to gram or weight dry basis varied from about 1:1 to about 70:1. Useful ratios also include ratios of sealant to masking agent from about 2:1 to about 20:1, including from about 2:1 to about 10:1, on a dry weight basis. These ratios, however are non-limiting. The weight ratio of silicone (or other sealant agents) to PVP (or other masking agents) may vary from about 0.1:1.0 wt. silicone (or other sealant agents)/wt. PVP (or other masking agents) to about 100:1 wt. silicon (or other sealant agents)/wt. PVP (or other masking agents, desirably from about 1:1 wt. silicone (or other sealant agents)/wt. PVP (or other masking agents to about 20:1 wt. silicone (or other sealant agents)/wt. PVP (or other masking agents, more desirably from about 2:1 wt. silicone (or other sealant agents)/wt. PVP (or other masking agents to about 10:1 wt. silicone (or other sealant agents)/wt. PVP (or other masking agents.

TABLE 12

PENETRATION TEST RESULTS

| Sample Number | PVP % | Glycerol as % of PVP | Penetration Grading Scale 0-3 | Comment |
|---|---|---|---|---|
| 1 | 1 | 0 | 3 | |
| 2 | 2 | 0 | 3 | |
| 3 | 4 | 0 | 2 | |
| 4 | 6 | 0 | 2 | |
| A4 | 6 | 0 | 2 | |
| 5 | 8 | 0 | 2 | |
| 6 | 10 | 0 | 1 | |
| 7 | 15 | 0 | 2 | |
| A7 | 15 | 0 | 2 | |
| 8 | 20 | 0 | 2 | |
| 9 | 25 | 0 | 0 | Delaminated |
| 10 | 30 | 0 | 0 | Delaminated |
| A10 | 30 | 0 | | Not Made |
| 11 | 4 | 5 | 2 | |
| A11 | 4 | 5 | 2 | |
| 12 | 4 | 30 | 2 | |
| 13 | 8 | 5 | 2 | |
| 14 | 8 | 30 | 2 | |
| 15 | 15 | 5 | 1 | |
| 16 | 15 | 30 | 0 | |
| A16 | 15 | 30 | 1 | |
| 17 | 30 | 5 | 0 | Delaminated |
| 18 | 30 | 30 | 0 | Delaminated |
| 19 | 4 | 15 | 2 | |
| A19 | 4 | 15 | 2 | |
| 20 | 4 | 15 | 2 | |
| 21 | 8 | 15 | 2 | |
| 22 | 8 | 15 | 1 | |
| 23 | 15 | 15 | 1 | |
| 24 | 15 | 15 | 1 | |
| 25 | 30 | 15 | 0 | Delaminated |
| 26 | 30 | 15 | 0 | Delaminated |
| A26 | 30 | 15 | 0 | Delaminated |

The results, which are tabulated in order of PVP masking agent concentrations, showed a clear correlation between higher levels of PVP and reduced penetration of the silicone sealant into the inner lumen of the graft samples.

In general, PVP mask concentration of 10% or greater prevented the bulk penetration of silicone to more than 50% into the fabric thickness. In some samples, they were small "fingers" or "slivers" of silicone evident between the yarn bundles at the interstices created by warp and weft yarn bundles. Such interstitial silicone represented a very small percentage of the overall inner surface area of the fabric.

Adhesion Test Results

TABLE 13

| Sample Number | PVP (g) | Glycerol as % of PVP | Measured Leakage (ml/min) @120 mmHg Result 1 | Measured Leakage (ml/min) @600 mmHg Result 3 | Adhesion grading Scale 0-3 |
|---|---|---|---|---|---|
| 1 | 1 | 0 | 0 | 0 | 0 |
| 2 | 2 | 0 | 0 | 0 | 0 |
| 3 | 4 | 0 | 0 | 0 | 0 |
| 4 | 6 | 0 | 0 | 4 | 0 |
| A4 | 6 | 0 | 33 | | 3 |
| 5 | 8 | 0 | 19 | | 1 |
| 6 | 10 | 0 | 40 | | 1 |
| 7 | 15 | 0 | 4 | 14 | 0 |
| A7 | 15 | 0 | 31 | | 1 |
| 8 | 20 | 0 | 12 | 46 | 1 |
| 9 | 25 | 0 | Delaminated | | 3 |
| 10 | 30 | 0 | >500 | | 3 |
| A10 | 30 | 0 | | | |
| 11 | 4 | 5 | 0 | 1 | 0 |
| A11 | 4 | 5 | 0 | 5 | 0 |
| 12 | 4 | 30 | 0 | 0 | 0 |
| 13 | 8 | 5 | 9 | 86 | 2 |
| 14 | 8 | 30 | 1 | 22 | 1 |
| 15 | 15 | 5 | 3 | 22 | 1 |
| 16 | 15 | 30 | 1.5 | | 1 |
| A16 | 15 | 30 | 34 | 190 | 1 |
| 17 | 30 | 5 | >1000 | | 3 |
| 18 | 30 | 30 | >1001 | | 3 |
| 19 | 4 | 15 | 0 | 0 | 0 |
| A19 | 4 | 15 | 4 | 27 | 0 |
| 20 | 4 | 15 | 0 | 0 | 0 |
| 21 | 8 | 15 | 0.5 | 5 | 0 |
| 22 | 8 | 15 | 0 | | 3 |
| 23 | 15 | 15 | 1.5 | 11 | 0 |
| 24 | 15 | 15 | 0 | | 3 |
| 25 | 30 | 15 | Delaminated | | 3 |
| 26 | 30 | 15 | Delaminated | | 3 |
| A26 | 30 | 15 | Delaminated | | 3 |

The above results, which are tabulated in order of PVP masking agent concentrations, show a clear correlation between higher levels of PVP and reduced adhesion of the silicone sealant to the fabric. Two mechanisms by which silicone penetrated into the inner surface of the fabric were observed, i.e., either through the yarn bundle fibers or by passing between the gaps in the yarn bundles. The lower concentrations of mask agent (>4% PVP) appeared to inhibit the flow of polymer through the yarn fibers, however it was not in all cases sufficient to substantially prevent the ingress of small "fingers" or "slivers" of silicone polymer between the gaps in the bundles, i.e., interstitial spaces between proximately juxtaposed yarns within the textile pattern. It appeared that slightly larger concentrations of mask agent (>15%) was required to completely block the passage of silicone polymer through between the gaps in the fiber bundles.

Assessment of Handling

The handling characteristics of grafts are the result of a series of complex interactions between the fabric structure, the graft diameter, the crimp pitch and form, the thickness profile of the polymer sealant and the amount of penetration of the sealant into the yarn bundles.

The below assessment parameters, although subjective, aim to consider all of the following: bend radius at kink formation, flexibility, hoop stiffness (ability to remain fully open) and stretching.

A grading score (1-4) was be used to assess handling characteristics;
1—Graft judged more flexible than reference sample.
2—Graft judged comparable to reference sample.
3—Graft judged to be stiffer than reference sample but with useable characteristics.
4—Graft judged too stiff for comparable use.

The reference sample was considered to have excellent overall handling and at least comparable to currently commercially available gelatin sealed grafts.

Polymer Sealant Coverage

The amount of polymer sealant coverage on each sample was reported in mg/cm$^2$ and was calculated by dividing the overall mass of polymer applied to each individual graft by the surface area of the graft. Previous crimped prototypes have demonstrated both effective sealing and suitable handling characteristics with polymer coverages of at least about 8 mg/cm$^2$ ranging up to about 14 mg/cm$^2$. Coverage levels above 14 mg/cm$^2$ increased the overall stiffness of the handling characteristics beyond that of a standard gelatin sealed graft, however increase stiffness and therefore increased amount of polymer coverage may be advantageous for some graft applications.

Tensile Extension Force

Samples were mounted between jaws of Lloyd Tensile Test machine with jaws spacing of 80 mm. The machine was zeroed and the jaws extended by 20% (16 mm) and the maximum measured force was recorded.

The results recorded are tabulated below, ranked in order from low to high for force-to-extend by 20%.

These results demonstrated a strong correlation between handling assessment and force-to-extend, with lower extension forces corresponding to improved handling characteristics.

A review of the polymer coverage values indicated that coverage levels of up to 40 mg/cm$^2$ might be considered in order to achieve comparable handling characteristics to the reference sample (grading 2), as indicated by graft sample #15.

All grafts which demonstrated delamination of the polymer sealant during pressurized adhesion tests are by a note (1) highlighted in italics. This list indicates that poor adhesion can result in low Extension Forces and improved handling characteristics. This result supports the theory that acceptable handling characteristics rely on lower levels of penetration of sealant into the yarn bundles.

TABLE 14

| Sample No. | Dia, mm | Extended Length, mm | Surface Area, cm$^2$ | Polymer Coverage, mg/cm$^2$ | Handling Assessment Grading, 1 to 4 | Force to Extend by 20% (N) |
|---|---|---|---|---|---|---|
| 18 (1) | 8 | 130 | 32.7 | 43 | 1 | 0.29986 |
| 10 (1) | 8 | 125 | 31.4 | 38 | 1 | 0.37938 |
| 5 | 8 | 120 | 30.1 | 36 | 1 | 0.4067 |
| 25 (1) | 8 | 130 | 32.7 | 44 | 1 | 0.41064 |
| 6 | 8 | 135 | 33.9 | 33 | 2 | 0.48247 |
| 16 | 8 | 130 | 32.7 | 40 | 2 | 0.48938 |
| 17 (1) | 8 | 140 | 35.2 | 44 | 1 | 0.52805 |
| 8 | 8 | 130 | 32.7 | 40 | 2 | 0.53074 |
| 7 | 8 | 132 | 33.2 | 40 | 2 | 0.54057 |
| 9 (1) | 8 | 125 | 31.4 | 41 | 1 | 0.57061 |
| 13 | 8 | 140 | 35.2 | 39 | 2 | 0.58817 |
| 4 | 8 | 125 | 31.4 | 38 | 2 | 0.60156 |
| 12 | 8 | 135 | 33.9 | 35 | 3 | 0.69369 |
| 15 | 8 | 135 | 33.9 | 40 | 2 | 0.71933 |
| 14 | 8 | 130 | 32.7 | 42 | 3 | 0.76625 |
| 3 | 8 | 135 | 33.9 | 41 | 3 | 0.78701 |
| 11 | 8 | 130 | 32.7 | 41 | 3 | 0.90773 |
| 1 | 8 | 135 | 33.9 | 44 | 3 | 1.0072 |
| 19 | 8 | 135 | 33.9 | 43 | 3 | 1.0302 |
| 23 | 8 | 140 | 35.2 | 38 | 3 | 1.0372 |
| 2 | 8 | 140 | 35.2 | 41 | 3 | 1.1116 |
| 21 | 8 | 125 | 31.4 | 43 | 3 | 1.1234 |
| 26 (1) | 8 | 134 | 33.7 | 63 | 4 | 1.1571 |
| 22 | 8 | 125 | 31.4 | 64 | 4 | 1.8936 |
| 24 (1) | 8 | 111 | 27.9 | 66 | 4 | 2.1711 |
| 20 | 8 | 115 | 28.9 | 70 | 4 | 3.0235 |
| 64B | 10 | 620 | 194.7 | 12.1 | Reference Sample | |

Note:
(1) demonstrated delamination of the polymer sealant during pressurized adhesion tests Conclusions Acceptable handling characteristics were achieved with lower levels of penetration of sealant into the yarn bundles. The use of the masking agents to limit the amount of polymer penetration into textile fabric can be utilized for improved handling characteristics. Polymer coverage levels of up to 40 mg/cm$^2$ were demonstrated to achieve comparable handling characteristics to the reference sample as assessed by surgeon users.

Photographs of select samples from Tables 10-14 are reproduced in FIGS. 12-19. Description of these figures follow.

Figure 12:
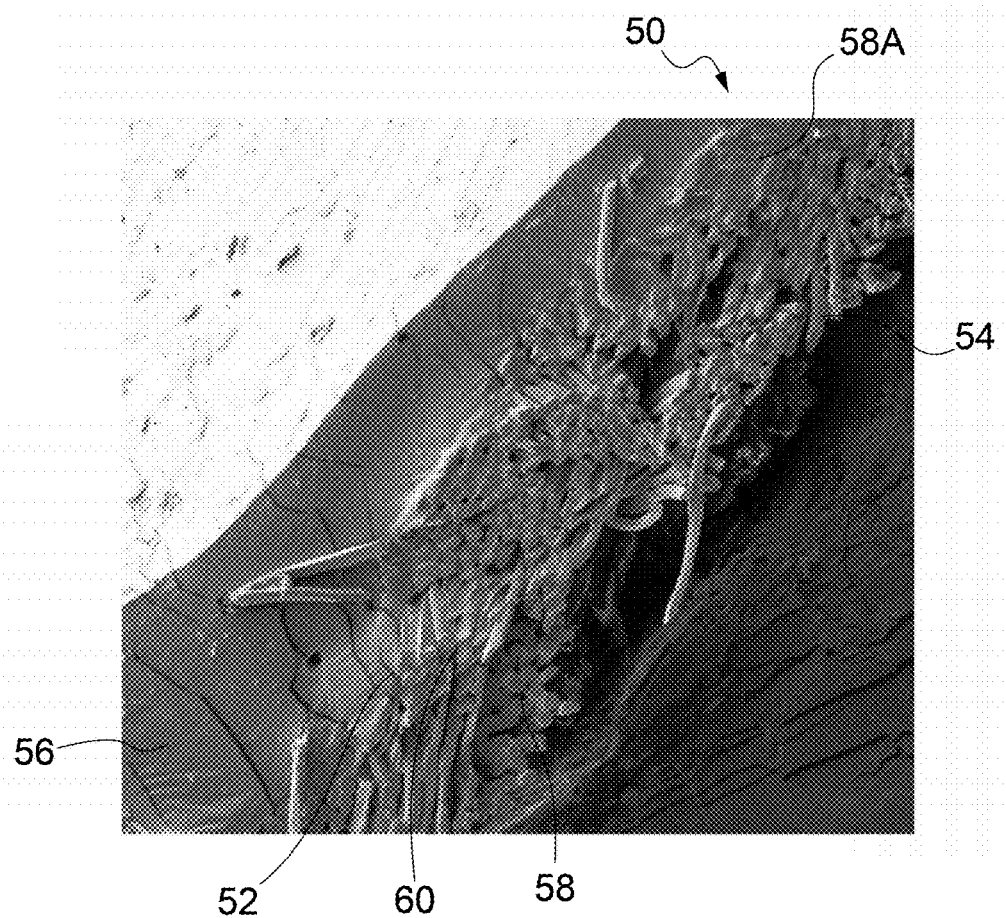
FIG. 12 is a scanning electron microscope (SEM) photograph of a cross-sectional section of textile sample 2, which is described below in conjunction with Tables 10-14.
Figure 13:
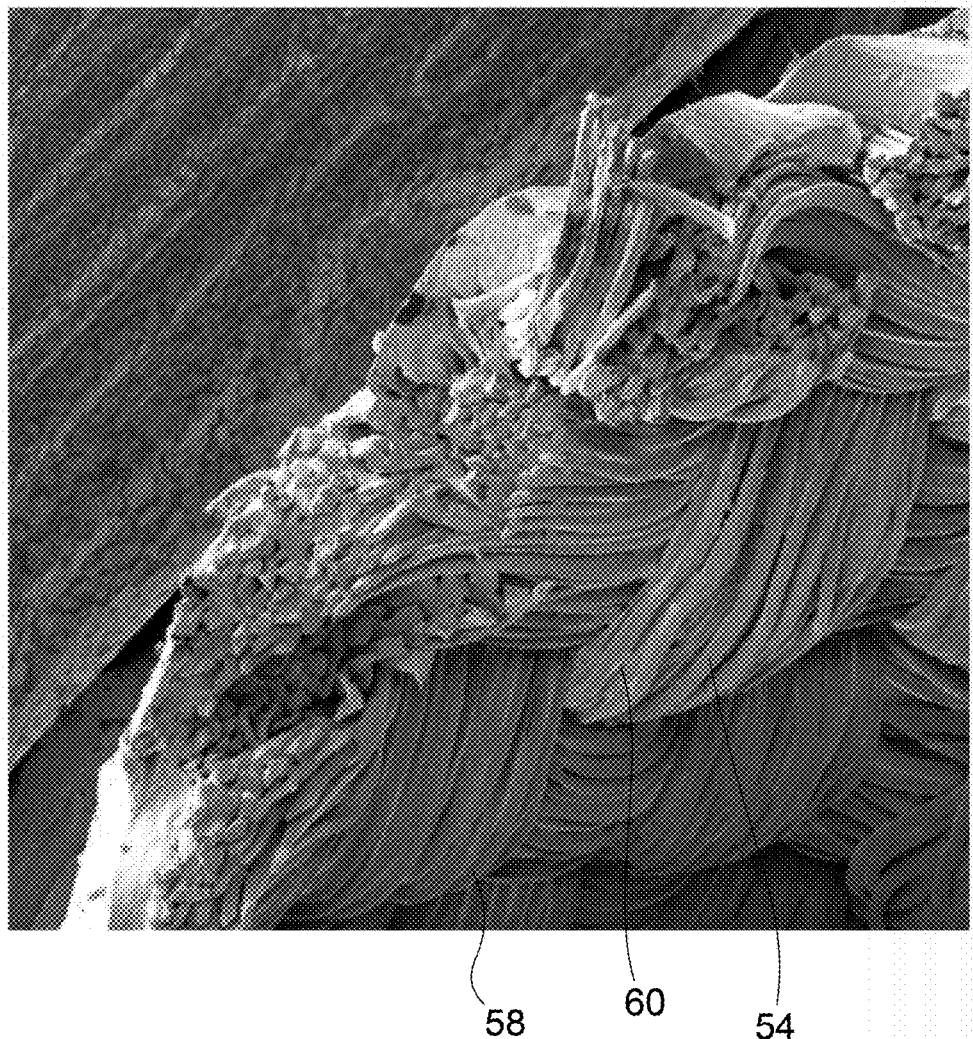
FIG. 13 is a SEM photograph of an inner surface of textile sample 2, which is described below in conjunction with Tables 10-14.

FIGS. 12 and 13 are SEM photographs of sample 2 from the above-described Tables. Sample 2 had the following characteristics:
Masking Solution: 2% PVP, 0% Glycerol in water;
Silicone Dispersant: 15% Silicone in heptane;
Silicone Coverage: 41 mg/cm$^2$;
Silicone Penetration Grading: 3 (Silicone visible);
Silicone Adherence Grading: 0 (Silicone is well adhered to graft and showing no signs of failure);
Measured Leakage at 120 mmHg: 0 ml/min;
Measured Leakage at 600 mmHg: 0 ml/min;
Handling Assessment: 3 (Graft judged to be stiffer than Reference but with useable characteristics); and
Tensile Force to Extend Graft by 20%: 1.112 N.

FIG. 12 is a SEM photograph of a cross-section of the textile 50 of Sample 2. The outer surface 52 of the textile 50 was fully coated with silicone sealant 56. Fiber bundles 58A were fully encapsulated by the silicone sealant 56. The silicone sealant was disposed throughout the cross-section of the fiber bundle or the multi-filament yarn 58. As depicted in FIG. 13, the inner textile surface 54 also had noticeable amounts of silicone sealant 60 at the fiber bundles 58.

Figure 14:
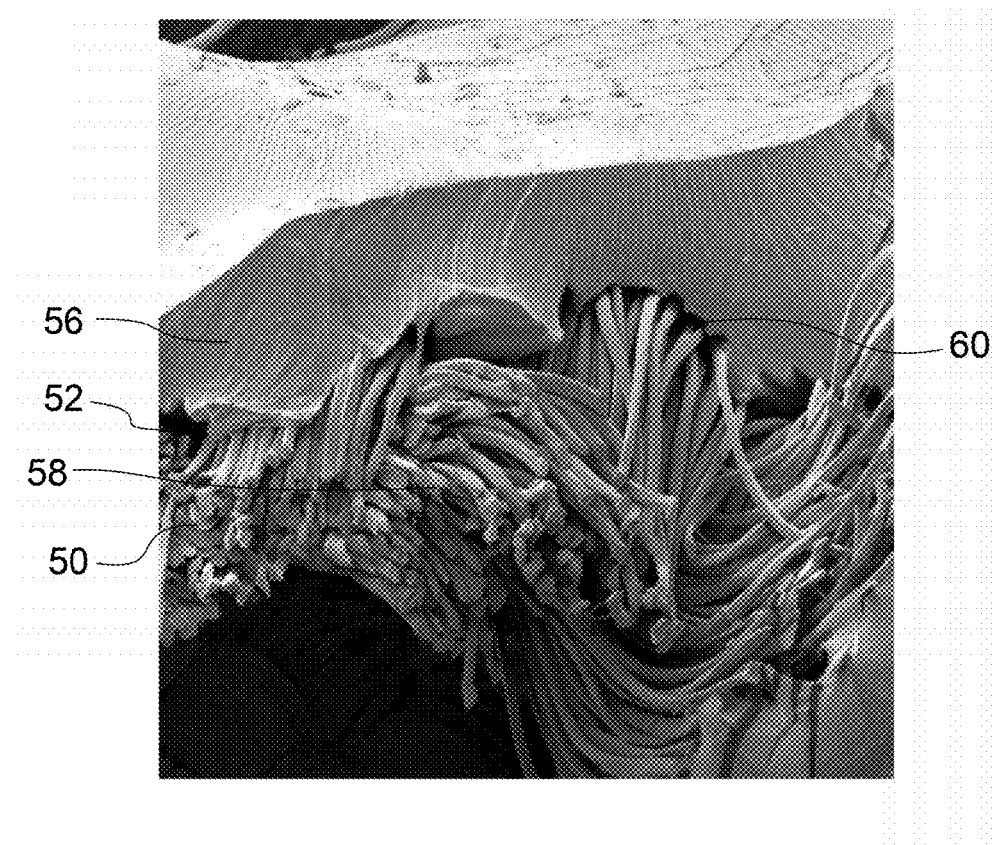
FIG. 14 is a SEM photograph of a cross-sectional section of textile sample 9, which is described below in conjunction with Tables 10-14.
Figure 15:
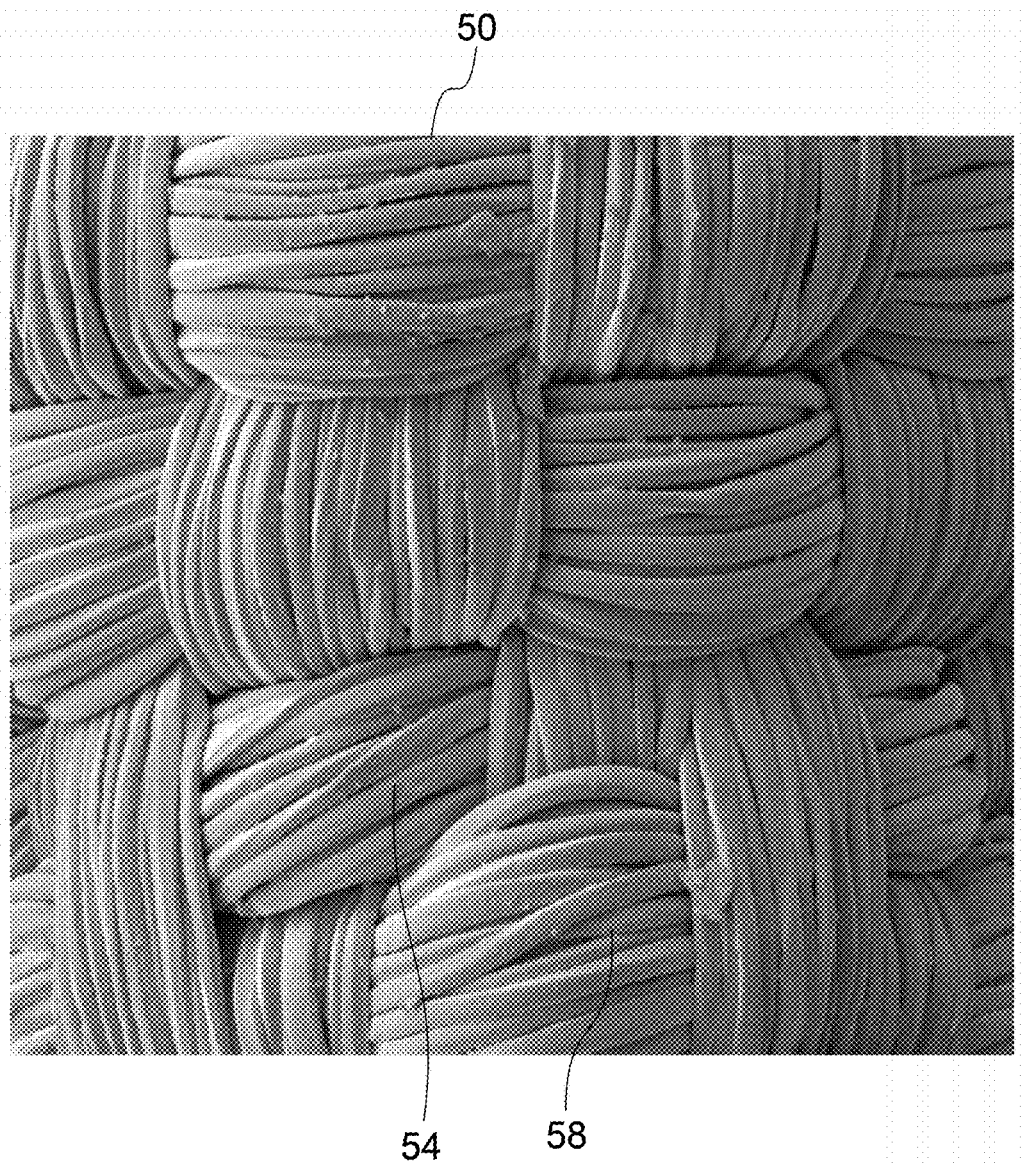
FIG. 15 is a SEM photograph of an inner surface of textile sample 9, which is described below in conjunction with Tables 10-14.

FIGS. 14 and 15 are photographs of sample 9 from the above-described Tables. Sample 9 had the following characteristics:
Masking Solution: 25% PVP, 0% Glycerol in water;
Silicone Dispersant: 15% Silicone in heptane;
Silicone Coverage: 41 mg/cm$^2$;
Silicone Penetration Grading: 0 (Silicone only visible on the outer surface of the graft);
Silicone Adherence Grading: 3 (Delaminated, Silicone coating has failed, and a bubble has appeared on the surface);
Measured Leakage at 120 mmHg: Delaminated;
Measured Leakage at 600 mmHg: Delaminated;

Handling Assessment: 1 (Graft judged more flexible than Reference Sample); and

Tensile Force to Extend Graft by 20%: 0.571 N.

FIG. 14 is a photograph of a cross-section of the textile 50 of Sample 9. The outer surface 52 of the textile 50 was fully coated with silicone sealant 56. Individual textile bundles 58 were general free of silicone sealant penetration. There was, however, delamination of the silicone sealant 56 from the textile fibers at the outer surface as noted by delamination spaces. As depicted in FIG. 15, the inner textile surface 54 and all fiber bundles 58 thereat were free of any noticeable amounts of silicone sealant 60.

Figure 16:
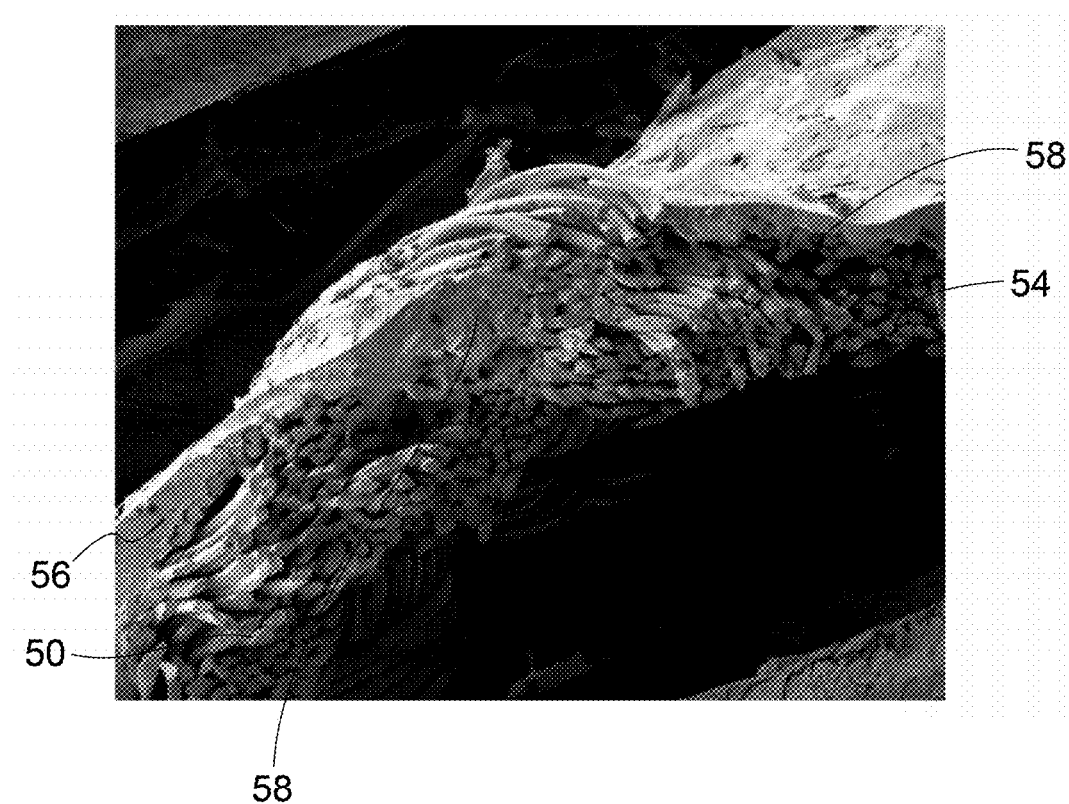
FIGS. 16-18 are SEM photographs of cross-sectional sections of textile sample 7, which is described below in conjunction with Tables 10-14.
Figure 17:
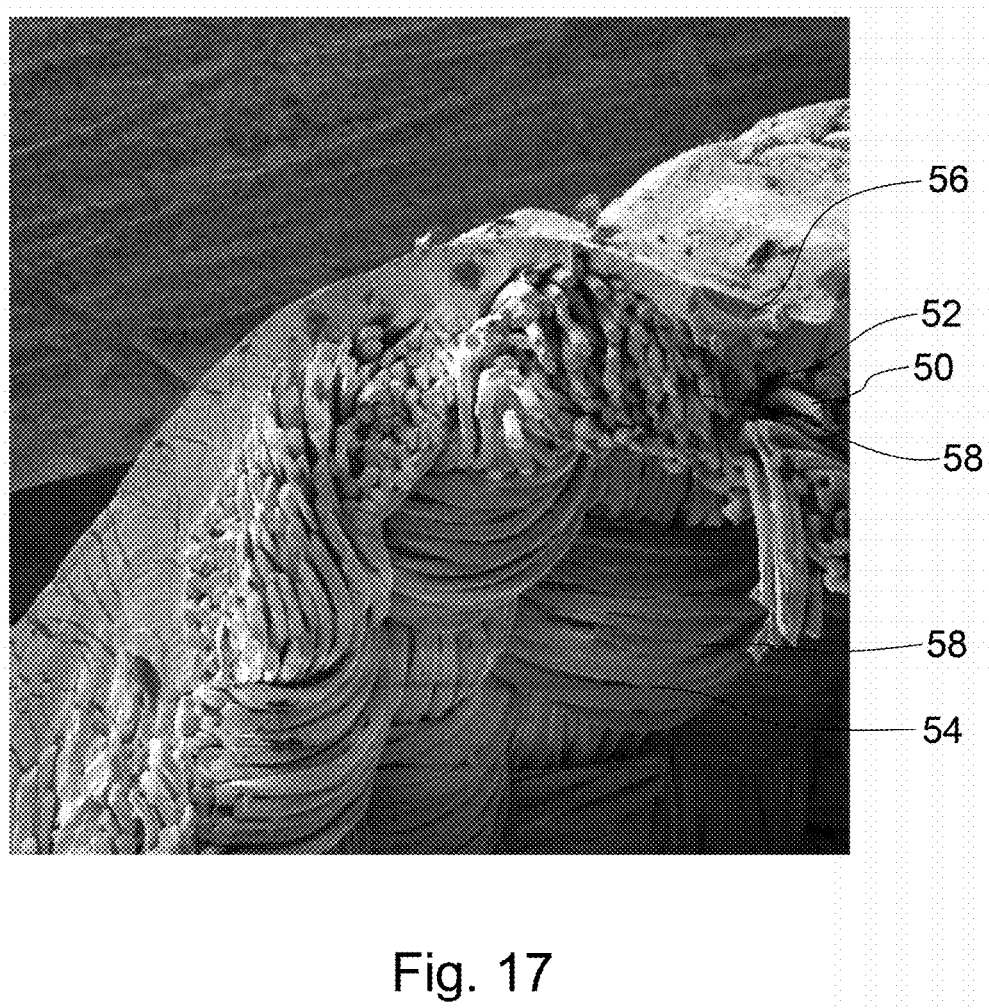
Figure 18:
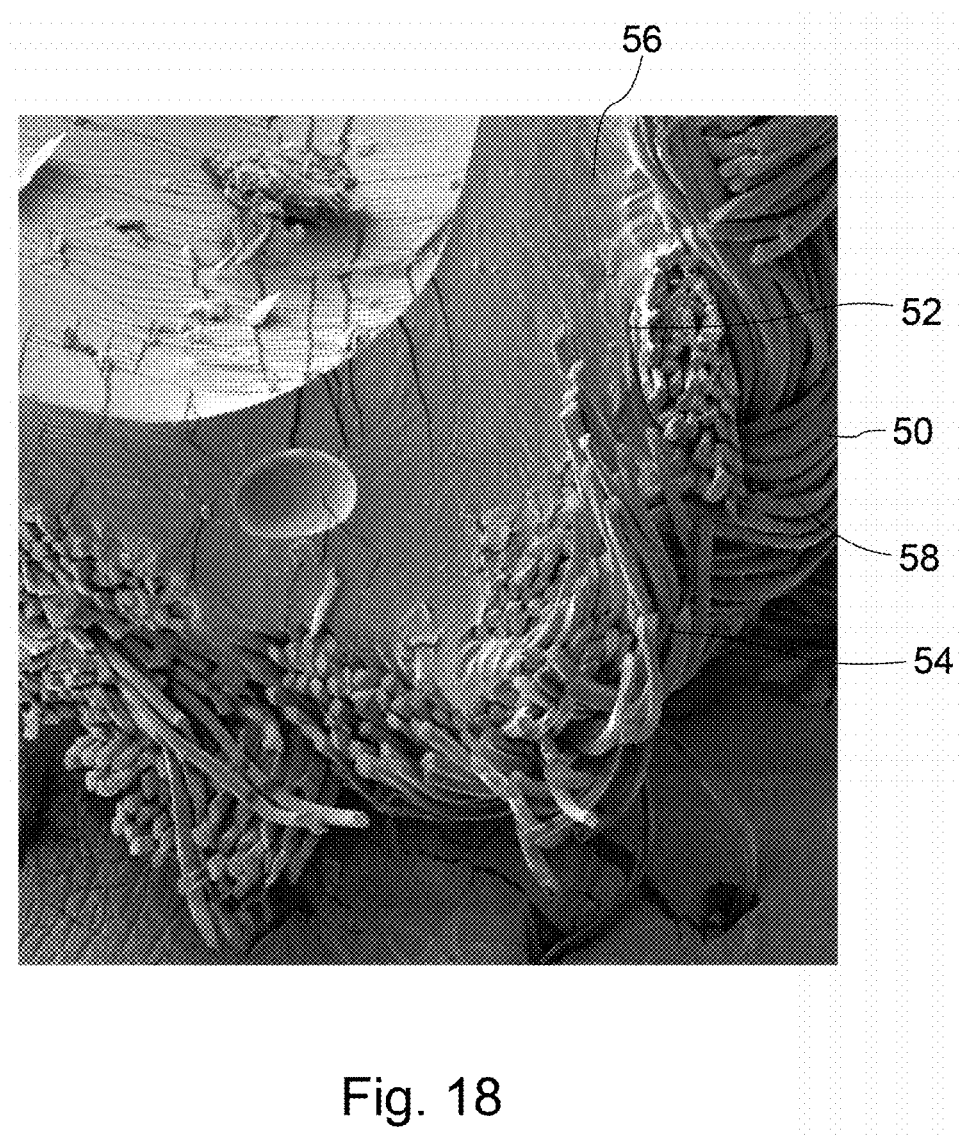

FIGS. 16-18 are SEM photographs of sample 7 from the above-described Tables. Sample 7 had the following characteristics:

Masking Solution: 15% PVP, 0% Glycerol in water;
Silicone Dispersant: 15% Silicone in heptane;
Silicone Coverage: 40 mg/cm$^2$;
Silicone Penetration Grading: 2 (Silicone is visible penetrating to the inside surface);
Silicone Adherence Grading: 0 (Silicone is well adhered to graft and showing no signs of failure);
Measured Leakage at 120 mmHg: 4 ml/min;
Measured Leakage at 600 mmHg: 14 ml/min;
Handling Assessment: 2 (Graft judged comparable to Reference Sample 64B); and
Tensile Force to Extend Graft by 20%: 0.541 N.

FIG. 16 shows an SEM photograph of a cross-section of the textile 50 of Sample 7. As shown in FIG. 16, the textile fiber bundles 58 on the outer textile surface 52 were penetrated and encapsulated with silicone sealant 56. The textile fiber bundles 58 at the inner textile surface 54 were free from silicone sealant 60 penetration. As shown in FIGS. 17 and 18, the silicone sealant 56 penetrated and encapsulated the textile fiber bundles 58 at the outer textile surface. The fiber bundles 58 at the inner textile surface 54 were free from silicone sealant 56.

Figure 19:
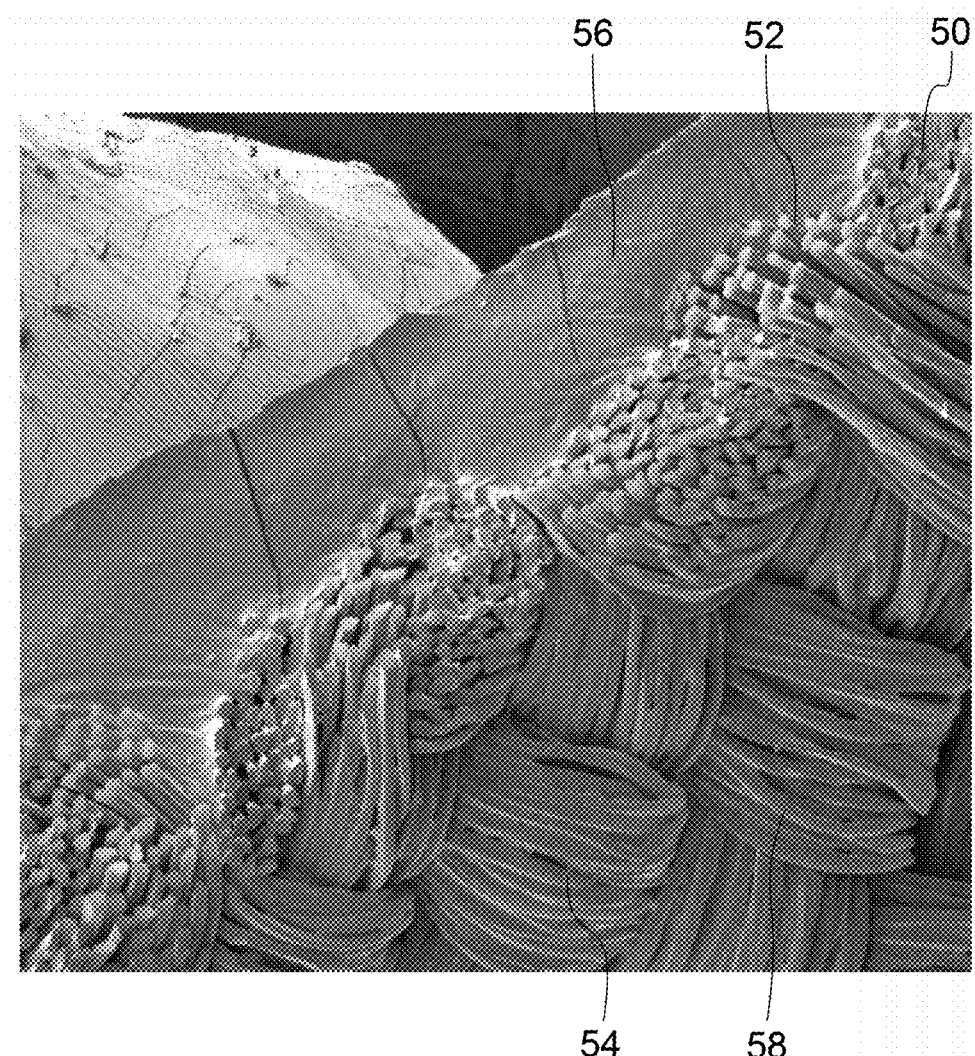
FIG. 19 is a SEM photograph of a cross-sectional section of textile sample 15, which is described below in conjunction with Tables 10-14.

FIG. 19 is an SEM photograph of sample 15 from the above-described Tables. Sample 15 had the following characteristics:

Masking Solution: 15% PVP, 5% Glycerol in water;
Silicone Dispersant: 15% Silicone in heptane;
Silicone Coverage: 40 mg/cm$^2$;
Silicone Penetration Grading: 2 (Silicone is visible penetrating to the inside surface);
Silicone Adherence Grading: 1 (Graft reached the maximum pressure, but the leak rate has visibly increased);
Measured Leakage at 120 mmHg: 3 ml/min;
Measured Leakage at 600 mmHg: 22 ml/min;
Handling Assessment: 2 (Graft judged comparable to Reference Sample 64B); and
Tensile Force to Extend Graft by 20%: 0.719 N.

FIG. 19 is a SEM photograph of a cross-section of the textile 50 of Sample 15. The silicone sealant 56 encapsulated the outer fibers of the fiber bundles 58 at the outer textile surface 2. The fiber bundles 58 at the inner textile 54 were free from penetration of the silicone sealant 56. Dyed silicone sealant (not shown) was visible ay the inner surface 54.

Glycerol Hydration of Masking Agents

The use of glycerol within different masking agent formulations has been demonstrated on multiple formulations with the aim of hydrating or plasticizing the (PVP) masking agent and improving its ability to cover and fill the yarn structure and prevent the sealant dispersion from ingress to the inner surface.

Masking Agent Sample Preparation

Masking agents were prepared using following method:

A target weight of PVP (MW 10,000) was introduced in a plastic beaker on a scale balance. A 100 ml masking agent solution was prepared at a target mass of 10 g PVP (10% concentration). The target volume of de-ionised water was introduced into a 100 ml plastic measuring cylinder. A target volume of 90 ml was required. The de-ionised water was added into the PVP in plastic beaker. A magnetic stirrer rod was placed in the water, and the beaker was placed on the magnetic stirrer. The magnetic stirrer was turned on at a speed of 350-450 RPM, the stirrer was centered in the beaker. The stirring was done at room temperature. Stirring continued until there was no visible PVP solute, but for at least 2 minutes. After stirring the masking agent solution, it can be removed from stirrer and used for control sample preparation.

Additional steps were used for subsequent samples with added glycerol. The plastic beaker was returned to scale balance, tared, and the required quantity of glycerol was added to the masking agent solution. The target glycerol content was calculated as a percentage by mass of the PVP. The target weight of Glycerol added at each stage was 1 g, corresponding to cumulative weights of 1, 2, 3, 4, 5, 6, 7, 8, 9 and 10 g. Each beaker was stirred for at least 2 minutes after each added quantity of Glycerol.

A summary of the samples prepared are shown below.

TABLE 15

| Sample Ref. | Volume of water | PVP Weight | PVP % w/v | Glycerol Weight | Glycerol as % of PVP |
|---|---|---|---|---|---|
| Control | 90 ml | 10 g | 10% | 0 | 0 |
| A) 10% Glycerol | 90 ml | 10 g | 9.9% | 1 g | 10% |
| B) 20% Glycerol | 90 ml | 10 g | 9.8% | 2 g | 20% |
| C) 30% Glycerol | 90 ml | 10 g | 9.7% | 3 g | 30% |
| D) 40% Glycerol | 90 ml | 10 g | 9.6% | 4 g | 40% |
| E) 50% Glycerol | 90 ml | 10 g | 9.5% | 5 g | 50% |
| F) 60% Glycerol | 90 ml | 10 g | 9.4% | 6 g | 60% |
| G) 70% Glycerol | 90 ml | 10 g | 9.3% | 7 g | 70% |
| H) 80% Glycerol | 90 ml | 10 g | 9.3% | 8 g | 80% |
| I) 90% Glycerol | 90 ml | 10 g | 9.2% | 9 g | 90% |
| J) 100% Glycerol | 90 ml | 10 g | 9% | 10 g | 100% |

Dispersion Drop Castings

Three individual drops of each masking agent formulation were cast onto a dark coloured sheet to allow visual observation during the drying process. The drying was accelerated by using a desk fan at room temperature Assessments of the masking agents after drying were as follows:

TABLE 16

| Sample Ref. | Assessment after 12 hours | Assessment after 96 hours |
|---|---|---|
| Control | Looked white, Dry to touch | Dry, Brittle |
| A) 10% Glycerol | Looked hydrated, Dry to touch | Looked hydrated, Dry to touch |
| B) 20% Glycerol | Hydrated, Soft, Tacky to touch | Hydrated, Soft, Tacky to touch |
| C) 30% Glycerol | Very Sticky to touch | Sticky to touch |
| D) 40% Glycerol | Sticky, still wet | Sticky, still wet |
| E) 50% Glycerol | Wet to touch | Wet to touch |
| F) 60% Glycerol | Wet to touch | Wet to touch |
| G) 70% Glycerol | Wet to touch | Wet to touch |
| H) 80% Glycerol | Wet to touch | Wet to touch |

TABLE 16-continued

| Sample Ref. | Assessment after 12 hours | Assessment after 96 hours |
|---|---|---|
| I) 90% Glycerol | Wet to touch | Wet to touch |
| J) 100% Glycerol | Wet to touch | Wet to touch |

Conclusions

The control masking agent formulation (e.g., PVP-only) dried out fully within a few hours and became brittle. Use of this PVP-only masking agent may result in a stiff graft structure once mask is applied and dried. The use of 10% glycerol helped to hydrate the PVP masking agent solution, and appeared dry after 12 hours. A masking agent solution consisting of 20% glycerol retains some hydration at 12 hours and is soft/deformable to touch. A range of between about 1% and about 30% glycerol to PVP, by weight, provides appropriate ranges for use with the present invention.

Moreover, the present invention is not limited to vascular prostheses in conduit-type shapes. The methods, coatings, and masking agents of the present invention may suitably be used with other textile products, including medical and non-medical (e.g., non-implantable) textile products. Other medical products may include ventricular assist devices, artificial heart conduits, medical sheets, patches, meshes, and the like. Non-medical textiles may include, but are not limited to, clothing, geotextiles, transportation textiles, military and/or defense textiles, safety and/or protective textiles, sports and/or recreation textiles, and the like. Further, textile products are not limited to tubular conduits, but may be of any shape including, but not limited to for example, sheets and/or tapes (e.g., two-dimensional products), or even three-dimensional shaped products other than conduit-shaped products.

Useful polymeric materials and/or for fibers for non-medical or non-implantable textiles may include, but are not limited to, polyethylene terephthalate (PET), polytetrafluoroethylene (PTFE), expanded polytetrafluoroethylene (ePFTE), polyolefins, polyesters, poly(ether amides), poly(ether esters), poly(ether urethanes), poly(ester urethanes), poly(ethylene-styrene/butylene-styrenes), and other block copolymers. Useful animal fibers for the non-medical or non-implantable textiles of the present invention may include, but are not limited to, wool, alpaca, angora, mohair, llama, cashmere, and silk. Useful natural fibers may include, but are not limited to, linen, cotton bamboo, hemp, corn, nettle, soy fiber, and the like.

The masking agents and/or the sealants may be applied by brushing, spray-coating, dipping or immersing, and the like. The present invention, however is not limited to such techniques, and other techniques, such as chemical deposition, vapor deposition, chemical vapor deposition, physical vapor deposition, printing and the like, may suitably be used. These techniques are generally suitable for medical textiles. However, for large commercial scale textile production, including non-medical textiles, other techniques may also be used. For example, coating and/or masking materials for textile sheets or substrates may be applied by squeegee type coating, roller coating, knife coating, nip coating, dip coating, cast coating, chemical deposition, vapor deposition, and the like. Moreover, printing techniques, such as roller printing, stencil printing, screen printing, inkjet printing, lithographic printing, 3D printing, and the like may be used with the present invention for applying the masking agents and/or the sealing agents. Furthermore, mechanical devices may be employed to control the depth of penetration of the masking agent and/or sealing agent into the wall of the textile substrate of graft. For example, with a tubular graft an expandable balloon may be to control the depth of penetration of the masking agent into the graft wall.

Modifications may be made to the foregoing embodiments within the scope of the present invention.

The following embodiments or aspects of the invention may be combined in any fashion and combination and be within the scope of the present invention, as follows:

Embodiment 1. A method of manufacturing a tubular graft comprising the steps of:

providing a textile comprising a tubular wall disposed between a first open end and an opposed second open end, an inner surface and an opposed outer surface defining an interior wall portion therein between, the tubular wall comprising a textile construction of one or more filaments or yarns, the textile construction by itself being permeable to liquid;

applying a substantially water-soluble material to at least a portion of the tubular wall; and applying a substantially water-insoluble sealant to at least a part of the outer surface of the tubular wall, the substantially water-insoluble sealant being configured to mitigate movement of fluid through the wall of the conduit;

wherein the water-soluble material is configured to mitigate penetration of the sealant to the inner surface of the conduit.

Embodiment 2. The method of embodiment 1, wherein the step of applying the water-soluble material to at least a portion of the tubular wall comprises applying the water-soluble material to at least a portion of the inner surface and a portion of the interior portion of the tubular wall.

Embodiment 3. The method of embodiment 1 or 2, wherein the step of applying the water-soluble material to at least a portion of the tubular wall comprises applying the water-soluble material to at least a portion of the outer surface of the tubular wall.

Embodiment 4. The method of any preceding embodiment, wherein the water-soluble material is a solution of the water-soluble material and a solvent.

Embodiment 5. The method of any preceding embodiment, wherein the solvent is selected form the group consisting of water, lower alcohols, and combinations thereof.

Embodiment 6. The method of any preceding embodiment, wherein the solvent is at least partially removed prior to applying the substantially water-insoluble sealant.

Embodiment 7. The method of any preceding embodiment, further comprising removal of at least a portion of the water-soluble material is by dissolution, abrading, peeling, degrading, and combinations thereof.

Embodiment 8. The method of any preceding embodiment, wherein the water-soluble material is selected from the group consisting of polyvinylpyrrolidone, glycerol, methyl cellulose, poly(ethylene glycol), poly(ethylene glycol) hydrogel, polyethylene oxide, and combinations thereof.

Embodiment 9. The method of any preceding embodiment, wherein the substantially water-insoluble sealant is an elastomeric material selected from the group consisting of moisture curing, light curing, thermo-curing, platinum catalyzed, anaerobic curing materials or a combination of these curing mechanisms.

Embodiment 10. The method of embodiment 9, wherein the elastomeric material is selected from the group consisting of silicones, polyurethanes, polycarbonates, thermoplastic elastomers, and combinations thereof.

Embodiment 11. The method of any preceding embodiment, wherein one of more of the substantially water-soluble coating or the substantially water-insoluble coating further comprises a component selected from the group consisting of a colorant, a therapeutic agent, a dye, and a fluorescent indicator.

Embodiment 12. The method of any preceding embodiment, wherein the water-soluble material comprises polyvinylpyrrolidone having a molecular weight of between approximately 6,000 g/mol and approximately 15,000 g/mol.

Embodiment 13. The method of any preceding embodiment, wherein applying the water-soluble material forms layer on substantially all of the inner surface of the tubular wall.

Embodiment 14. The method of any preceding embodiment, further comprising curing the substantially water-insoluble sealant.

Embodiment 15. The method of any preceding embodiment, further comprising curing the substantially water-insoluble sealant; and thereafter removing at least a portion of the water-soluble material.

Embodiment 16. The method of embodiment 14, further comprising removing substantially all of the water-soluble material from the inner surface of the tubular wall.

Embodiment 17. The method of any preceding embodiment, further comprising:
removing at least a part of the water-soluble material from at least a part of the outer surface of the tubular wall prior to the applying the substantially water-insoluble sealant.

Embodiment 18. The method of any one of embodiments 15 to 17, wherein the removing at least the portion of the water-soluble material is carried out at a temperature of between approximately 15° C. and approximately 140° C.

Embodiment 19. The method of any one of embodiments 15 to 18, wherein the removing at least the portion of the water-soluble material further comprises the step of applying a solvent thereto.

Embodiment 20. The method of embodiment 19, wherein the solvent comprises water, lower alcohols, and combinations thereof.

Embodiment 21. The method of any one of embodiments 15 to 20, wherein the tubular textile is agitated, rotated, spun, and shaken, or the like, during the removal of the water-soluble material.

Embodiment 22. The method of any one of embodiments 15 to 21, wherein the removal of the water-soluble material comprises dissolving, etching, plasma etching, ablating, abrading and combinations thereof of the water-soluble material.

Embodiment 23. The method of any preceding embodiment, wherein the step of applying the water-soluble material further comprises spraying the water-soluble material, brushing the water-soluble material, immersing at least a portion of the tubular wall into a solution of the water-soluble material, and combinations thereof.

Embodiment 24. The method of any preceding embodiment, wherein the substantially water-insoluble sealant is a polymer solution.

Embodiment 25. The method of embodiment 24, wherein the polymer solution comprises an organic solvent.

Embodiment 26. The method of embodiment 25, wherein the organic solvent comprises at least one of heptane and xylene.

Embodiment 27. The method of any preceding embodiment, wherein the substantially water-insoluble sealant is applied by brushing, spraying, roller coating the substantially water-insoluble sealant thereon.

Embodiment 28. The method of any preceding embodiment, wherein the method comprises one or more steps of selectively applying the substantially water-insoluble sealant to one or more portions of the tubular wall, such that the tubular wall comprises at least two sections having substantially different amounts of the substantially water-insoluble sealant thereon.

Embodiment 29. The method of any one of embodiments 14 to 28, wherein the tubular wall having the coating of the substantially water-insoluble sealant is, after curing thereof, substantially impermeable to liquid.

Embodiment 30. The method of any preceding embodiment, wherein, after curing of the substantially water-insoluble sealant, the tubular wall has a water permeability of about 0.16 ml/min/cm² at 120 mm Hg pressure or less than 0.16 ml/min/cm² at 120 mm Hg pressure.

Embodiment 31. A textile comprising:
a tubular wall disposed between a first open end and an opposed second open end and having an inner surface and an opposed outer surface, the tubular wall comprising a textile construction of one or more filaments or yarns, the textile construction by itself being permeable to liquid;
wherein a portion of the inner surface comprises a coating of a substantially water-soluble material thereon;
wherein the outer surface further comprises a coating of a substantially water-insoluble sealant disposed thereon; and
wherein the tubular wall having the coating of the substantially water-insoluble sealant is, after curing thereof, substantially impermeable to liquid.

Embodiment 32. The textile of embodiment 31, wherein the water-soluble material is selected from the group consisting of polyvinylpyrrolidone, glycerol, methyl cellulose, poly(ethylene glycol) poly(ethylene glycol) hydrogel, polyethylene oxide, and combinations thereof.

Embodiment 33. The textile of embodiment 31 or 32, wherein the coating of the water-soluble material comprises an oleophobic layer.

Embodiment 34. The textile of any one of embodiments 31 to 33, wherein the water-soluble material comprises polyvinylpyrrolidone having a molecular weight of between approximately 6,000 g/mol and approximately 15,000 g/mol.

Embodiment 35. The textile of any one of embodiments 31 to 34, the water-soluble material comprises polyvinylpyrrolidone and glycerol.

Embodiment 36. The textile of any one of embodiments 31 to 35, wherein the substantially water-insoluble sealant is an elastomeric material selected from the group consisting of moisture curing, light curing, thermo-curing, platinum catalyzed, anaerobic curing materials or a combination of these curing mechanisms.

Embodiment 37. The textile of embodiment 36, wherein the elastomeric material is selected from the group consisting of silicones, polyurethanes, polycarbonates, thermoplastic elastomers, and combinations thereof.

Embodiment 38. The textile of any one of embodiments 31 to 37, wherein one of more of the substantially water-soluble coating or the substantially water-insoluble coating comprises a component selected from the group consisting of a colorant, a therapeutic agent, a dye, and a fluorescent indicator.

Embodiment 39. The textile of any one of embodiments 31 to 38, wherein, after curing of the substantially water-insoluble sealant, the tubular wall has a water permeability of about 0.16 ml/min/cm$^2$ at 120 mm Hg pressure or less than 0.16 ml/min/cm$^2$ at 120 mm Hg pressure.

Embodiment 40. The textile of any one of embodiments 31 to 39, wherein the textile construction is selected from the group consisting of a weave of the one or more filaments or yarns, a knit of the one or more filaments or yarns, a braid of the one or more filaments or yarns, and a web of the one or more filaments or yarns.

Embodiment 41. The textile of any one of embodiments 31 to 40, wherein the tubular wall is a crimped wall having a series of peaks and valleys.

Embodiment 42. The textile of embodiment 41, wherein the substantially water-insoluble sealant is disposed at about 8 mg/cm$^2$ of area of the tubular wall or greater than 8 mg/cm$^2$ of area of the tubular wall.

Embodiment 43. The textile of any one of embodiments 31 to 40, wherein the tubular wall is a non-crimped wall being substantially free of peaks and valleys.

Embodiment 44. The textile of embodiment 43, wherein the substantially water-insoluble sealant is disposed at about 4 mg/cm$^2$ of area of the tubular wall or greater than 4 mg/cm$^2$ of area of the tubular wall.

Embodiment 45. The textile of any one of embodiments 31 to 44, wherein the substantially water-insoluble sealant is disposed at about 14 mg/cm$^2$ of area of the tubular wall or less than 14 mg/cm$^2$ of area of the tubular wall.

Embodiment 46. The textile of any one of embodiments 31 to 45,
wherein one portion of the tubular wall has a first level of the substantially water-insoluble sealant to provide a first soft, flexible zone;
wherein another portion of the tubular wall has a second level of the substantially water-insoluble sealant to provide a second zone having a stiffness greater than the first zone; and
wherein the second level the substantially water-insoluble sealant is greater than the first level of the substantially water-insoluble sealant.

Embodiment 47. The textile of any one of embodiments 31 to 46, wherein at least a portion of the coating of the substantially water-insoluble sealant engages at least a portion of the one or more filaments or yarns.

Embodiment 48. The textile of any one of embodiments 31 to 47, where in the textile is an implantable medical device.

Embodiment 49. The textile of embodiment 48, wherein the implantable medical device is selected from the group consisting of surgical vascular grafts, and endovascular graphs, meshes, patches, hernia plugs, vascular wraps, heart valves, filters, and the like.

Embodiment 50. The textile of any one of embodiments 31 to 49, wherein the textile is a delivery medical device.

Embodiment 51. The textile of embodiment 50, wherein the delivery medical device is a catheter.

Embodiment 52. A textile structure comprising:
a fluid permeable polymeric textile layer having opposing first and second surfaces and a length;
a cross-linkable water-insoluble elastomeric layer on the first textile surface configured to render the liquid permeable polymeric textile layer substantially impermeable to fluid when cured; and
a substantially dried water-soluble polymer layer on the second textile surface;
wherein water-soluble polymer layer substantially inhibits migration of the water-insoluble elastomeric layer onto the second surface; and
wherein the water-soluble polymer layer is substantially removable by exposure to water.

Embodiment 53. The textile structure of embodiment 52, wherein the weight ratio of the cross-linkable water-insoluble elastomeric polymer to the water-soluble polymer is from about 0.1:1 to about 100:1.

Embodiment 54. The textile structure of embodiment 53, wherein the weight ratio of the cross-linkable water-insoluble elastomeric polymer to the water-soluble polymer is from about 1:1 to about 20:1.

Embodiment 55. A textile structure comprising:
a fluid permeable polymeric textile layer having opposing first and second surfaces and a length;
a crosslinked water-insoluble elastomeric polymer layer on the first textile surface forming a substantially fluid impermeable barrier, wherein the crosslinked water-insoluble elastomeric layer is adhered to the first textile surface by elastomeric shrinkage; and
a water dissolvable polymer layer dried on the second textile surface;
wherein the weight ratio of the crosslinked water-insoluble elastomeric polymer to the water dissolvable polymer is from about 0.1:1 to about 100:1.

Embodiment 56. The textile construction of embodiment 55, wherein the weight ratio of the crosslinked water-insoluble elastomeric polymer to the water dissolvable polymer is from about 1:1 to about 20:1.

Embodiment 57. A graft comprising:
a tubular wall disposed between a first open end and an opposed second open end and having an inner surface and an opposed outer surface, the tubular wall comprising a textile construction of one or more filaments or yarns;
wherein the outer surface comprises a coating of a substantially water-insoluble sealant disposed thereon;
wherein the inner surface is substantially free of the substantially water-insoluble sealant; and
wherein the tubular wall has a water permeability of about 0.16 ml/min/cm$^2$ at 120 mm Hg pressure or less than 0.16 ml/min/cm$^2$ at 120 mm Hg pressure.

Embodiment 58. The graft of embodiment 57, wherein the textile construction is selected from the group consisting of a weave of the one or more filaments or yarns, a knit of the one or more filaments or yarns, a braid of the one or more filaments or yarns, and a web of the one or more filaments or yarns.

Embodiment 59. The graft of embodiment 57 or 58, wherein the coating is disposed within an intermediate portion of the tubular wall between the inner surface and the opposed outer surface.

Embodiment 60. The graft of any one of embodiments 57 to 59, wherein the tubular wall is a crimped wall having a series of peaks and valleys.

Embodiment 61. The graft of any one of embodiments 57 to 60, wherein the substantially water-insoluble sealant is disposed at about 8 mg/cm$^2$ of area of the tubular wall or greater than 8 mg/cm$^2$ of area of the tubular wall.

Embodiment 62. The graft of any one of embodiments 57 to 59, wherein the tubular wall is a non-crimped wall being substantially free of peaks and valleys.

Embodiment 63. The graft of any one of embodiments 57 to 62, wherein the substantially water-insoluble sealant is disposed at about 4 mg/cm$^2$ of area of the tubular wall or greater than 4 mg/cm$^2$ of area of the tubular wall.

Embodiment 64. The graft of any one of embodiments 57 to 63, wherein the substantially water-insoluble sealant is disposed at about 14 mg/cm$^2$ of area of the tubular wall or less than 14 mg/cm$^2$ of area of the tubular wall.

Embodiment 65. The graft of any one of embodiments 57 to 64, wherein the substantially water-insoluble sealant is an elastomeric material selected from the group consisting of moisture curing, light curing, thermo-curing, platinum catalyzed, anaerobic curing materials or a combination of these curing mechanisms.

Embodiment 66. The graft of embodiment 65, wherein the elastomeric material is selected from the group consisting of silicones, polyurethanes, polycarbonates, thermoplastic elastomers, and combinations thereof.

Embodiment 67. The graft of any one of embodiments 57 to 66, wherein one of more of the substantially water-soluble coating or the substantially water-insoluble coating comprises a component selected from the group consisting of a colorant, a therapeutic agent, a dye, and a fluorescent indicator.

Embodiment 68. The graft of any one of embodiments 57 to 67, wherein the substantially water-insoluble sealant is selected from the group consisting of silicone, room temperature vulcanizing silicone, thermoplastic polyurethane, aliphatic polycarbonate, one or more thermoplastic elastomers, polycarbonate, and combinations thereof.

Embodiment 69. The graft of any one of embodiments 57 to 69,
wherein one portion of the tubular wall has a first level of the substantially water-insoluble sealant to provide a first soft, flexible zone;
wherein another portion of the tubular wall has a second level of the substantially water-insoluble sealant to provide a second zone having a stiffness greater than the first zone; and
wherein the second level the substantially water-insoluble sealant is greater than the first level of the substantially water-insoluble sealant.

Embodiment 70. An implantable or deliverable medical textile comprising:
a wall having a textile construction and having a first surface and an opposed second surface;
wherein the second surface comprises a coating of a substantially water-insoluble sealant disposed thereon;
wherein the first surface is substantially free of the substantially water-insoluble sealant; and
wherein the wall has a water permeability of about 0.16 ml/min/cm$^2$ at 120 mm Hg pressure or less than 0.16 ml/min/cm$^2$ at 120 mm Hg pressure.

Embodiment 71. An assembly for producing an implantable or deliverable medical textile having a selectively applied water-insoluble sealant layer, comprising:
a mandrel having a length, a hollow lumen disposed within a portion of the length, at least one open end, and a plurality of perforations through a wall of the mandrel;
a reservoir in fluid communication with the open lumen of the mandrel; and
a water-soluble polymer disposed within the reservoir.

Embodiment 72. The assembly of embodiment 71, further comprising a tubular graft securably disposed over a portion of the mandrel having the plurality of perforations.

Embodiment 73. The assembly of embodiment 71 or 72, further comprising a vacuum source in fluid communication with the hollow lumen of the mandrel.

Embodiment 74. The assembly of embodiment 73, further comprising a manifold configured to provide selective fluid communication between the hollow lumen of the mandrel and the reservoir and/or the vacuum source.

Embodiment 75. The assembly of any one of embodiments 71 to 74, further comprising a source of pressurized and/or blown air.

Embodiment 76. The assembly of embodiment 75, wherein the pressurized and/or blown air is in fluid communication with the hollow lumen of the mandrel.

Embodiment 77. The method, textile, graft, device or assembly of any preceding embodiment, further including a support member.

Embodiment 78. The method of any one of embodiments 1 to 30, wherein the support member is added to the outer surface of the wall of the conduit.

Embodiment 79. The method of embodiment 78, wherein the support member is wrapped around the outer surface of the wall of the conduit.

Embodiment 80. The method of embodiment 79, wherein the conduit comprises a plurality of crimps, and the support member is arranged to nest between the plurality of crimps.

Embodiment 81. The method of any one of embodiments 78 to 80, wherein a step of adding the support member to the conduit is carried out prior to the step of adding the sealant to the conduit.

Embodiment 82. The method of any one of embodiments 78 to 81, wherein a step of adding the sealant to the conduit is used, at least in part, to attach the support member to the conduit.

Embodiment 83. The method of any one of embodiments 78 to 82, wherein the support member is a flexible, polymer member.

Embodiment 84. The method of any one of embodiments 78 to 83, wherein the flexible support member is present on a portion of the length of the graft.

Embodiment 85. A method of manufacturing a vascular prosthesis, the method comprising the steps of:
(i) providing a conduit comprising a wall, the wall of the conduit comprising an inner surface and an outer surface, at least a section of the conduit being porous;
(ii) adding a masking agent to at least a part of the porous section of the conduit; and
(iii) adding a sealant to at least a part of the porous section of the conduit, the sealant being configured to mitigate movement of fluid through the wall of the conduit;
wherein the masking agent is configured to mitigate presence of the sealant on the inner surface of the conduit.

Embodiment 86. The method of embodiment 85, wherein the sealant forms a sealing layer on at least a part of the outer surface of the wall of the conduit.

Embodiment 87. The method of embodiment 85 or embodiment 86, wherein the sealant forms a sealing layer on substantially all of the outer surface of the wall of the conduit.

Embodiment 88. The method of any preceding embodiments 85 to 87, wherein the masking agent forms a masking agent layer on at least a part of the inner surface of the wall of the conduit.

Embodiment 89. The method of any preceding embodiments 85 to 88, wherein the masking agent forms a masking agent layer on substantially all of the inner surface of the wall of the conduit.

Embodiment 90. The method of any preceding embodiments 85 to 89, wherein substantially all of the conduit is porous.

Embodiment 91. The method of any preceding embodiments 85 to 90, wherein the method comprises one or more masking agent removal steps, the, or each, masking agent removal step comprising the step of removing at least a part of the masking agent from the conduit.

Embodiment 92. The method of embodiment 91, wherein the method comprises the step of removing at least a part of the masking agent from at least a part of the outer surface of the wall of the conduit prior to the step of adding the sealant to the porous section of the conduit.

Embodiment 93. The method of embodiment 91 or embodiment 92, wherein the method comprises the step of removing at least a part of the masking agent from the inner surface of the wall of the conduit subsequent to the step of adding the sealant to at least a part of the porous section of the conduit.

Embodiment 94. The method of any one of embodiments 91 to 93, wherein the method comprises the step of removing substantially all of the masking agent from the conduit subsequent to the step of adding the sealant to at least a part of the porous section of the conduit.

Embodiment 95. The method of any one of embodiments 91 to 94, wherein at least one of the masking agent removal steps is carried out at a temperature of between approximately 15° C. and approximately 140° C.

Embodiment 96. The method of any one of embodiments 91 to 95, wherein at least one of the masking agent removal steps comprises the step of removing at least a part of the masking agent by applying a solvent thereto.

Embodiment 97. The method of embodiment 96, wherein the solvent comprises water.

Embodiment 98. The method of any one of embodiments 91 to 97, wherein the conduit is at least one of: agitated, rotated, spun, and shaken, or the like, during at least one of the masking agent removal steps.

Embodiment 99. The method of any one of embodiments 91 to 98, wherein at least one of the masking agent removal steps is carried out by etching, plasma etching, ablating and/or abrading the masking agent.

Embodiment 100. The method of any preceding embodiments 85 to 99, wherein the inner surface of the wall of the conduit is configured to promote the growth of biological tissue thereon.

Embodiment 101. The method of any preceding embodiments 85 to 100, wherein the masking agent comprises a polymer.

Embodiment 102. The method of embodiment 101, wherein the masking agent comprises a water-soluble polymer.

Embodiment 103. The method of embodiment 101 or embodiment 102, wherein the masking agent comprises at least one of: polyvinylpyrrolidone, glycerol, methyl cellulose, poly(ethylene glycol), and poly(ethylene glycol) hydrogel.

Embodiment 104. The method of any preceding embodiments 85 to 103, wherein the masking agent is biocompatible.

Embodiment 105. The method of any preceding embodiments 85 to 104, wherein the masking agent forms a biocompatible masking agent layer when added to the conduit.

Embodiment 106. The method of any preceding embodiments 85 to 105, wherein the masking agent is added to at least a part of the porous section of the conduit from a masking agent solution.

Embodiment 107. The method of embodiment 106, wherein the masking agent solution is a polymer solution.

Embodiment 108. The method of embodiment 106 or embodiment 107, wherein the step of adding the masking agent to at least a part of the porous section of the conduit is performed by spraying the masking agent solution onto at least a part of the porous section of the conduit.

Embodiment 109. The method of embodiment 108, wherein the masking agent solution is added to the conduit by spraying the masking agent onto at least a part of the inner surface of the wall of the conduit.

Embodiment 110. The method of any one of embodiments 106 to embodiment 109, wherein the step of adding the masking agent to at least a part of the porous section of the conduit is performed by immersing at least a part of the porous section of the conduit in the masking agent solution.

Embodiment 111. The method of embodiment 110, wherein substantially all of the conduit is immersed in the masking agent solution.

Embodiment 112. The method of any one of embodiments 106 to 111, wherein the masking agent solution comprises between approximately 5% weight/volume (w/v) of polymer in solution and approximately 30% w/v of polymer in solution.

Embodiment 113. The method of any preceding embodiments 85 to 112, wherein the step of adding the sealant to at least a part of the porous section of the conduit does not result in the removal of the masking agent from the porous section of the conduit.

Embodiment 114. The method of any preceding embodiments 85 to 113, wherein the masking agent is configured to biodegrade when the vascular prosthesis is implanted inside the human or animal body.

Embodiment 115. The method of any preceding embodiments 85 to 114, wherein the conduit is a woven fibrous polymer conduit.

Embodiment 116. The method of any preceding embodiments 85 to 115, wherein the sealant comprises a polymer.

Embodiment 117. The method of embodiment 116, wherein the sealant is a water-insoluble polymer.

Embodiment 118. The method of any preceding embodiments 85 to 117, wherein the sealant forms a sealing layer when added to the conduit, the sealing layer being a polymer layer.

Embodiment 119. The method of any one of embodiments 116 to 118, wherein the sealant comprises at least one of: silicone, room temperature vulcanising silicone, thermoplastic polyurethane, aliphatic polycarbonate, one or more thermoplastic elastomers, and polycarbonate.

Embodiment 120. The method of any preceding embodiments 85 to 119, wherein the sealant is added to the conduit from a sealant solution.

Embodiment 121. The method of embodiment 120 wherein the sealant solution is a polymer solution.

Embodiment 122. The method of embodiment 120 or embodiment 121, wherein the sealant solution comprises an organic solvent.

Embodiment 123. The method of embodiment 122, wherein the sealant solution comprises at least one of heptane and xylene.

Embodiment 124. The method of any preceding embodiments 85 to 123, wherein the sealant is added to at least a part of the porous section of the conduit by brushing and/or spraying the sealant thereon.

Embodiment 125. The method of any preceding embodiments 85 to 124, wherein the sealant is configured to mitigate movement of blood through the wall of the conduit.

Embodiment 126. The method of any preceding embodiments 85 to 125, comprising the further step of sterilising the vascular prosthesis.

Embodiment 127. The method of embodiment 126, wherein the vascular prosthesis is sterilised by way of at least one of: a gamma sterilisation process, an electron beam sterilisation process, and an ethylene oxide sterilisation process.

Embodiment 128. The method of any preceding embodiments 85 to 127, wherein the conduit is moveable between a contracted state and an extended state.

Embodiment 129. The method of embodiment 128, wherein the step of adding the masking agent to at least a part of the porous section of the conduit is carried out, at least in part, while the conduit is in the contracted state, in the extended state, and/or when moved between the contracted state and the extended state.

Embodiment 130. The method of embodiment 128 or embodiment 129, wherein the step of adding the sealant to at least a part of the porous section of the conduit is carried out, at least in part, while the conduit is in the contracted state, in the extended state, and/or when moved between the contracted state and the extended state.

Embodiment 131. The method of any preceding embodiments 85 to 130, the method comprising one or more steps of weighing the conduit and/or measuring the length of the conduit, to determine, at least in part, the amount of masking agent, and/or or the amount of sealant, to add to at least a part of the porous section of the conduit.

Embodiment 132. The method of any preceding embodiments 85 to 131, wherein the step of adding the masking agent to at least a part of the porous section of the conduit comprises the step of providing gas to the conduit.

Embodiment 133. The method of embodiment 132, wherein the gas is directed towards the outer surface of the wall of the conduit.

Embodiment 134. The method of embodiment 132 or embodiment 133, wherein the gas is air.

Embodiment 135. The method of any preceding embodiments 85 to 134, wherein the method comprises the step of adding a support member to the conduit.

Embodiment 136. The method of embodiment 135, wherein the support member is added to the outer surface of the wall of the conduit.

Embodiment 137. The method of embodiment 136, wherein the support member is wrapped around the outer surface of the wall of the conduit.

Embodiment 138. The method of embodiment 137, wherein the conduit comprises a plurality of crimps, and the support member is arranged to nest between the plurality of crimps.

Embodiment 139. The method of any one of embodiments 135 to 138, wherein the step of adding the support member to the conduit is carried out prior to the step of adding the sealant to the conduit.

Embodiment 140. The method of any one of embodiments 135 to 139, wherein the step of adding the sealant to the conduit is used, at least in part, to attach the support member to the conduit.

Embodiment 141. The method of any one of embodiments 135 to 140, wherein the support member is a flexible, polymer member.

Embodiment 142. The method of any preceding embodiments 85 to 141, wherein the method comprises one or more steps of selectively adding sealant to one or more sections of the conduit, such that the conduit comprises at least two sections comprising substantially different amounts of sealant thereon.

Embodiment 143. A vascular prosthesis comprising:
a conduit comprising a wall, the wall of the conduit comprising an inner surface and an outer surface, at least a section of the conduit being porous;
wherein at least a part of the porous section comprises a sealant configured to mitigate movement of fluid through the wall of the conduit; and
wherein the inner surface of the wall of the conduit is substantially devoid of the sealant.

Embodiment 144. The vascular prosthesis of embodiment 143, wherein the sealant forms a sealing layer on at least a part of the outer surface of the wall of the conduit.

Embodiment 145. The vascular prosthesis of embodiment 143 or embodiment 144, wherein the sealant forms a sealing layer on substantially all of the outer surface of the wall of the conduit.

Embodiment 146. The vascular prosthesis of any one of embodiments 143 to 145, wherein substantially all of the conduit is porous.

Embodiment 147. The vascular prosthesis of any one of embodiments 143 to 146, wherein the inner surface of the wall of the conduit is configured to promote the ingrowth of biological tissue thereon.

Embodiment 148. The vascular prosthesis of any one of embodiments 143 to 147, wherein the conduit is a woven fibrous polymer conduit.

Embodiment 149. The vascular prosthesis of any one of embodiments 143 to 148, wherein the sealant forms a sealing layer, the sealing layer being a polymer layer.

Embodiment 150. The vascular prosthesis of any one of embodiments 143 to 149, wherein the sealant comprises at least one of: silicone, room temperature vulcanising silicone, thermoplastic polyurethane, aliphatic polycarbonate, one or more thermoplastic elastomers, and polycarbonate.

Embodiment 151. The vascular prosthesis of any one of embodiments 143 to 150, wherein the sealant is configured to mitigate movement of blood through the wall of the conduit.

Embodiment 152. The vascular prosthesis of any one of embodiments 143 to 151, wherein the vascular prosthesis is sterilised.

Embodiment 153. The vascular prosthesis of embodiment 152, wherein the vascular prosthesis is sterilised by way of at least one of the following: a gamma sterilisation process, an ethylene oxide sterilisation process, and an electron beam sterilisation process.

Embodiment 154. The vascular prosthesis of any one of embodiments 143 to 153, wherein the conduit is moveable between a contracted state and an extended state.

Embodiment 155. The vascular prosthesis of any one of embodiments 143 to 154, wherein the conduit comprises a support member.

Embodiment 156. The vascular prosthesis of embodiment 155, wherein the support member is located substantially adjacent to the outer surface of the wall of the conduit.

Embodiment 157. The vascular prosthesis of embodiment 156, wherein the support member is wrapped around the outer surface of the wall of the conduit.

Embodiment 158. The vascular prosthesis of embodiment 157, wherein the conduit comprises a plurality of crimps, the support member being arranged to nest between the plurality of crimps.

Embodiment 159. The vascular prosthesis of any one of embodiments 155 to 158, wherein the sealant is arranged to, at least in part, attach the support member to the conduit.

Embodiment 160. The vascular prosthesis of any one of embodiments 155 to 159, wherein the support member is a flexible, polymer member.

Embodiment 161. The vascular prosthesis of any one of embodiments 143 to 160, wherein the conduit is configured to have at least two sections having substantially different amounts of sealant thereon.

Embodiment 162. A kit of parts for manufacturing a vascular prosthesis, the kit of parts comprising:
(i) a conduit comprising a wall, the wall of the conduit comprising an inner surface and an outer surface, at least a section of the conduit being porous;
(ii) a masking agent; and
(iii) a sealant;
when applied to at least a part of the porous section of the conduit, the masking agent being configured to mitigate presence of the sealant on the inner surface of the conduit; and when applied to at least a part of the porous section of the conduit, the sealant being configured to mitigate movement of fluid through the wall of the conduit.

Embodiment 163. The kit of parts of embodiment 162, wherein addition of the sealant to at least a part of the porous section of the conduit forms a sealing layer on at least a part of the outer surface of the wall of the conduit.

Embodiment 164. The kit of parts of embodiment 162 or embodiment 163, wherein addition of the masking agent to at least a part of the porous section of the conduit forms a masking agent layer on at least part of the inner surface of the wall of the conduit.

Embodiment 165. The kit of parts of any one of embodiments 162 to 164, wherein substantially all of the conduit is porous.

Embodiment 166. The kit of parts of any one of embodiments 162 to 165, the kit of parts comprising a masking agent remover, the masking agent remover being operable to remove applied masking agent from the conduit.

Embodiment 167. The kit of parts of embodiment 166, wherein the masking agent remover comprises a solvent.

Embodiment 168. The kit of parts of embodiment 167, wherein the solvent comprises water.

Embodiment 169. The kit of parts of any one of embodiments 166 to 168, wherein the masking agent remover is operable to remove applied masking agent from the conduit at a temperature of between approximately 15° C. and approximately 140° C.

Embodiment 170. The kit of parts of any one of embodiments 162 to 169, the kit of parts comprising an abrading tool, the abrading tool being operable to remove applied masking agent from the conduit.

Embodiment 171. The kit of parts of any one of embodiments 162 to 170, wherein the inner surface of the wall of the conduit is configured to promote the ingrowth of biological tissue thereon.

Embodiment 172. The kit of parts of any one of embodiments 162 to 171, wherein the masking agent comprises a polymer.

Embodiment 173. The kit of parts of embodiment 172, wherein the masking agent comprises a water-soluble polymer.

Embodiment 174. The kit of parts of any one of embodiments 162 to 173, wherein masking agent applied to the conduit forms a masking agent layer, the masking agent layer being a polymer layer.

Embodiment 175. The kit of parts of any one of embodiments 172 to 174, wherein the masking agent comprises at least one of: polyvinylpyrrolidone, glycerol, methyl cellulose, and poly(ethylene glycol) hydrogel.

Embodiment 176. The kit of parts of any one of embodiments 162 to 175, wherein the masking agent is biocompatible.

Embodiment 177. The kit of parts of any one of embodiments 162 to 176, wherein masking agent applied to the conduit forms a biocompatible masking agent layer.

Embodiment 178. The kit of parts of any one of embodiments 162 to 177, wherein the kit of parts comprises a masking agent solution, the masking agent solution being operable to apply masking agent to the conduit.

Embodiment 179. The kit of parts of embodiment 178, wherein the masking agent solution is a polymer solution.

Embodiment 180. The kit of parts of embodiment 178 or embodiment 179, wherein the conduit is immersible in the masking agent solution.

Embodiment 181. The kit of parts of any one of embodiments 178 to 180, wherein the masking agent solution comprises between approximately 5% w/v of polymer in solution and approximately 30% w/v of polymer in solution.

Embodiment 182. The kit of parts of any one of embodiments 162 to 181, wherein when the masking agent and the sealant are applied to the conduit, the sealant is configured such that addition of the sealant to the conduit does not result in the removal of the applied masking agent from the conduit.

Embodiment 183. The kit of parts of any one of embodiments 162 to 182, wherein the masking agent is configured to biodegrade when implanted inside the human or animal body.

Embodiment 184. The kit of parts of any one of embodiments 162 to 183, wherein the conduit is a woven fibrous polymer conduit.

Embodiment 185. The kit of parts of any one of embodiments 162 to 184, wherein the sealant comprises a polymer, optionally a water-insoluble polymer.

Embodiment 186. The kit of parts of any one of embodiments 162 to 185, wherein the sealant, when applied to the conduit, forms a sealing layer, the sealing layer being a polymer layer.

Embodiment 187. The kit of parts of embodiment 185 or embodiment 186, wherein the sealant comprises at least one of: silicone, room temperature vulcanising silicone, thermoplastic polyurethane, aliphatic polycarbonate, one or more thermoplastic elastomers, and polycarbonate.

Embodiment 188. The kit of parts of any one of embodiments 162 to 187, wherein the kit of parts comprises a sealant solution operable to apply sealant to the conduit.

Embodiment 189. The kit of parts of embodiment 188, wherein the sealant solution is a polymer solution.

Embodiment 190. The kit of parts of embodiment 188 or embodiment 189, wherein the sealant solution comprises an organic solvent.

Embodiment 191. The kit of parts of embodiment 190, wherein the sealant solution comprises at least one of heptane and xylene.

Embodiment 192. The kit of parts of any one of embodiments 162 to 191, the kit of parts comprising a sealant applicator operable to apply sealant to the conduit, and/or a masking agent applicator operable to apply masking agent to the conduit.

Embodiment 193. The kit of parts of embodiment 192, wherein the sealant applicator is an apparatus for spray coating the sealant, and/or a brush, or the like.

Embodiment 194. The kit of parts of embodiment 192 or embodiment 193, wherein the masking agent applicator is a brush, an apparatus for spray-coating the masking agent, an apparatus for dipping or immersing the conduit in the masking agent, and/or an apparatus for wiping the masking agent onto the conduit.

Embodiment 195. The kit of parts of any one of embodiments 162 to 194, wherein the sealant, when applied to at least a part of the porous section of the conduit, is configured to mitigate movement of blood through the wall of the conduit.

Embodiment 196. The kit of parts of any one of embodiments 162 to 195, wherein the conduit is moveable between a contracted state and an extended state.

Embodiment 197. The kit of parts of any one of embodiments 162 to 196, the kit of parts comprising a further prosthesis.

Embodiment 198. The kit of parts of embodiment 197, wherein the further prosthesis is at least one of: a biological heart valve, a synthetic heart valve, a cardiac assist device, and a ventricular assist device, or the like.

Embodiment 199. The kit of parts of any one of embodiments 162 to 198, the kit of parts comprising a weighing device and/or a device for measuring the length of the conduit.

Embodiment 200. The kit of parts of any one of embodiments 162 to 199, the kit of parts comprising a gas flow apparatus operable to provide gas flow to the conduit.

Embodiment 201. The kit of parts of embodiment 200, wherein the gas is air.

Embodiment 202. A vascular system, the vascular system comprising:
a vascular prosthesis manufactured according to any one of embodiments 85 to 142; and
a further prosthesis;
wherein the vascular prosthesis is connected to the further prosthesis, such that fluid can flow between the vascular prosthesis and the further prosthesis.

Embodiment 203. The vascular system of embodiment 202, wherein the further prosthesis is at least one of: a biological heart valve, a synthetic heart valve, a cardiac assist device, and a ventricular assist device, or the like.

Embodiment 204. A method of implanting a vascular prosthesis, the method comprising the steps of:
providing a vascular prosthesis manufactured using the method of any one of embodiments 85 to 142;
connecting an inlet of the vascular prosthesis to a first blood vessel; and
connecting an outlet of the vascular prosthesis to a second blood vessel;
such that blood can flow between the first and second blood vessels through the vascular prosthesis.

Embodiment 205. The method of embodiment 204, wherein the first and second blood vessels are formed from a blood vessel which is diseased, or has been severed, bisected, or the like.

Embodiment 206. A method of implanting a vascular prosthesis, the method comprising the steps of:
providing a vascular prosthesis according to any one of embodiments 143 to 161;
connecting the vascular prosthesis to a first blood vessel; and
connecting the vascular prosthesis to a second blood vessel;
such that blood can flow between the first and second blood vessels through the vascular prosthesis.

Embodiment 207. The method of embodiment 206, wherein the first and second blood vessels are formed from a blood vessel which is diseased, or has been severed, bisected, or the like.

Embodiment 207. A method of implanting a vascular system, the method comprising the steps of:
providing a vascular system, the vascular system comprising:
a vascular prosthesis manufactured according to any one of embodiments 85 to 142; and
a further prosthesis;
wherein the vascular prosthesis is connectable to the further prosthesis;
connecting the vascular prosthesis to the further prosthesis, such that blood can flow therebetween;
connecting an end of a blood vessel to the vascular prosthesis; and
connecting the further prosthesis to the heart;
such that blood can flow between the blood vessel and the heart through the vascular system.

Embodiment 209. The method of embodiment 208, wherein the further prosthesis is at least one of: a biological heart valve, a synthetic heart valve, a cardiac assist device, and a ventricular assist device, or the like.

What is claimed is:

1. A medical textile product comprising:
a textile substrate having opposed first and second surfaces, the textile substrate comprising a textile construction of one or more yarns;
wherein the second surface comprises a coating of a substantially water-insoluble, non-porous elastomeric sealant, disposed thereon;
wherein the one or more yarns at the first surface are pre-treated with a removable composition, which removable composition is substantially removed prior to use or implantation, such that the water-insoluble elastomeric sealant encapsulates a portion of fibers of the one or more yarns at the second surface of the textile substrate;
wherein the textile substrate is substantially impermeable to fluid; and
wherein the first surface is substantially free of the substantially water-insoluble elastomeric sealant.

2. The medical textile product of claim 1, wherein the first surface is at least 70% free of the substantially water-insoluble elastomeric sealant.

3. The medical textile product of claim 1, wherein the first surface is at least 80% free of the substantially water-insoluble elastomeric sealant.

4. The medical textile product of claim 1, wherein the first surface is at least 90% free of the substantially water-insoluble elastomeric sealant.

5. The medical textile product of claim 1, wherein the first surface is at least 95% free of the substantially water-insoluble elastomeric sealant.

6. The medical textile product of claim 1, wherein the textile construction is selected from the group consisting of a weave of the one or more yarns, a knit of the one or more yarns, a braid of the one or more yarns, a web of the one or more yarns, a felt of the one or more yarns, and a mesh of the one or more yarns.

7. The medical textile product of claim 1, wherein the coating is disposed within an intermediate portion of the non-tubular textile substrate between the second surface and the first surface.

8. The medical textile product of claim 1, wherein the substantially water-insoluble elastomeric sealant is a material selected from the group consisting of silicones, polyurethanes, polycarbonates, thermoplastic elastomers, and combinations thereof.

9. The medical textile product of claim 1, wherein the removable composition is a water-soluble material is selected from the group consisting of polyvinylpyrrolidone, glycerol, methyl cellulose, poly(ethylene glycol), poly(ethylene glycol) hydrogel, polyethylene oxide, and combinations thereof.

10. The medical textile product of claim 1,
wherein one portion of the textile substrate has a first level of the substantially water-insoluble elastomeric sealant to provide a first soft, flexible zone;
wherein another portion of the textile substrate has a second level of the substantially water-insoluble elastomeric sealant to provide a second zone having a stiffness greater than the first zone; and
wherein the second level the substantially water-insoluble elastomeric sealant is greater than the first level of the substantially water-insoluble sealant.

11. The medical textile product of claim 10, wherein the textile substrate has a plurality of portions having different levels of the substantially water-insoluble elastomeric sealants to provide a plurality of portions having different levels of stiffnesses.

12. The medical textile product of claim 1, wherein the coating of the substantially water-insoluble elastomeric sealant is disposed within an intermediate portion of the textile substrate between the second surface and the first surface.

13. The medical textile product of claim of claim 1, wherein the textile substrate is a non-tubular substrate.

14. The medical textile product of claim 13, wherein the non-tubular textile substrate is selected from the group consisting a planar sheet, a shaped sheet, and a tape.

15. The medical textile product of claim 13, wherein the medical textile product is selected from the group consisting a mesh, a patch, a hernia plug, and vascular wrap.

16. The medical textile product of claim 1, wherein the substantially water-insoluble elastomeric sealant further comprises a material selected from the group consisting of a colorant, a dye, a pigment, and a fluorescent indicator.

17. The medical textile product of claim 13, wherein the substantially water-insoluble elastomeric sealant further comprises a material selected from the group consisting of a colorant, a dye, a pigment, and a fluorescent indicator.

18. The medical textile product of claim 1, wherein the textile substrate is a tubular substrate.

19. The medical textile product of claim 18, wherein the tubular textile substrate is a conduit selected from the group consisting of a cylindrical conduit, a tubular conduit, a Y-shaped, a T-shaped conduit, a multi-channel conduit, a bulbous shaped conduit, and combinations thereof.

20. The medical textile product of claim 19, wherein the textile construction of one or more yarns defines the tubular textile wall, wherein the first surface is an inner surface of the tubular textile wall; and wherein the second surface is an outer surface of the tubular textile wall.

21. The medical textile product of claim 20, further comprising a support member disposed about the tubular textile wall.

22. The medical textile product of claim 21, wherein the support member is disposed about the outer surface of the tubular textile wall.

23. The medical textile product of claim 22, wherein the support member is wrapped around the outer surface of the tubular textile wall.

24. The medical textile product of claim 20, wherein the tubular textile wall comprises a plurality of crimps, and the support member is arranged to nest between the plurality of crimps.

25. The medical textile product of claim 21, wherein the support member is a flexible, polymer member.

26. The medical textile product of claim 21, wherein the support member is a metallic member.

27. The medical textile product of claim 13, further comprising a support member disposed along a portion of the second surface of the textile substrate.

28. The medical textile product of claim 13, further comprising a support member disposed along a portion of the first surface of the textile substrate.

29. The medical textile product of claim 28, further comprising a support member disposed along a portion of the first surface of the textile substrate.

30. The medical textile product of claim 1, wherein the removable composition is a coating or layer.

* * * * *